(12) United States Patent
Krishnan et al.

(10) Patent No.: US 10,151,762 B2
(45) Date of Patent: *Dec. 11, 2018

(54) BACTERIOPHAGE GENE 3 PROTEIN COMPOSITIONS AND USE AS AMYLOID BINDING AGENTS

(71) Applicant: PROCLARA BIOSCIENCES, INC., Cambridge, MA (US)

(72) Inventors: Rajaraman Krishnan, Ashland, MA (US); Richard Fisher, Cambridge, MA (US)

(73) Assignee: Proclara Biosciences, Inc., Cambridge, MA (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/288,237

(22) Filed: Oct. 7, 2016

(65) Prior Publication Data

US 2017/0115311 A1 Apr. 27, 2017

Related U.S. Application Data

(62) Division of application No. 14/361,157, filed as application No. PCT/US2012/066793 on Nov. 28, 2012, now Pat. No. 9,493,515.

(Continued)

(51) Int. Cl.
*A61K 48/00* (2006.01)
*C07K 14/01* (2006.01)
(Continued)

(52) U.S. Cl.
CPC ....... *G01N 33/6893* (2013.01); *A61K 38/162* (2013.01); *A61K 47/665* (2017.08); *A61K 51/08* (2013.01); *A61K 51/1093* (2013.01);
*B82Y 5/00* (2013.01); *C07K 14/005* (2013.01); *C07K 14/24* (2013.01); *C07K 16/00* (2013.01); *C07K 16/18* (2013.01); *C12N 7/00* (2013.01);
(Continued)

(58) Field of Classification Search
None
See application file for complete search history.

(56) References Cited

U.S. PATENT DOCUMENTS

| | | |
|---|---|---|
| 3,941,763 A | 3/1976 | Sarantakis |
| 4,215,051 A | 7/1980 | Schroeder et al. |

(Continued)

FOREIGN PATENT DOCUMENTS

| | | |
|---|---|---|
| EP | 0 154 316 B1 | 9/1989 |
| EP | 0 401 384 B1 | 3/1996 |

(Continued)

OTHER PUBLICATIONS

Aguib et al. (2009) "Autophagy induction by trehalose counteracts cellular prion infection" *Autophagy*, 5(3):361-369.

(Continued)

*Primary Examiner* — Jeffrey Stucker
*Assistant Examiner* — Aurora M Fontainhas
(74) *Attorney, Agent, or Firm* — Finnegan, Henderson, Farabow, Garrett & Dunner, LLP

(57) ABSTRACT

The invention relates to agents and to pharmaceutical compositions for reducing the formation of amyloid and/or for promoting the disaggregation of amyloid proteins. The compositions may also be used to detect amyloid.

12 Claims, 52 Drawing Sheets

Specification includes a Sequence Listing.

Related U.S. Application Data

(60) Provisional application No. 61/730,316, filed on Nov. 27, 2012, provisional application No. 61/708,709, filed on Oct. 2, 2012, provisional application No. 61/564,602, filed on Nov. 29, 2011.

(51) Int. Cl.

| | | |
|---|---|---|
| G01N 33/68 | (2006.01) | |
| A61K 38/16 | (2006.01) | |
| B82Y 5/00 | (2011.01) | |
| A61K 51/10 | (2006.01) | |
| C07K 14/24 | (2006.01) | |
| C07K 16/00 | (2006.01) | |
| C07K 14/005 | (2006.01) | |
| C12N 7/00 | (2006.01) | |
| A61K 51/08 | (2006.01) | |
| C07K 16/18 | (2006.01) | |
| C12P 21/02 | (2006.01) | |
| G01N 33/60 | (2006.01) | |
| A61K 47/66 | (2017.01) | |
| A61K 38/00 | (2006.01) | |

(52) U.S. Cl.
CPC .............. *C12P 21/02* (2013.01); *G01N 33/60* (2013.01); *A61K 38/00* (2013.01); *C07K 2319/30* (2013.01); *C12N 2795/14122* (2013.01); *C12N 2795/14133* (2013.01); *C12N 2795/14171* (2013.01); *C12N 2795/18022* (2013.01); *C12N 2795/18033* (2013.01); *G01N 2800/28* (2013.01); *G01N 2800/7047* (2013.01)

(56) References Cited

U.S. PATENT DOCUMENTS

| | | | |
|---|---|---|---|
| 5,252,714 A | 10/1993 | Harris et al. | |
| 5,480,981 A | 1/1996 | Goodwin et al. | |
| 5,808,029 A | 9/1998 | Brockhaus et al. | |
| 6,686,179 B2 | 2/2004 | Fleer et al. | |
| 7,208,147 B2 | 4/2007 | Carr et al. | |
| 7,867,487 B2 | 1/2011 | Solomon et al. | |
| 8,022,270 B2 | 9/2011 | Dickey et al. | |
| 9,493,515 B2 | 11/2016 | Krishnan et al. | |
| 9,493,516 B2 | 11/2016 | Krishnan et al. | |
| 2002/0052311 A1 | 5/2002 | Solomon et al. | |
| 2007/0269435 A1 | 11/2007 | Gillies et al. | |
| 2009/0105090 A1 | 4/2009 | Uchiyama | |
| 2009/0180991 A1 | 7/2009 | Solomon et al. | |
| 2009/0304726 A1 | 12/2009 | Solomon et al. | |
| 2009/0317324 A1 | 12/2009 | Solomon et al. | |
| 2009/0324554 A1 | 12/2009 | Solomon et al. | |
| 2010/0113304 A1* | 5/2010 | Hufton ............... | C12N 15/1037 506/14 |
| 2010/0137420 A1 | 6/2010 | Nath | |
| 2011/0142803 A1 | 6/2011 | Solomon et al. | |
| 2011/0182948 A1 | 7/2011 | Solomon et al. | |
| 2014/0335016 A1 | 11/2014 | Krishnan | |
| 2015/0376239 A1 | 12/2015 | Krishnan et al. | |
| 2016/0009766 A1 | 1/2016 | Krishnan et al. | |
| 2016/0115223 A1 | 4/2016 | Fisher et al. | |

FOREIGN PATENT DOCUMENTS

| | | |
|---|---|---|
| JP | 2008-528688 A | 7/2008 |
| WO | WO 92/16221 A1 | 10/1992 |
| WO | WO 95/34326 A1 | 12/1995 |
| WO | WO 98/52976 A1 | 11/1998 |
| WO | WO 00/34317 A2 | 6/2000 |
| WO | WO 2002/074243 A2 | 9/2002 |
| WO | WO 2004/018385 A2 | 3/2004 |
| WO | WO 2006/083795 A1 | 8/2006 |
| WO | WO 2007/094003 A2 | 8/2007 |
| WO | WO 2008/011503 A2 | 1/2008 |
| WO | WO 2008/044032 A2 | 4/2008 |
| WO | WO 2009/143465 A1 | 11/2009 |
| WO | WO 2009/143470 A1 | 11/2009 |
| WO | WO 2010/060073 A2 | 5/2010 |
| WO | WO 2011/084714 A2 | 7/2011 |
| WO | WO 2012/125556 A1 | 9/2012 |
| WO | WO 2013/082114 A1 | 6/2013 |
| WO | WO 2014/055515 A1 | 4/2014 |
| WO | WO 2014/193935 A1 | 12/2014 |
| WO | WO 2016/090022 A1 | 6/2016 |

OTHER PUBLICATIONS

Aguzzi & O-Connor (2010) "Protein aggregation diseases: pathogenicity and therapeutic perspectives" *Nature Reviews: Drug Discovery.* 9:237-48.

Aruffo et al. (1990) "CD44 Is the Principal Cell Surface Receptor for Hyaluronate" *Cell*, 61:1303-13.

Ashkenazi et al. (1991) "Protection against endotoxic shock by a tumor necrosis factor receptor immunoadhesin" *Proc. Natl. Acad. Sci. USA*, 88:10535-39.

Beck et al. (1978) "Nucleotide sequence of bacteriophage fd DNA" *Nucleic Acids Research*, 5(12):4495-503.

Bennett et al. (1991) "Extracellular Domain-IgG Fusion Proteins for the Three Human Natriuretic Peptide Receptors" *J. Biol. Chem.*, 266(34):23060-67.

Byrn et al. (Apr. 1990) "Biological properties of a CD4 immunoadhesin" *Nature*, 344:667-70.

Capon et al. (Feb. 1989) "Designing CD4 immunoadhesins for AIDS therapy" *Nature*, 337:525-31.

Cascales et al., (2007) "Colicin Biology" *Microbiol. Mol. Biol. Rev.*, 71(1):158-229.

Chalupny et al. (1992) "T-cell activation molecule 4-1BB binds to extracellular matrix proteins" *Proc. Natl. Acad. Sci. USA*, 89:10360-64.

Chang and Kuret (2008) "Detection and Quantification of Tau Aggregation Using a Membrane Filter Assay" *Anal. Biochem.*, 373(2):330-6. NIH Public Access Author Manuscript; available in PMC Feb. 15, 2009 (13 pages).

Chiti & Dobson (2006) "Protein Misfolding, Functional Amyloid, and Human Disease" *Annu. Rev. Biochem.*, 75:333-66.

Coruzzi et al. (1984) "Tissue-specific and light-regulated expression of a pea nuclear gene encoding the small subunit of ribulose-1,5-bisphosphate carboxylase" *EMBO J.*, 3:1671-79.

Darocha-Souto et al. (2011) "Brain Oligomeric β-Amyloid but Not Total Amyloid Plaque Burden Correlates With Neuronal Loss and Astrocyte Inflammatory Response in Amyloid Precursor Protein/Tau Transgenic Mice" *J. Neuropathol. Exp. Neurol.*, 70(5):360-76. NIH Public Access Author Manuscript; available in PMC Jul. 29, 2013 (26 pages).

Dehay et al. (2015) "Targeting α-synuclein for treatment of Parkinson's disease: mechanistic and therapeutic considerations" *Lancet Neurol.*, 14:855-866.

Deng and Perham (2002) "Delineating the Site of Interaction on the pIII Protein of Filamentous Bacteriophage fd with the F-pilus of *Escherichia coli*" *J. Mol. Biol.*, 319:603-14.

Devlin et al. (1990) "Random Peptide Libraries: A Source of Specific Protein Binding Molecules" *Science*, 249:404-06.

Dimant et al. (2009) "Modulation effect of filamentous phage on alpha-synuclein aggregation" *Biochem. Biophys. Res. Commun.*, 383(4):491-496.

Duyckaerts et al. (2008) "Alzheimer disease models and human neuropathology: similarities and differences" *Acta Neuropathol.*, 115:5-38.

Eckert et al. (2007) "A Conformational Unfolding Reaction Activates Phage fd for the Infections of *Escherichia coli*" *J. Mol. Biol,.* 373(2):452-461.

Eichner and Radford (2011) "A Diversity of Assembly Mechanisms of a Generic Amyloid Fold" *Mol. Cell.* 43:8-18.

Gascoigne et al. (1987) "Secretion of a chimeric T-cell receptor-immunoglobulin protein" *Proc. Natl. Acad. Sci. USA*, 84:2936-40.

(56) References Cited

OTHER PUBLICATIONS

Gentz et al. (1989) "Bioassay for trans-activation using purified human immunodeficiency virus tat-encoded protein: Trans-activation requires mRNA synthesis" *Proc. Natl. Acad. Sci. USA*, 86:821-24.
Gurley et al. (1986) "Upstream Sequences Required for Efficient Expression of a Soybean Heat Shock Gene" *Mol. Cell. Biol.*, 6:559-65.
Heiseke et al. (2009) "Lithium induces clearance of protease resistant prion protein in prion-infected cells by induction of autophagy" *J. Neurochem.*, 109:25-34.
Hill and Petersen (1982) "Nucleotide sequence of bacteriophage 11 DNA" *J. Virol.*, 44(1):32-46.
Hoffmann-Thoms et al. (May 2013) "Initiation of Phage Infection by Partial Unfolding and Prolyl Isomerization" *J. Biol. Chem.*, 288(18):12979-91.
Holliger et al. (1999) "Crystal Structure of the Two N-terminal Domains of g3p from Filamentous Phage fd at 1.9 Å Evidence for Conformational Lability" *J. Mol. Biol.*, 288(4):649-57.
Hsiao et al. (1996) "Correlative Memory Deficits, Aβ Elevation, and Amyloid Plaques in Transgenic Mice" *Science*, 274:99-102.
Hughes (2004) "The value of spontaneous alternation behavior (SAB) as a test of retention in pharmacological investigations of memory" *Neurosci. Biobehav. Rev.* 28:497-505.
International Patent Application No. PCT/US2012/066793, filed Nov. 28, 2012, by Neurophage Pharmaceuticals, Inc.: International Preliminary Report on Patentability, dated Feb. 6, 2014.
International Patent Application No. PCT/US2012/066793, filed Nov. 28, 2012, by Neurophage Pharmaceuticals, Inc.: International Search Report and Written Opinion, dated Apr. 19, 2013.
International Patent Application No. PCT/US2013/062862, filed Oct. 1, 2013, by Neurophage Pharmaceuticals, Inc.: International Search Report and Written Opinion, dated Feb. 24, 2014.
International Patent Application No. PCT/US2014/039760, filed May 28, 2014, by Neurophage Pharmaceuticals, Inc.: International Search Report and Written Opinion, dated Nov. 3, 2014.
International Patent Application No. PCT/US2014/039760, filed May 28, 2014, by Neurophage Pharmaceuticals, Inc.: Written Opinion of the International Preliminary Examining Authority, dated May 15, 2015.
International Patent Application No. PCT/US2014/039760, filed May 28, 2014, by Neurophage Pharmaceuticals, Inc.: International Preliminary Report on Patentability, dated Aug. 14, 2015.
International Patent Application No. PCT/US2015/063476, filed Dec. 2, 2015, by Neurophage Pharmaceuticals, Inc.: International Search Report and Written Opinion, dated May 3, 2016.
International Patent Application No. PCT/US2015/063476, filed Dec. 2, 2015, by Neurophage Pharmaceuticals, Inc.: Written Opinion, dated Oct. 26, 2016.
Josephs et al. (2011) "Neuropathological background of phenotypical variability in frontotemporal dementia" *Acta Neuropathol.*, 122:137-53.
Kather et al. (2005) "A Stable Disulfide-free Gene-3-protein of Phage fd Generatied by In vitro Evolusion" *J. Mol. Biol.*, 354(3):666-678.
Kerr et al (2001) "Lysostaphin expression in mammary glands confers protection against staphylococcal infection in transgenic mice" *Nature Biotechnol.*, 19(1):66-70.
King et al. (1999) "Progressive and gender-dependent cognitive impairment in the APP$_{SW}$ transgenic mouse model for Alzheimer's disease" *Brain Res.*, 103:145-62.
Kingstedt and Nilsson (2012) "Luminescent conjugated poly- and oligo-thiophenes: optical ligands for spectral assignment of a plethora of protein aggregates" *Biochem. Soc. Trans.*, 40(4):704-710.
Kong, B. et al. (2006) "Display of aggregation-prone ligand binding domain of human PPAR gamma on surface of bacteriophage lambda" *Acta Pharmologica Sinica*, 27(1):91-99.
Kosik et al. (1986) "Microtubule-associated protein tau (tau) is a major antigenic component of paired helical filaments in Alzheimer disease" *Proc. Natl. Acad. Sci. USA*, 83(11):4044-48.

Krishnan et al. (2014) "A Bacteriophage Capsid Protein Provides a General Amyloid Interaction Motif (GAIM) That Binds and Remodels Misfolded Protein Assemblies" *J. Mol. Biol.*, 426:2500-2519.
Kurschner et al. (1992) "Construction, Purification, and Characterization of New Interferon γ(IFNγ) Inhibitor Proteins" *J. Biol. Chem.*, 267:9354-60.
Lalonde et al. (2012) "Neurologic and motor dysfunctions in APP transgenic mice" *Rev. Neurosci.*, 23(4):363-79 NIH Public Access Author Manuscript, available in PMC Jan. 1, 2013 (25 pages).
Lalonde & Strazielle (2012) "Brain regions and genes affecting myoclonus in animals" *Neurosci. Res.*, 74(2):69-79.
Lee et al. (2001) "Neurodegenerative Tauopathies" *Annu. Rev. Neurosci.*, 24:1121-59.
Lesslauer et al. (1991) "Recombinant soluble tumor necrosis factor receptor proteins protect mice from lipopolysaccharide-induced lethality" *Eur. J. Immunol.*, 21(11):2883-86.
Lewis et al. (2000) "Neurofibrillary tangles, amyotrophy and progressive motor disturbance in mice expressing mutant (P301L) tau protein" *Nat. Genet.*, 25:402-5.
Li et al. (2015) "Trehalose Decreases Mutant SOD1 Expression and Alleviates Motor Deficiency in Early but Not End-Stage Amyotrophic Lateral Scierosis in a SOD1-G93A Mouse Model" *Neurosci.*, 298:12-25.
Li et al. (2011) "Inhibition of Bacterial Conjugation by Phage M13 and Its Protein g3p: Quantitative Analysis and Model" *PLoS ONE*,6(5):e19991. doi:10.1371/journal.pone.0019991 (11 pages).
Linsley et al. (1991) "Binding of the B cell activation antigen B7 to CD28 costimulates T cell proliferation and interleukin 2 mRNA accumulation" *J. E. Med.*, 173:721-30.
Linsley et al. (1991) "CTLA-4 is a Second Receptor for the B Cell Activation Antigen B7" *J. Exp. Med.*, 174:561-69.
Liu et al. (2005) "Trehalose differentially inhibits aggregation and neurotoxicity of beta-amyloid 40 and 42" *Neurobiol. Dis.*, 20:74-81.
Lo et al. (1998) "High level expression and secretion of Fc-X fusion proteins in mammalian cells" *Protein Engineering*, 11(6):495-500.
Logan and Shenk (1984) "Adenovirus tripartite leader sequence enhances translation of rnRNAs late after infection" *Proc, Natl. Acad. Sci. USA*, 81:3655-59.
Lorenz et al. (2011) "The Filamentous Phages fd and IF1 Use Different Mechanisms to Infect *Escherchia coli*" *J. Mol. Biol.*, 405:989-1003.
Lubkowski et al. (1998) "Filamentous phage infection: crystal structure of g3p in complex with its coreceptor, the C-terminal domain of ToiA" *Structure*, 7(6):711-22.
Luo et al. (2012) "Probing of C-terminal lysine variation in a recombinant monoclonal antibody production using Chinese hamster ovary cells with chemically defined media" *Biotechnol. Bioeng.*, 109(9):2306-15.
Mackett et al. (1982) "Vaccinia virus. A selectable eukaryotic cloning and expression vector" *Proc. Natl. Acad Sci. USA,*. 79:7415-19.
Mackett et al. (1984) "General Method for Production and Selection of Infectious Vaccinia Virus Recombinants Expressing Foreign Genes" *J. Virol.*, 49:857-84.
Martin and Schmid (2003) "Evolutionary Stabilization of the Gene-3-protein of Phage fd Reveals the Principles that Govern the Thermodynamic Stability of Two-domain Proteins" *J. Mol. Biol.*, 328:863-75.
Marvin (1998) "Filamentous phage structure, infection and assembly" *Curr. Opin. in Struct. Biol.*, 8:150-8.
Masliah et al. (2000) "Dopaminergic Loss and Inclusion Body Formation in α-Synuclein Mice: Implications for Neurodegenerative Disorders" *Science* 287:1265-69.
McKhann et al. (2011) "The diagnosis of dementia due to Alzheimer's disease: Recommendations from the National Institute on Aging and the Alzheimer's Association workgroup" [Article in Press] *Alzheimer's & Dementia*, doi:10.1016/j.jalz 2011.03.005, 7 pages: final publication in 7(3):263-9.
Mega et al. (1996) "The spectrum of behavioral changes in Alzheimer's disease" *Neurology*, 46:130-5.
Messing and Ayer, "Enterobacteria phage M13 isolate WT variety Rutgers, complete genome" GenBank Database Accession No. JX412914, Version GI:401823911; submitted Jul. 20, 2012.

(56) References Cited

OTHER PUBLICATIONS

Muir, E.M. et al. (2010) "Modification of N-glycosylation sites allows secretion of bacterial chondroitinase ABC from mammalian cells" *J. Biotechnol.*, 145(2):103-110.

Olofsson et al. (2006) "The Solvent Protection of Alzheimer Amyloid-β-(1-42) Fibrils as Determined by Solution NMR Spectroscopy" *J. Biol. Chem.*, 281(1):477-83.

Panicali et al. (1982) "Construction of poxviruses as cloning vectors: Insertion of the thymidine kinase gene from herpes simplex virus into the DNA of infectious vaccinia virus" *Proc. Natl. Acad. Sci. USA*, 79:4927-31.

Pankiewicz et al. (2006) "Clearance and prevention of prion infection in cell culture by anti-PrP antibodies" NIH Public Access Author Manuscript, available in PMC Jan. 22, 2007. Final publication in: *Eur. J. Neurosci.*, 23:2635-47.

Peppel et al. (1991) "A tumor necrosis factor (TNF) receptor-IgG heavy chain chimeric protein as a bivalent antagonist of TNF activity" *J. Exp. Med.*, 174:1483-89.

Perrier et al. (2004) "Anti-Prp antibodies block $PrP^{Sc}$ replication in prion-infected cell cultures by accelerating $PrP^{C}$ degradation" *J. Neurochem.*, 84:454-63.

Petkova et al. (2005) "Self-propagating, molecular-level polymorphism in Alzheimer's β-amyloid fibrils" *Science*, 307:262-65.

Rasched and Oberer (1986) "Ff Coilphages: Structural and Functional Relationships" *Microbiol, Rev.*, 50:401-27.

REFSEQ database Accession No. NC_003287.2, version GI:56718463.

Resnick and Sojkova (2011) "Amyloid imaging and memory change for prediction of cognitive impairment" *Alzheimer's Res Ther.*, 3:3, doi:10.1186/alzrt62 [online]. Retreived from: http://alzres.com/content/3/1/3.

Robinson et al. (2015) "Drugs and drug delivery systems targeting amyloid-β in Alzheimer's disease" *Mol. Sci.*, 2(3):332-358.

Sadowski et al. (2009) "Anti-PrP Mab 6D11 suppresses $PrP^{Sc}$ replication in priori infected myeloid precursor line FDC-P1/22L and in the lymphoreticular system in vivo" NIH Public Access Author Manuscript, available. Jul. 20, 2009, Final publication in: *Neurobiol Dis.*, 34(2): 267-78.

Sánchez et al. (2011) "Aβ40 and Aβ42 Amyloid Fibrils Exhibit Distinct Molecular Recycling Properties" *J. Am. Chem. Soc.*, 133:6505-08.

Sarkar et al. (2005) "Lithium induces autophagy by inhibiting inositol monophosphatase" *J of Cell Biol*, 170(7):1101-11.

Sarkar et al. (2007) "Trehalose, a Novel mTOR-independent Autophagy Enhancer, Accelerates the Clearance of Mutant Huntingtin and -α-Synuclein" *J Biol. Chem.*, 282(8):5641-52.

Sato et al. (2006) "Inhibitors of Amyloid Toxicity Based on β-sheet Parking of Aβ40 and Aβ42" *Biochemistry*, 45:5503-16.

Sciarretta et al. (2006) "Peptide-Based Inhibitors of Amyloid Assembly" *Meth. Enzymol.*, 413:273-312.

Scott and Smith (1990) "Searching for Peptide Ligands with an Epitope Library" *Science*, 249:386-90.

Simonsen and Levinson (1983) "Isolation and expression of an altered mouse dihydrofolate reductase cDNA" *Proc. Natl. Acad. Sci. USA*, 80:2495-99.

Smith et al. (1983) "Molecular Engineering of the *Autographa californica* Nuclear Polyhedrosis Virus Genome: Deletion Mutations Within the Polyhedrin Gene" *J. Virol.*, 46:584-93.

Smith et al. (1997) "Phage display" *Chem. Rev.*, 97:391-410.

Stamenkovic et al. (1991) "The B Lymphocyte Adhesion Molecule CD22 Interacts with Leukocyte Common Antigen CD45RO on T Cells and α2-6 Sialyltransferase, CD75, on B Cells" *Cell*, 66:1133-44.

Stassen et al. (1992) "Nucleotide Sequence of the Genorne of the Filamentous Bacteriophage I2-2: Module Evolution of the Filamentous Phage Genome" *J. Mol. Evol.*, 34:141-52.

Sterniczuk et al., (2010) "Characterization of the 3xTg-AD mouse model of Alzheimer's disease: Part 1. Circadian changes" *Brain Res.*, 1348:139-48.

Sterniczuk et al. (2010) "Characterization of the 3xTg-AD mouse model of Alzheimer's disease: Part 2. Behavioral and cognitive changes" *Brain Res.*, 1348:149-55.

Stine et al. (2003) "In Vitro Characterization of Conditions for Amyloid-β Peptide Oligomerization and Fibrillogenesis" *J. Biol. Chem.*, 278(13):11612-22.

Stine et al. (2011) "Preparing synthetic Aβ in different aggregation states" HHS Public Access Author Manuscript, available Aug. 26, 2013, PMCID: PMC3752843. Final publication in: *Methods Mol. Biol.*, 670: 13-32.

Sunde et al. (1997) "Common Core Structure of Amyloid Fibrils by Synchroton X-ray Diffraction" *J. Mol. Biol.*, 273:729-39.

Takamatsu et al. (1987) "Expression of bacterial chloramphenicol acetyltransferase gene in tobacco plants mediated by TMV-RNA" *EMBO J.*, 6:307-11.

Terpe (2003) "Overview of tagg protein fusions: from molecular and biochemical fundamentals to commercial systems" *Appl. Microbiol. Biotechnol.*, 60:523-533.

Tjernberg et al. (1996) "Arrest of β-Amyloid Fibril Formation by a Pentapeptide Ligand" *J. Biol. Chem.*, 271(12):8545-48.

Traunecker et al. (May 1989) "Highly efficient neutralization of HIV with recombinant CD4-immunoglobulin molecules" *Nature*, 339:68-70.

UNIPROT Accession No. O80297 (Entry date: Jul. 15, 1999) "Protein: Attachment protein G3P. Organism: *Enterobacteria phage If1 (Bacteriophage If1).*" [online]. Retreived from the Internet: http://www.uniprot.org/uniprot/O80297.

UNIPROT Accession No. P03661 (Entry date: Jul. 21, 1986) "Protein: Attachment protein G3P. Organism: *Enterobacteria phage fd (Bacteriophage fd).*" [online]. Retreived from the Internet: http://www.uniprot.org/uniprot/P03661.

UNIPROT Accession No. P03663 (Entry date: Jul. 21, 1986) "Protein: Attachment protein G3P. Organism: *Enterobacteria phage IKe (Bacteriophage IKe).*" [online]. Retreived from the Internet: http://www.uniprot.org/uniprot/P03663.

UNIPROT Accession No. P15415 (Entry date: Apr. 1, 1990) "Protein: Attachment protein G3P. Organism: *Enterobacteria phage I2-2 (Bacteriophage I2-2).*" [online]. Retreived from the Internet: http://www.uniprot.org/uniprot/P15415.

UNIPROT Accession No. P69168 (Entry date: Jul. 21, 1986) "Protein: Attachment protein G3P. Organism: *Enterobacteria phage M13 (Bacteriophage M13).*" [online]. Retreived from the Internet: http://www.uniprot.org/uniprot/P69168.

UNIPROT Accession No. P69169 (Entry date: Jul. 21, 1986) "Protein: Attachment protein G3P. Organism: *Enterobacteria phage f1 (Bacteriophage f1).*" [online]. Retreived from the Internet: http://www.uniprot.org/uniprot/P69169.

U.S. Appl. No. 62/087,052, filed Dec. 3, 2014, by Rajaraman Krishnan, et al.

Van Wezenbeek et al. (1980) "Neucleotide sequence of the filamentous bacteriophage M13 DNA genome: comparison with phage fd" *Gene*, 11:129-48.

Van Wezenbeek et al. "Structural protein [Enterobacteria phage M13]" NCBI Protein Sequence Database Accession No. NP_510891. 1, Version GI:17426224; submitted Dec. 8, 2001.

Wang et al. (2010) "Generating a Prion with Bacterially Expressed Recombinant Prion Protein" *Science*, 327:1132-35.

Wang et al. (2010) "Degradation of TDP-43 and its pathogenic form by a autophagy and the ubiquitin-proteasome system" *Neurosci. Lett.*, 469:112-116.

Wanker et al. (1999) "Membrane Filter Assay for Detection of Amyloid-like Polyglutamine-Containing Protein Aggregates" *Methods Enzymol.*, 309:375-86.

Watson et al. (1990) "A homing receptor-IgG chimera as a probe for adhesive ligands of lymph node high endothelial venules" *J. Cell. Biol.*, 110:2221-29.

Watson et al. (Jan. 1991) "Neutrophil influx into an inflammatory site inhibited by a soluble homing receptor-IgG chimaera" *Nature*, 349:164-67.

Whittemore et al. (2005) "Hydrogen-Deuterium (H/D) Exchange Mapping of $Aβ_{1-40}$ Amyloid Fibril Secondary Structure Using Nuclear Magnetic Resonance Spectroscopy" *Biochemistry*, 44:4434-41.

(56) References Cited

OTHER PUBLICATIONS

Wilcock et al. (2004) "Passive Amyloid Immunotherapy Clears Amyloid and Transiently Activates Microglia in a Transgenic Mouse Model of Amyloid Deposition" *J. Neurosci.*, 24(27);6144-51.

Yamaguchi et al. (2004) "Core and Heterogeneity of β2-Microglobulin Myloid Fibrils as Revealed by H/D Exchange" *J Mol. Biol.*, 338:559-71.

Zettmeissl et al. (1990) "Expression and characterization of human CD4: immunoglobulin fusion proteins" *DNA Cell Biol.*, 9(5):347-53.

Zhao et al, (2012) "Tagged and untagged TRAIL show different activity against tumor cells" *Oncol. Lett.*, 4:1301-4.

Zheng et al (1995) "Administration of noncytolytic IL-10/Fc in murine models of lipopolysaccharide-induced septic shock and allogeneic islet transplantation" *J. Immun.*, 154:5590-5600.

\* cited by examiner

```
M13-MKKLLFAIPLVVPFYSHSAETVESCLAKPHTENSFTNVWKDDKTLDRYANYEGCLWNATG 60
Fd- ------------------------------------------------------------ 60
F1- ------------------------------------------------------------ 60
Con MKKLLFAIPLVVPFYSHSAETVESCLAKPHTENSFTNVWKDDKTLDRYANYEGCLWNATG

M13-VVVCTGDETQCYGTWVPIGLAIPENEGGGSEGGGSEGGGSEGGGTKPPEYGDTPIPGYTY 120
Fd- ------------------------------------------------------------ 120
F1- ------------------------------------------------------------ 120
Con VVVCTGDETQCYGTWVPIGLAIPENEGGGSEGGGSEGGGSEGGGTKPPEYGDTPIPGYTY

M13-INPLDGTYPPGTEQNPANPNPSLEESQPLNTFMFQNNRFRNRQGALTVYTGTVTQGTDPV 180
Fd- ------------------------------------------------------------ 180
F1- ------------------------------------------------------------ 180
Con INPLDGTYPPGTEQNPANPNPSLEESQPLNTFMFQNNRFRNRQGALTVYTGTVTQGTDPV

M13-KTYYQYTPVSSKAMYDAYWNGKFRDCAFHSGFNEDPFVCEYQGQSSDLPQPPVNAGGGSG 240
Fd- ------------------------------------------------------------ 240
F1- ------------------------------------------------------------ 240
Con KTYYQYTPVSSKAMYDAYWNGKFRDCAFHSGFNEDPFVCEYQGQSSDLPQPPVNAGGGSG

M13-GGSGGGSEGGGSEGGGSEGGGSEGGGSGGGSGSGDFDYEKMANANKGAMTENADENALQS 300
Fd- ------------------------------------------------------------ 300
F1- ------------------------------------------------------------ 300
Con GGSGGGSEGGGSEGGGSEGGGSEGGGSGGGSGSGDFDYEKMANANKGAMTENADENALQS

M13-DAKGKLDSVATDYGAAIDGFIGDVSGLANGNGATGDFAGSNSQMAQVGDGDNSPLMNNFR 360
Fd- ------------------------------------------------------------ 360
F1- ------------------------------------------------------------ 360
Con DAKGKLDSVATDYGAAIDGFIGDVSGLANGNGATGDFAGSNSQMAQVGDGDNSPLMNNFR

M13-QYLPSLPQSVECRPFVFSAGKPYEFSIDCDKINLFRGVFAFLLYVATFMYVFSTFANILR 420
Fd- ---------------Y--G----------------------------------------- 420
F1- ------------------G----------------------------------------- 420
Con QYLPSLPQSVECRPX--XAGKPYEFSIDCDKINLFRGVFAFLLYVATFMYVFSTFANILR

M13-NKES 424 (SEQ ID NO:1)
Fd- ---- 424 (SEQ ID NO:2)
F1- ---- 424 (SEQ ID NO:3)
Con NKES     (SEQ ID NO:4)
```

*FIG. 2A*

```
I2-2 MKRKIIAISLFLYIPLSNADNWESITKSYYTGFAMSKTVESKDQDGKTVRKEVITQADLT  60
Ike  -------------------------I--------K---P-------------          60
Con  MKRKIIAISLFLYIPLSNADNWESITKSYYTGFAXSKTVESKDXDGKXVRKEVITQADLT

I2-2 TACNDAKASAQDVFNQMKLTFSGIWPDSQFRLVTGDTCVYNGSPSEKTESWSIRAQVEGD 120
Ike  -------------N----I---L--T-N------------------G------------ 120
Con  TACNDAKASAQXVFNQXKLTXSGXWXDSQFRLVTGDTCVYNGSPXEKTESWSIRAQVEGD

I2-2 MQRSVPDEEPSEQTPEEICEAKPPIDGVFNNVSKGDEGGFYINYNGCEYEATGVTVCQND 180
Ike  I---------------------------------F------------------------ 180
Con  XQRSVPDEEPSEQTPEEICEAKPPIDGVFNNVXKGDEGGFYINYNGCEYEATGVTVCQND

I2-2 GTVCASSAWKPTGYVPESGESSSSPVKDGDTGGTGEGGSDTGGDTGGGDTGGGSTGGDTG 240
Ike  ----S-------------P----L----------------------------------- 240
Con  GTVCXSSAWKPTGYVPESGEXSSSPXKDGDTGGTGEGGSDTGGDTGGGDTGGGSTGGDTG

I2-2 GSTGGGSTGGGSTGGSTGKSLTKEDVTAAIHDASPSIGDAVKDSLTEDNDQNDNQKKADE 300
Ike  --S----S------------------V--------------------Y---------   300
Con  GSXGGGSXGGGSXGGSTGKSLTKEDVTAAIHXASPSIGDAVKDSLTEDNDQXDNQKKADE

I2-2 QSAKASASVSDAISDGMRGVGNFVDDLGGESSQYGIGNSEMDLSVSLAKGQLGIDLEGHG 360
Ike  ---------------------------F--------T-------------------R-- 360
Con  QSAKASASVSDAISDGMRGVGNFVDDXGGESSQYGXGNSEMDLSVSLAKGQLGIDXEGHG

I2-2 SAWESFLNDGALRPSIPSGHGCTDFVMFQGSVYQLDIGCDKLGDIKSVLSWVMYCLTFWY 420
Ike  -----------------T-----N---Y------IE------NDIKSVLSWVMYCLTFWY 420
Con  SAWESFLNDGALRPSIPXGHGCTXFVMXQGSVYQXXIGCDKLXDIKSVLSWVMYCLTFWY

I2-2 VFQSATSLLRKGEQ 434    (SEQ ID NO:5)
Ike  ----V---------  434    (SEQ ID NO:6)
Con  VFQSXTSLLRKGEQ         (SEQ ID NO:7)
```

FIG. 2B

```
MKKIIIALFFAPFFTHATTDAECLSKPAFDGTLSNVWKEGDSRYANFENCIYELSGIGIG   60
YDNDTSCNGHWTPVRAADGSGNGGDDNSSGGGSNGDSGNNSTPDTVTPGQTVNLPSDLST  120
LSIPANVVKSDSIGSQFSLYTNASCTMCSGYYLSNNADSIAIANITETVKADYNQPDMWF  180
EQTDSDGNHVKILQNSYKAVSYNVESKQSDVNNPTYINYSYSVNVKQVSYDTSNVCIMNW  240
ETFQNKCDASRAVLITDTVTPSYSRNITIQSNINYQGSNGSGGSGGSGGSGNDGGGTGNN  300
GNGTGDFDYVKMANANKDALTESFDLSALQADTGASLDGSVQGTLDSLSGFSDSIGGLVG  360
NGSAISGEFAGSSAAMNAIGEGDKSPLLDSLSFLKDGLFPALPEFKQCTPFVFAPGKEYE  420
FIIECKYIDMFKGIFAFILYFWTFVTVYDSFSGILRKGRG    (SEQ ID NO:8)     460
```

FIG. 2C

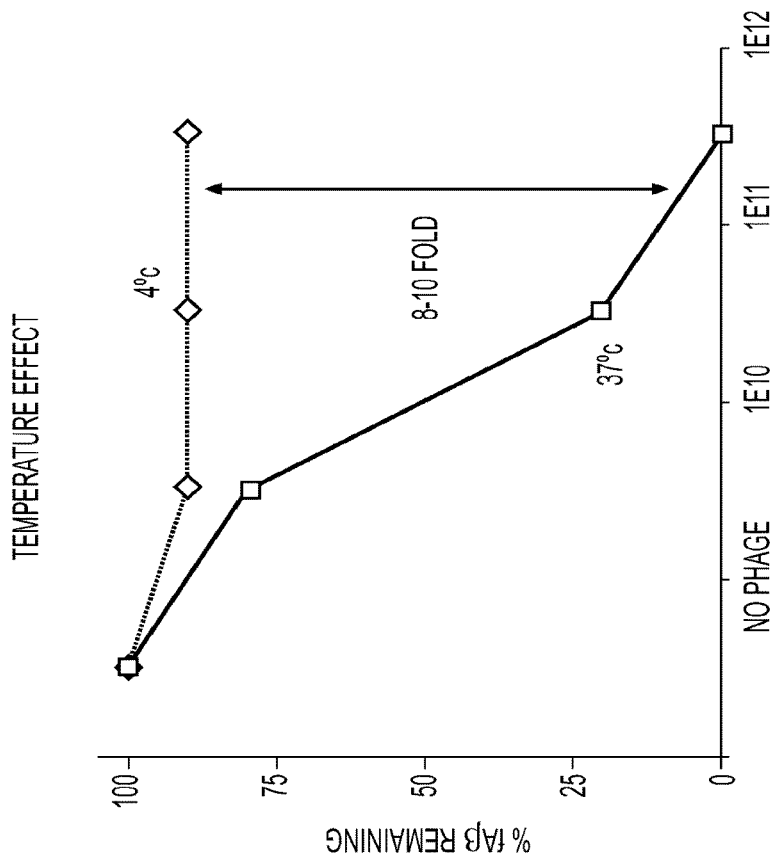
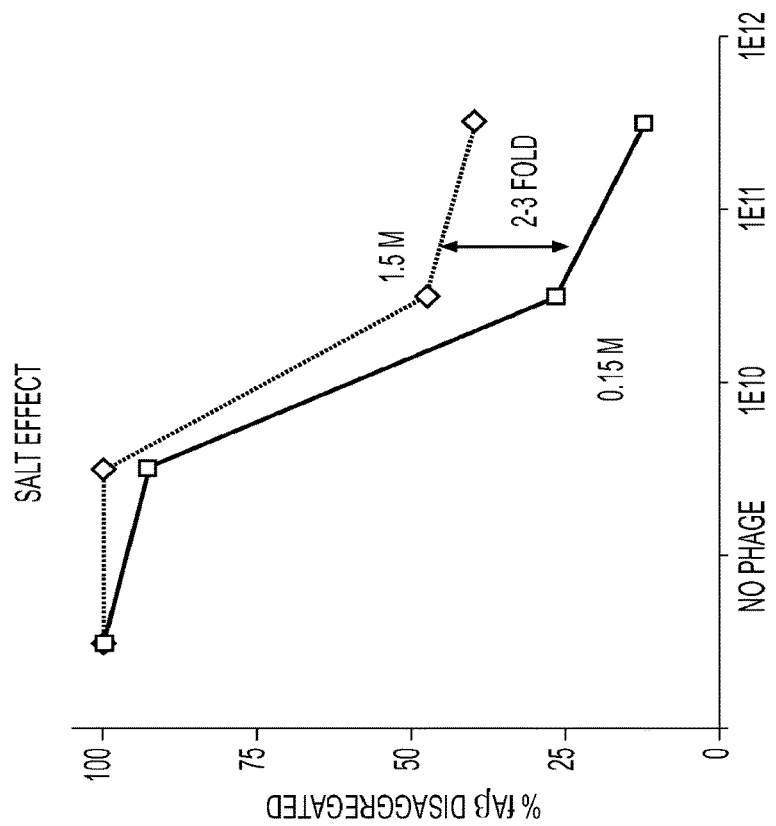

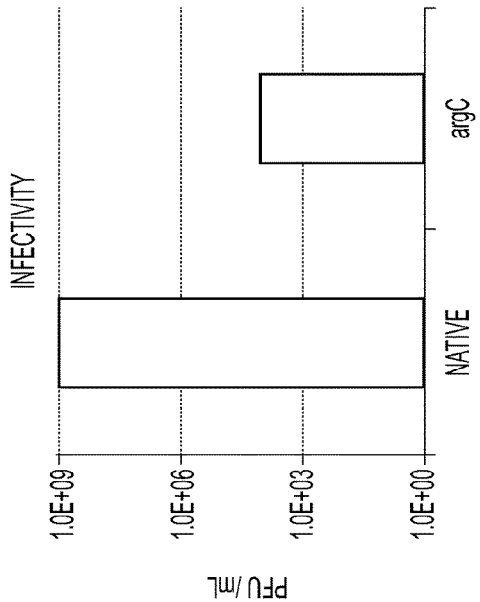
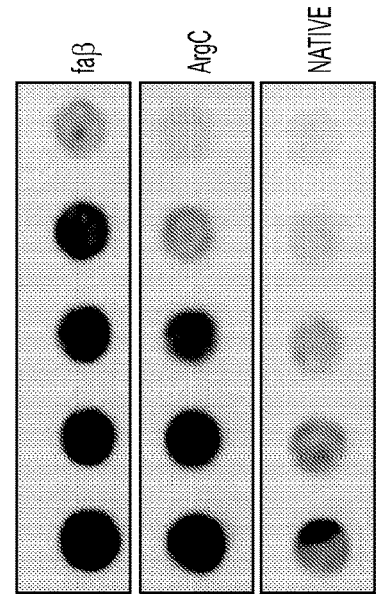
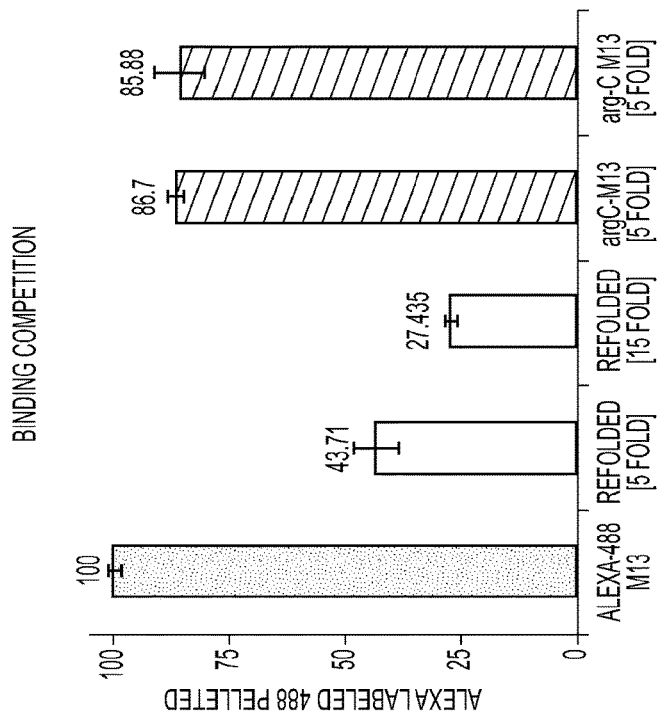

t=3 days t=0

MYRMQLLSCIALSLALVTNSMAETVESCLAKPHTENSFTNVWKDDKTL
DRYANYEGCLWNATGVVVCTGDETQCYGTWVPIGLAIPENEGGSEGG
GSEGGSEGGGTKPPEYGDTPIPGYTYINPLDGTYPPGTEQNPANPNP
SLEESQPLNTEMFQNRFRNRQGALTVYTGTFTQGTDPVKTYYQYTPV
SSKAMYDAYWNGKFRDCAFHSGFNEDPFVCEYQGQSSDLPQPPVNAGG
GSGGGSEGGGSEGGSEGGSEGGGSEGGSEGGSGAMVRSDKTHTC
PPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCK
VSNKALPAPIEKTISKAKGQPREPQVTLPPSREEMTKNQVSLTCLVK
GFYPSDIAVEWESNGQPENNYKTTPPVLDSDGSFFLYSKLTVDKSRWQ
QGNVFSCSVMHEALHNHYTQKSLSLSPGK (SEQ ID NO: 13)

*FIG. 25*

```
fd    TKPPEYGDTPIPGYTYINPLDGTYPPGTEQNPAN
f1    TKPPEYGDTPIPGYTYINPLDGTYPPGTEQNPAN
M13   TKPPEYGDTPIPGYTYINPLDGTYPPGTEQNPAN
Ike   S-PGEKTESWSIRAQVEGDIQRSVPD--EEPSEQ
I2-2  S-PSEKTESWSIRAQVEGDMQRSVPD--EEPSEQ
If1   STPDTIVTPGQTVNLPSDLSTLSIPANVVKSDSIG
      : *                       :   :

fd    PNPSLEE---------------SQPLNTFMFQNNRFRNRQGALTVYTGIVTQGTDPVKTY
f1    PNPSLEE---------------SQPLNTFMFQNNRFRNRQGALTVYTGIVTQGTDPVKTY
M13   PNPSLEE---------------SQPLNTFMFQNNRFRNRQGALTVYTGIVTQGTDPVKTY
Ike   TPEEICE---------------AKPPIDGVFNNVFKGDEGGFYINYNGCEYEATGVTVCQ
I2-2  TPEEICE---------------AKPPIDGVFNNVSKGDEGGFYINYNGCEYEATGVTVCQ
If1   SQFSLYTNASCTMCSGYYLSNNADSIATANTETVKADYNQPDMWFEQTDSDGNHVKIIQ
        :                    :     :            :  :

fd    YQYTPVSS------------KAMYDAYWNGKFRDCAFHSG-----FNEDPFVCEYQGQSSDL
f1    YQYTPVSS------------KAMYDAYWNGKFRDCAFHSG-----FNEDPFVCEYQGQSSDL
M13   YQYTPVSS------------KAMYDAYWNGKFRDCAFHSG-----FNEDPFVCEYQGQSSDL
Ike   NDGTVCSS------------SAWKPTGYVPESGEPSSSPL-----KDGDTGGTGEGGSDTGG
I2-2  NDGTVCAS------------SAWKPTGYVPESGESSSSPV-----KDGDTGGTGEGGSDTGG
If1   NSYKAVSYNVESKQSDVNPTYINYSYSVNVKQVSYDTSNVCIMNWETFQNKCDASRAVL
       :   :               :     :   :              :  :    :

fd    PQPPVNA  (SEQ ID NO:14)
f1    PQPPVNA  (SEQ ID NO:15)
M13   PQPPVNA  (SEQ ID NO:16)
Ike   DTGGGDT  (SEQ ID NO:17)
I2-2  DTGGGDI  (SEQ ID NO:18)
If1   ITDTVTP  (SEQ ID NO:19)
```

FIG. 26

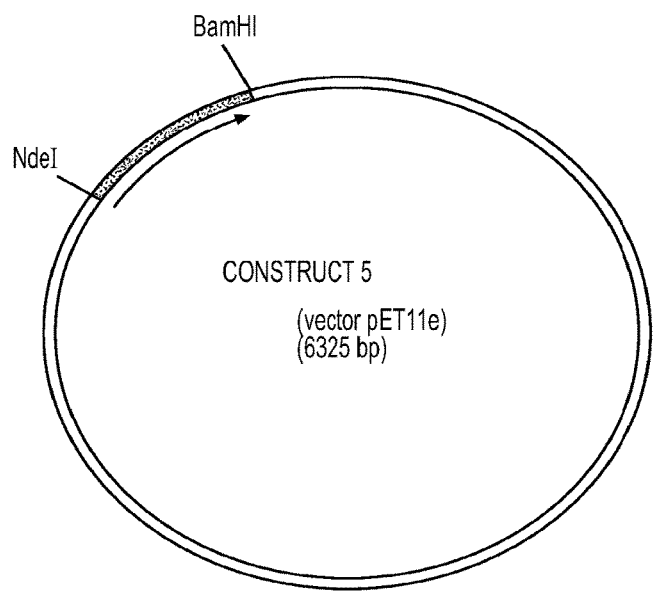

FIG. 27A atgGCTGAAACTGTTGAAAGTTGTTTAGCAAAATCCCATACAGAAAATTCATTTACTAACGTCTGGAAAGACGACAA
AACTTTAGATCGTTACGCTAACTATGAGGGCTGTCTGTGGAATGCTACAGGCGTTGTAGTTTGTACTGGTGACGAAA
CTCAGTGTTACGGTACATGGGTTCCTATTGGGCTTGCTATCCCTGAAAATGAGGGTGGTGGCTCTGAGGGTGGCGGT
TCTGAGGGTGGCGGTTCTGAGGGTGGCGGTACTAAACCTCCTGAGTACGGTGATACACCTATTCCGGGCTATACTTA
TATCAACCCTCTCGACGGCACTTATCCGCCTGGTACTGAGCAAAACCCCGCTAATCCTAATCCTTCTCTTGAGGAGT
CTCAGCCTCTTAATACTTTCATGTTTCAGAATAATAGGTTCCGAAATAGGCAGGGGGCATTAACTGTTTATACGGGCA
CTGTTACTCAAGGCACTGACCCCGTTAAAACTTATTACCAGTACACTCCTGTATCATCAAAAGCCATGTATGACGCTT
ACTGGAACGGTAAATTCAGAGACTGCGCTTTCCATTCTGGCTTTAATGAGGATTTATTTGTTTGTGAATATCAAGGCC
AATCGTCTGACCTGCCTCAACCTCCTGTCAATGCTCCGTCCgggcatcatcatcatcatcattaa(SEQIDNO:23)

FIG. 27B

FIG. 27C (SEQ ID NO:24)

1. Aβ 10μM
2. Aβ 10μm + 5μM CONSTRUCT 6
3. Aβ 10μm + 2μM CONSTRUCT 6
4. Aβ 10μm TIME=0

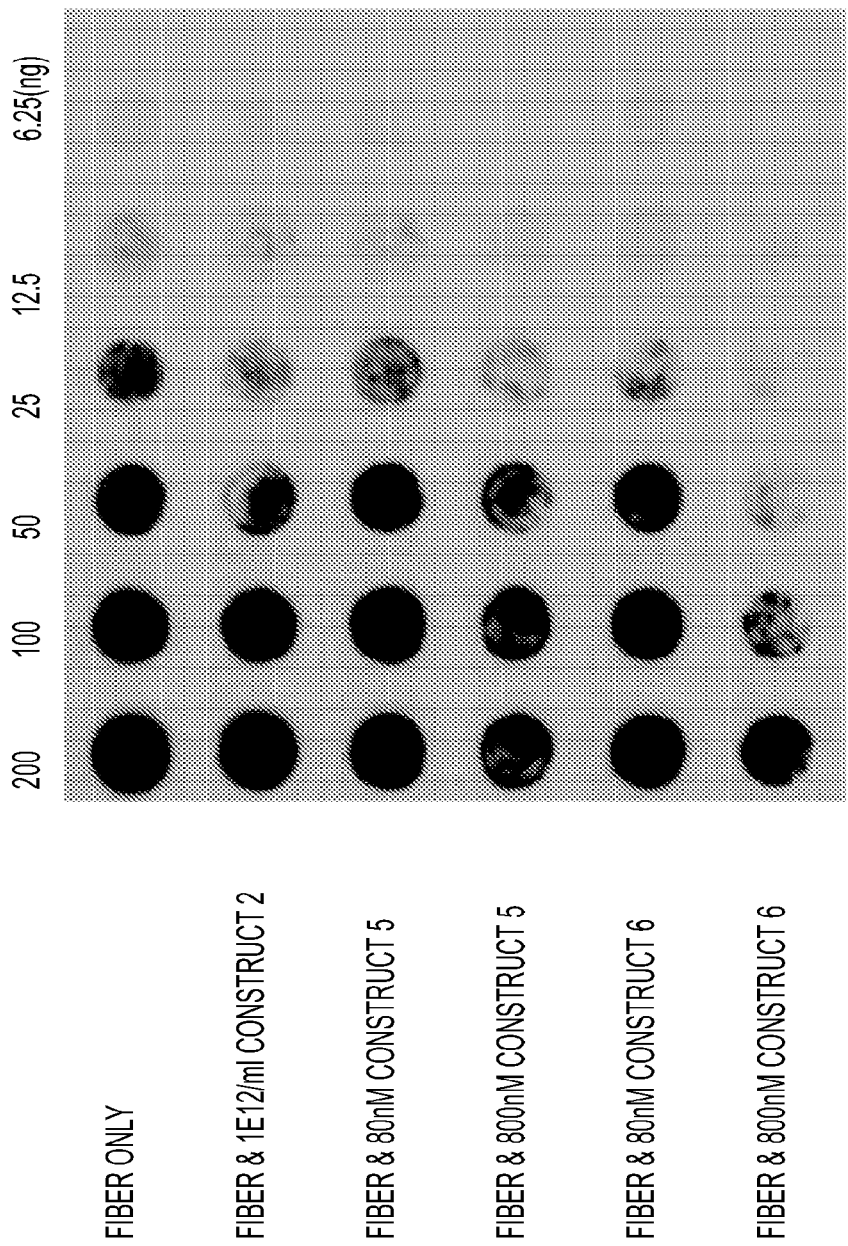

1. Aβ42 1μM
2. Aβ42 1μM T=0
3. Aβ42 + CONSTRUCT 6 0.5μM
4. Aβ + CONSTRUCT 6 0.2μM
5. Aβ + CONSTRUCT 6 0.05μM
6. Aβ + CONSTRUCT 6 1μM
7. Aβ + CONSTRUCT 6 0.1μM

BACTERIOPHAGE GENE 3 PROTEIN COMPOSITIONS AND USE AS AMYLOID BINDING AGENTS

This is a division of U.S. application Ser. No. 14/361,157, filed May 28, 2014, which is a national stage filing under 35 U.S.C. § 371 of International Application No. PCT/US2012/066793 filed Nov. 28, 2012, and claims the benefit of U.S. provisional application No. 61/564,602 filed Nov. 29, 2011, U.S. provisional application No. 61/708,709, Oct. 2, 2012, and U.S. provisional application No. 61/730,316 filed Nov. 27, 2012, all of which are incorporated herein by reference.

The invention relates to pharmaceutical compositions comprising the filamentous bacteriophage g3p protein, amyloid-binding fragments of g3p, and amyloid-binding mutants and variants of g3p, and to the use of such compositions as a therapeutic to decrease amyloid load associated with diseases, such as systemic and peripheral amyloid diseases, neurodegenerative diseases including neurodegenerative tauopathies, and transmissible spongiform encephalopathies (prion-associated diseases). Also encompassed is the use of those compositions to prevent the accumulation of amyloid load associated with these diseases, and the use of those compositions as diagnostics to detect amyloid and thus, diagnose such diseases.

Filamentous bacteriophage M13, and related filamentous phage, have shown utility in animal models of protein misfolding disease, and therefore represent a potential therapeutic class for protein misfolding diseases. See United States patent publication US 2011/0142803, incorporated by reference herein in its entirety. In particular, it has been discovered that filamentous bacteriophage have the ability to mediate clearance of amyloid that have already formed in the brain. See, e.g., WO2006083795 and WO2010060073, incorporated by reference herein in their entirety.

Amyloid forming diseases are characterized by neuronal degeneration and the presence of misfolded, aggregated proteins in the brain. These misfolded and aggregated proteins vary in different diseases, but in most cases, they have a cross-beta-pleated sheet structure that binds Congo Red dye and shows apple green birefringence. Removal of amyloid is expected to reduce, slow the progression of, or even to reverse the symptoms associated with a variety of diseases characterized by amyloid.

Potential therapeutic approaches to prevent and/or reverse the pathology and/or symptoms associated with amyloid forming diseases include, for example, inhibiting amyloid formation, promoting amyloid clearance, and inhibiting amyloid aggregation. See, for example, Aguzzi & O-Connor, Nature Review Drug Discovery (2010) 9:237-48. Removing and/or preventing the formation of toxic oligomers may also be beneficial in the treatment and prevention of amyloid forming diseases. Id.

Neurodegenerative diseases known to be associated with misfolded and/or aggregated proteins include Alzheimer's disease, Parkinson's disease, prion diseases, neurodegenerative tauopathies, amyotrophic lateral sclerosis (ALS), spinocerebellar ataxia (SCA1), (SCA3), (SCA6), (SCA7), Huntington disease, entatorubral-pallidoluysian atrophy, spinal and bulbar muscular atrophy, hereditary cerebral amyloid angiopathy, familial amyloidosis, frontotemporal lobar degeneration (FTLD) including frontotemporal lobe dementia, British/Danish dementia, and familial encephalopathy. Other diseases involve misfolded and/or aggregated proteins in the periphery—the so called peripheral amyloidoses. See, for example, Chiti & Dobson, Annu Rev Biochem (2006) 75:333-66; and Josephs et al., Acta Neuropathol (2011) 122:137-153. There is a great need to prevent and/or reduce amyloid aggregate formation (i.e., misfolded and/or aggregated proteins) to treat or reduce the symptoms or severity of these diseases.

Recently, the National Institute on Aging and the Alzheimer's Association published criteria for diagnosing "all-cause" and Alzheimer's Disease dementia. See, McKhann et al., Alzheimer's & Dementia, (2011) 7(3):263-9. Based on this guidance, "all cause" dementia is diagnosed when behavioral or cognitive symptoms satisfy five tests, which include, for example, the interference with the ability to function at work or at usual activities, and a decline from previous levels of functioning and performing. The tests involve a combination of history-taking and objective cognitive assessment. As described herein, the discovery that filamentous bacteriophage g3p protein, amyloid-binding fragments of g3p, and amyloid-binding mutants and variants of g3p bind amyloid provides complementary methods to diagnose any disease or dementia resulting from the formation of amyloid, including "all cause" and Alzheimer's dementia.

Filamentous bacteriophage are a group of structurally related viruses that infect bacterial cells, and contain a circular single-stranded DNA genome. They do not kill their host during productive infection. Rasched and Oberer, Microbiol Rev (1986) 50:401-427. Examples of filamentous bacteriophage include phage of the Ff family (e.g., M13, f1, and fd). The nucleotide sequence of fd has been known since 1978. Beck et al., Nucleic Acids Research (1978) 5(12):4495-4503. The full sequence of M13 was published in 1980. van Wezenbeek et al., Gene (1980) 11:129-148. Phage f1 was sequenced by 1982. Hill and Petersen, J. Virol. (1982) 44(1):32-46. The f1 genome comprises 6407 nucleotides, one less than phage fd. It differs from the fd sequence by 186 nucleotides (including one nucleotide deletion), leading to 12 amino acid differences between the proteins of phages f1 and fd. The f1 sequence differs from that of M13 by 52 nucleotides, resulting in 5 amino acid differences between the corresponding proteins. Id. The DNA sequences of M13 and fd vary at 192 (3%) nucleotides, yet only 12 of these differences result in a change in the corresponding amino acid sequence (6.25%). van Wezenbeek et al., Gene (1980) 11:129-148.

The structure of filamentous phage is well established and is reviewed, for example, in Marvin, Curr. Opin. in Struct. Biol. (1998) 8:150-158; Rasched and Oberer, Microbiological Reviews (1986) 50(4):401-427. Filamentous phage have a "coat" that comprises thousands of copies of a major capsid protein encoded by gene 8 (g8p, p8 or pVIII). It is the assembled g8p-DNA complex that forms the characteristic filamentous shape of the phage. Minor coat proteins, i.e., those that are present in only a few (3-5) copies, are located at the ends of the filament. One of these tip proteins, g3p (also known as p3 or pIII), is necessary for bacterial host binding and initiates infection.

M13 phage has a mature g3p of 406 amino acids. GenBank Ref Seq NP_510891.1 provides a reference sequence that includes the 18 residue amino-terminal signal sequence. Variants that have amino acid differences as compared to published sequences are common. Filamentous phage of the I-family have g3p that differs from Ff family members, but even between families g3p is still highly conserved. Stassen et al., J Mol Evol (1992) 34:141-52.

A crystal structure is available for g3p. Lubkowski et al., Structure (1998) 7(6) 711-722. The protein comprises 3 folded domains separated by flexible glycine-rich linker sequences. There are two amino-terminal domains, N1 and N2 comprising 262 amino acids, that interact to form an N1-N2 complex. The carboxy-terminal (CT, also called N3) domain is 146 amino acids and it serves to anchor g3p in the phage particle by hydrophobic interactions with g8p. Marvin, Current Opin. in Structural Biology (1998) 8:150-158. A publically available ribbon structure prepared using the N1-N2 domain fusion protein 2g3p of Holliger, J Mol. Biol. (1999) 288(4):649-57 is presented in FIG. 1.

Unlike most proteins, unfolding of the N1 and N2 domains from the latent "locked" form is required for g3p to acquire its native biological activity. Eckert & Schmid, J. Mol. Biol. (2007) 373:452-461. In the initial step in infection, N2 binds the bacterial F-pilus via residues on the outer rim of N2. Deng & Perham, 2002. This initial binding by N2 "unlocks" g3p by "opening" the N1-N2 complex, permitting N1 to then bind the co-receptor TolA. In an N1-N2 fragment of g3p, the thermal transition for the initial unlocking step in which N2 unfolds occurs at a melting temperature ($T_M$) of 48.1° C. Part of the process involves an isomerization at the Gln212-Pro213 peptide bond. Pro213 converting is trans in the unlocked state. N1 remains stably folded until the second step, which occurs at a $T_M$ of 60.2° C. Reviewed in Eckert & Schmid, 2007.

Mutations in the N1-N2 fragment have been used to study the stability and infectivity of various mutants. Eckert & Schmid, 2007. One variant, designated "3A" impaired pilus binding and decreased the stability of the N2 domain. For this mutation, the $T_M$ is decreased to 42.6° C. 3A carries the following mutations: W181A, F190A, and F194A. Another mutant in N2, G153D, destabilized N2, decreasing $T_M$ to 44.4° C. A Q129H mutant stabilized N2, increasing the $T_M$ to 51.4° C. The IY variant contains the mutations T101I and D209Y in the hinge and increases the stability of the N1-N2 fragment ($T_M$=56.5° C.). IHY contains the mutations T101I, Q129H, and D209Y ($T_M$=60.1° C.). IIHY contains the mutations T131, T101I, Q129H, and D209Y ($T_M$=61.8° C.). Both the Q129Y and T131 mutations are stabilizing, and adding these mutations further increases the melting temperature, $T_M$. Phage infectivity varied inversely with the strength of the domain interactions within g3p. Eckert & Schmid, 2007. Deletion of the N2 domain (phage fd(ΔN2)) increased the infectivity by removing the blocking effect of the N2 domain on N1-binding of TolA. Id.

The invention is based in part on the discovery that g3p also mediates binding of the filamentous phage to amyloid in a manner analogous to the process by which phage infect bacteria. U.S. Pat. No. 7,867,487 postulated that the mechanism underlying the therapeutic efficacy of phage in disaggregating amyloid reported in that patent was that the phage's long, thin, structure, might enable it to organize along the amyloid fibers. In addition, it was proposed that the high alpha helical content present in g8p, the major coat protein, might interfere with the beta sheet structure of amyloid. That mechanism is consistent with the patent's report that nanomolar amounts of phage can disaggregate micromolar quantities of β-amyloid, which would suggest a high copy component of the phage, g8p, is mediating the effect. It is also consistent with the report in US20110182948 that tobacco mosaic virus, which has a similar structure to filamentous phage, can cause disaggregation. Thus this earlier work suggested that either the intact structure (a long filament with many alpha helices) was important for therapeutic effect or that, if a particular coat protein was important, it was a protein that was highly represented on the phage coat, such as g8p. None of this earlier work provided any suggestion that an isolated component of bacteriophage, as opposed to intact phage, could bind to amyloid and/or cause its disaggregation. Moreover, there was never any suggestion that a minor coat protein of filamentous bacteriophage played a role in its ability to bind to and disaggregate amyloid.

However, this disclosure provides evidence of an alternative (although not necessarily mutually exclusive) mechanism of action. The inventor has found that phage g3p directly binds amyloid fibers and that phage-mediated disaggregation is dependent upon this initial binding step. The inventor's recognition that g3p is responsible for filamentous phage-mediated amyloid binding provides a mechanism for bacteriophage therapeutic efficacy, as well as provides a basis for new classes of therapeutics and diagnostics.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIGS. 2A-2C present alignments of g3p's from different sources. FIG. 2A is an alignment of g3p from phage M13 (SEQ ID NO: 1), Fd (SEQ ID NO:2), and F1 (SEQ ID NO: 3), including a consensus sequence (SEQ ID NO: 4). FIG. 2B shows an alignment of g3p from phage 12-2 (SEQ ID NO: 5) and Ike (SEQ ID NO: 6), along with a consensus sequence between 12-2 and Ike (SEQ ID NO: 7). FIG. 2C presents the amino acid sequence of g3p from phage If (SEQ ID NO: 8).

FIG. 4A shows a direct binding assay for two phage doses ($10^{11}$/mL and $10^{12}$/mL) with increasing molar amounts of fAβ42. FIG. 4B is a binding competition study and provides an alternate way to determine the $K_D$ for M13 binding. Construct 1 was used.

FIGS. 7A and 7B show the effect of varying individual assay parameters in the ThT disaggregation assay. FIG. 7A presents disaggregation percentages in the presence of two salt concentrations (0.15 M and 1.5 M). FIG. 7B presents percentages of fAβ remaining at two temperatures (4° C. and 37° C.). Construct 1 was used.

In FIG. 8A, M13 binding is reported using incubation temperatures from 18° C. to 58° C. for 3 hours. FIG. 8B shows binding kinetics for incubations at 37° C. vs. 50° C.

FIGS. 9A-9C show the effect of proteolytic removal of g3p on phage-amyloid interactions. The protease Arg C was used to clip g3p from M13 phage (M13Δg3p). FIG. 9A presents the results of an Aβ binding competition study using M13Δg3p phage compared to native (treated identically to the ArgC-treated phage but without protease treatment) phage. FIG. 9B shows the effect of Arg C treatment on infectivity of the M13Δg3p phage compared to native phage. FIG. 9C compares ArgC treated phage to native phage in the disaggregation assay.

FIG. 10B shows a repeat of the competition assay.

FIG. 14A indicates that binding is dose-dependant.

Figure 23:
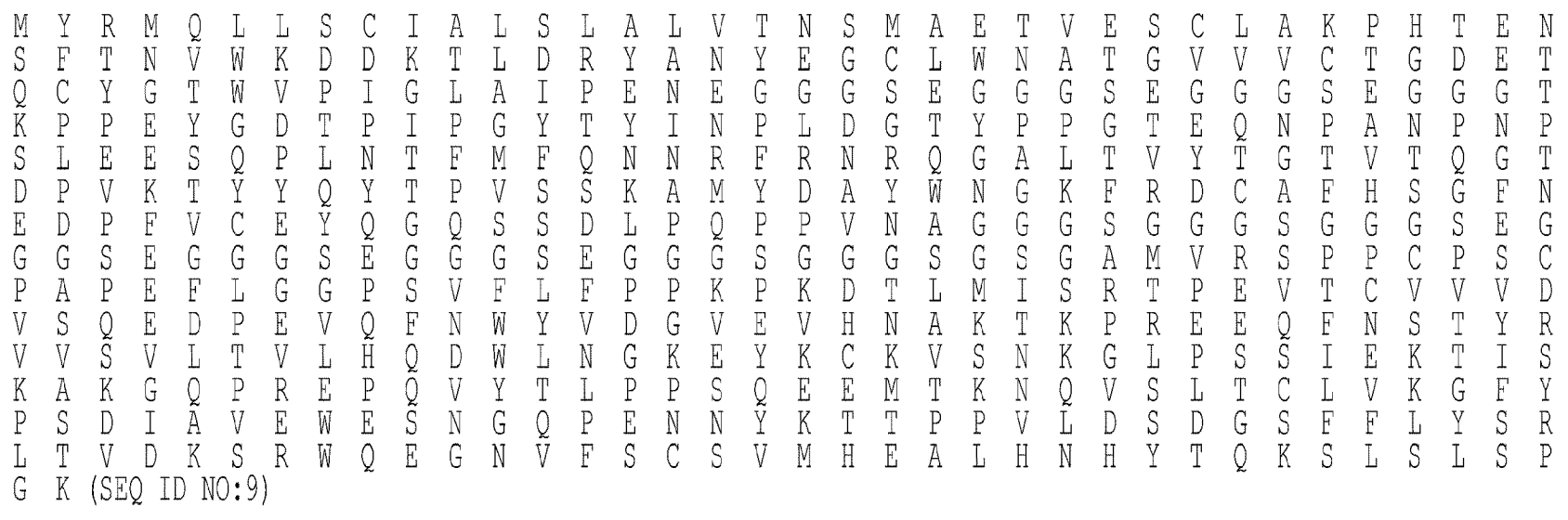

FIG. 23 shows the amino acid sequence of one rs-g3p (N1N2)-hIgG4-Fc construct "Construct 4" (SEQ ID NO:9). The N1N2 region of "Construct 4" is derived from the N1N2 region of "Construct 1" (SEQ ID NO:10).

FIG. 24 shows the amino acid sequence of another rs-g3p(N1N2)-hIgG4-Fc construct "Construct 5" (SEQ ID NO:11). The N1N2 region of "Construct 5" is derived from the N1N2 region of "Construct 2" (SEQ ID NO:12).

FIG. 25 shows the amino acid sequence of one rs-g3p (N1N2)-hIgG1-Fc construct "Construct 6" (SEQ ID NO:13). The N1N2 region of "Construct 6" is derived from the N1N2 region of "Construct 2".

FIG. 26 shows the amino acid sequence alignment of N2 from: fd (SEQ ID NO:14), f1 (SEQ ID NO:15), M13 (SEQ ID NO:16), Ike (SEQ ID NO:17), 12-2 (SEQ ID NO:18), and If1 (SEQ ID NO:19). An asterisk "*" indicates positions which have a single, fully conserved residue. A colon ":" indicates conservation between groups of strongly similar properties that score greater than 0.5 in the Gonnet PAM 250 matrix. A period "." indicates conservation between groups of weakly similar properties that score equal to or less than 0.5 in the Gonnet PAM 250 matrix.

FIG. 27A shows a schematic of Construct 5. FIG. 27B shows the DNA sequence of the g3p portion of Construct 5 (SEQ ID NO:23). FIG. 27C shows the amino acid sequence of the g3p portion of Construct 5 (SEQ ID NO:24).

FIG. 30A shows a "native" agarose gel made without SDS. The samples were run in TEA buffer without SDS and not boiled. The results indicate that Construct 6 is capable of inhibiting the assembly of fAβ42. FIG. 30B presents a Tht fluorescence assay used to measure the amyloid present in a given sample. 10 µM of Aβ42 monomers were incubated in the presence or absence of 2 concentrations of rs-g3p(N1N2)-hIgG1-Fc (Construct 6) at 37° C. for 1 day. The amount of fibers formed at the end of day 1 was measured by quantitating the bound ThT fluorescence. rs-g3p(N1N2)-hIgG1-Fc (Construct 6) potently inhibits formation of Aβ42 fibers. The figure also indicates that inhibition of fiber formation with Construct 6 is dose-dependent.

FIG. 31A shows the ellipticity versus wavelength for Aβ42 at T=0, T=24 hours, and T=48 hours. FIG. 31B shows ellipticity versus wavelength for Aβ42 plus Construct 3 at T=0, T=24 hours, and T=48 hours. FIG. 31C shows a representative ThT assay where the amount of fibers formed between 24 and 48 hours was measured by quantitating the bound ThT fluorescence. Construct 3 potently inhibits formation of Aβ42 fibers. FIG. 31D shows ellipticity versus wavelength for Construct 3 at T=0, T=24 hours, and T=48 hours. Taken together, these data confirm the ability of Construct 3 to inhibit Aβ42 assembly.

FIG. 33 shows a filter trap assay comparing six concentrations of A342 fibers plus or minus $1 \times 10^{12}$/ml M13 (Construct 2); 80 nm and 800 nM rs-g3p(N1N2)-hIgG4-Fc construct (Construct 5); and 80 nm and 800 nM of rs-g3p (N1N2)-hIgG1-Fc (Construct 6). Aβ42 fibers were incubated with Constructs 2, 5, and 6 at 37° C. for 3 days, followed by filter retardation. The filter was probed by mAb 6E10 (1:15000), which recognizes Aβ42 fibers trapped on the filter. 800 nM of Construct 5 or Construct 6 equals $5 \times 10^{14}$/ml Construct 2 by molecular molarity. The results indicate that Constructs 2, 5, and 6 potently disaggregate β-amyloid fibers.

FIG. 36A presents the results of a representative ThT assay showing the ability of Construct 6 to disaggregate ftau. FIG. 36B shows another representative experiment confirming the ability of Construct 6 to disaggregate tau. FIGS. 36A and 36B also show that disaggregation of ftau by Construct 6 is dose dependent.

FIG. 37A shows an SDS PAGE of the samples. FIG. 37B shows the results from one representative experiment. FIG. 37C shows the results from another representative experiment. FIG. 37D summarizes the results.

FIG. 39A shows biochemically resolved undigested and PK-digested $N2a22L^{Sc}$ cell lysates following treatment with Construct 6 and IgG. A significant reduction in $PrP^{Sc}$ levels is clearly observed in cells treated with increasing concentrations of Construct 6. An approximately 50% reduction in $PrP^{Sc}$ levels is achieved with treatment of ~0.08 ug/ml Construct 6. Treatment with 10 ug/ml Construct 6 reduces $PrP^{Sc}$ levels to 5.725%, p<0.0001. No marked changes in $PrP^{Sc}$ levels were observed in $N2A22L^{sc}$ cells treated with 1 ug/ml murine IgG. For FIG. 39B, the X-ray films were subsequently digitized and initially normalized to the effect in IgG treated $N2a22L^{Sc}$ cells from the same passage which was considered to be 100%. The densitometry data from PK-digested blots was then analyzed relative to the equivalently blotted undigested lysates and expressed as a percent change $PrP^{Sc}/PrPc$. Data represents n=4.

DESCRIPTION OF EMBODIMENTS

Figure 1:
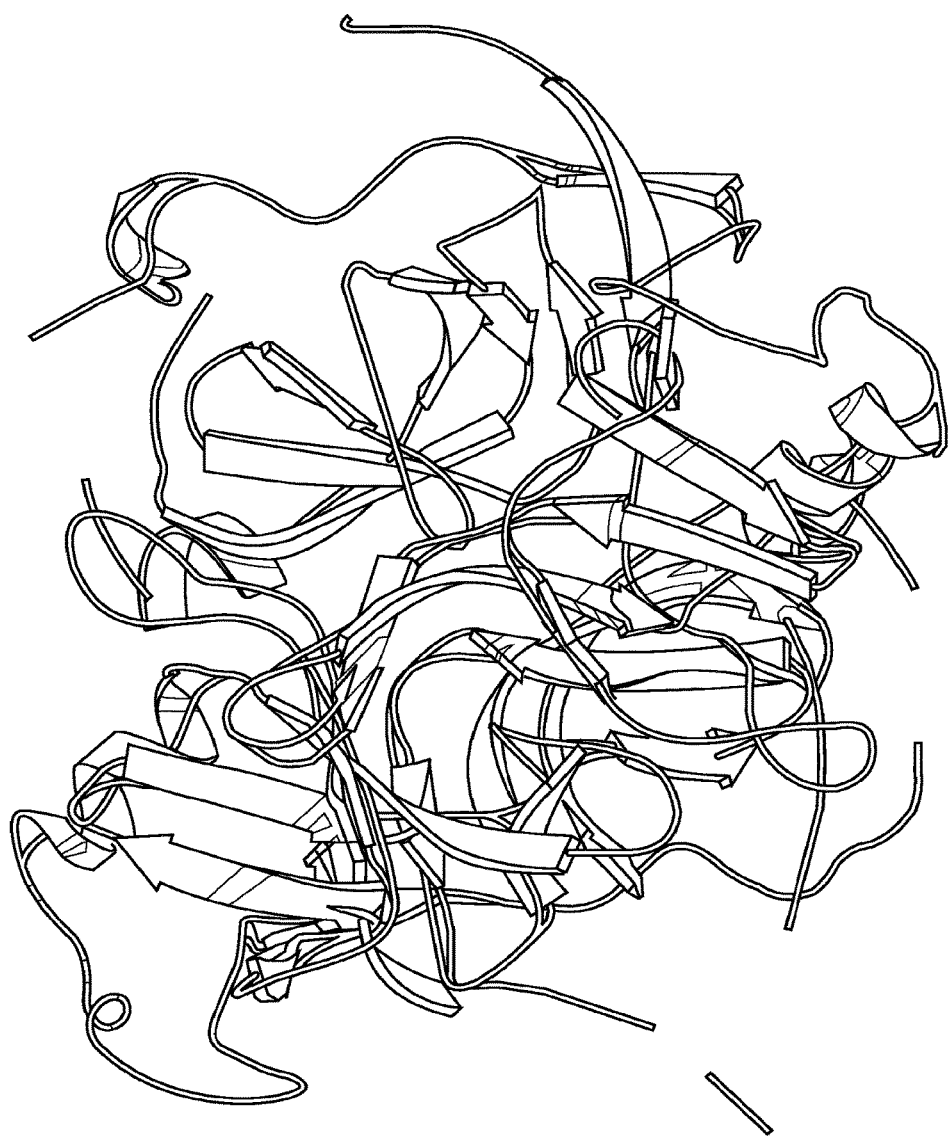
FIG. 1 presents a ribbon structure of the N1 and N2 domains of g3p, and the hinge.

The invention is based, in part, on the inventor's recognition of the role of the gene 3 protein ("g3p," also known as "p3" or "pIII") in mediating amyloid binding and disaggregation of amyloid aggregates. The invention is also based on the inventors' identification of a minimal sequence of g3p required for binding to amyloid.

Thus, in certain embodiments, the invention provides molecules, in particular polypeptides, that comprise minimal consensus amyloid binding sequences derived from g3p. In one aspect of these embodiments, the molecules are soluble. In another aspect of these embodiments, the molecules disaggregate and/or prevent the aggregation of amyloid (e.g., amyloid plaque). In another aspect of these embodiments, the molecules are fusion proteins. In a more specific aspect of these embodiments, the molecules are fusion proteins additionally comprising an amino acid sequence of an immunoglobulin chain. In an even more specific aspect of these embodiments, the molecules are fusion proteins additionally comprising an amino acid sequence of an immunoglobulin G (e.g., IgG) or immunoglobulin M (e.g., IgM) chain. In still another aspect of these embodiments, the molecule comprises the N2 domain of g3p. In a more specific aspect of these embodiments, the molecule comprises the N1-N2 domain of g3p. In still another aspect of these embodiments, the molecule comprises a full length g3p. In yet another aspect, the molecule is a polypeptide that is a fragment, mutant, or variant of any of the foregoing.

In other aspects, the invention provides molecules that bind to TolA, such as TolA inhibitor molecules, in particular polypeptides, that comprise minimal consensus amyloid binding sequences. The TolA binding molecules and/or TolA inhibitors of the present invention bind to, depolymerize, prevent the aggregation of, and disaggregate amyloid. The TolA binding molecules and/or TolA inhibitor molecules include fusion proteins. In certain embodiments the TolA binding molecule and/or TolA inhibitor molecule is a colicin or amyloid binding fragment of a colicin. In certain embodiments the colicin is a Group A colicin. See, e.g., Cascales et al., Microbiol. Mol. Biol. Rev. (2007) 71(1): 158-229. The TolA binding molecules and TolA inhibitor molecules of the invention are useful therapeutics to decrease amyloid load associated with diseases, such as systemic and peripheral amyloid diseases, neurodegenerative diseases including neurodegenerative tauopathies, and transmissible spongiform encephalopathies (prion-associated diseases). Also encompassed is the use of those compositions to prevent the accumulation of amyloid load associated with these diseases, and the use of those compositions as diagnostics to detect amyloid and thus, diagnose such diseases.

In another embodiment, the invention provides filamentous bacteriophage that have been modified to overexpress g3p as compared to wild type phage, to express an amyloid binding fragment of g3p, an amyloid binding mutant or variant form of g3p, or an amyloid binding fusion protein comprising g3p.

The invention provides compositions of matter and/or pharmaceutical compositions of any of the foregoing molecules or bacteriophage, as well as their use to bind to, disaggregate, and prevent aggregation of amyloid, and to their use to detect amyloid deposits and diagnose diseases and disorders characterized by amyloid.

Definitions

The term "g3p" when used alone or in terms such as "g3p-derived" refers to any wild type or recombinant filamentous phage g3p protein (including fragments, variants, and mutants of g3p). The term should not be construed as limited to any particular filamentous bacteriophage g3p. By way of example, the term "g3p" includes SEQ ID NO: 1 and the related proteins shown in FIG. 2.

The term "filamentous bacteriophage" includes both wild type filamentous bacteriophage, and recombinant filamentous bacteriophage. In the present application, "filamentous bacteriophage" may also be referred to as "bacteriophage," "phage," or "M13."

The term "wild-type filamentous bacteriophage" as used herein refers to filamentous phage found in nature, filamentous phage that have been indicated as "wild-type" in any nucleotide or amino acid sequence database, filamentous bacteriophage that are commercially available and characterized as "wild-type," and filamentous bacteriophage that have acquired non-recombinant mutations relative to any of the foregoing through passaging.

The term "domain" means a region of a polypeptide (including proteins) having some distinctive physical feature or role including for example an independently folded structure composed of one section of a polypeptide chain. A domain may contain the sequence of the distinctive physical feature of the polypeptide or it may contain a fragment of the physical feature which retains its binding characteristics (i.e., it can bind to a second domain). A domain may be associated with another domain. In other words, a first domain may naturally bind to a second domain. For example, the g3p N2 domain binds F-pili and the g3p N1 domain binds TolA.

The terms "amyloid," "amyloid fibrils," and "amyloid fibers," as used herein are generic terms for a tertiary structure that is formed by aggregation of any of several different proteins and that consists of an ordered arrangement of β sheets stacked perpendicular to a fiber axis. Sunde et al., J. Mol. Biol. (1997) 273:729-39. One exemplary amyloid is the aggregate of amyloid-β formed in Alzheimer's disease, which is composed of beta-amyloid peptide "βA," which are 39-43 amino acid internal fragments cleaved from the human amyloid precursor protein (hAPP). There are short forms, such as Aβ40, and long forms, such as the more fibrillogenic Aβ isoform, Aβ42. Other exemplary amyloid proteins include misfolded α-synuclein (associated with Parkinson's disease), huntingtin (associated with Huntington's disease), tau (associated with Alzheimer's Disease), and the abnormal conformation of the prion protein, $PrP^{Sc}$. Additional examples are provided throughout the description and are known to those of skill in the art (see, e.g., Aguzzi (2010), and Eichner and Radford, Mol. Cell (2011) 43:8-18). Thus, unless a protein or peptide is specified, use of the terms "amyloid," "amyloid fibrils," or "amyloid fibers" should not be construed as limited to any particular protein or disease.

The term "beta amyloid peptide" is synonymous with "β-amyloid peptide," "βAP," "βA," and "Aβ" All of these terms refer to an amyloid forming peptide derived from the human amyloid precursor protein (hAPP).

A phage, protein, fusion protein, fusion protein domain, or a mutant, fragment, or variant of the foregoing that "binds amyloid fibrils" or that is "amyloid-binding" is one that is positive in an amyloid binding assay. Amyloid binding can be detected in vitro using a direct binding assay such as surface plasmon resonance (SPR), in which case it will generally bind amyloid with a Kd of at least $10^{-8}$ M, $10^{-9}$ M, $10^{-10}$ M, or $10^{-11}$ M. Alternatively, amyloid binding can be detected using the fAβ42 binding assay described in the examples. Amyloid-binding fragments, variants, and mutants of g3p may also be identified by their co-localization to amyloid when injected into a transgenic mouse model of any a protein misfolding disease.

Any of the products or compositions of the invention described as "disaggregating" or "mediating disaggregation" reduce aggregates that have already formed. Disaggregation can be measured by the filter trap assay. Wanker et al., Methods Enzymol (1999) 309:375-86. The filter trap assay is described herein and can be used both to detect aggregates and to monitor disaggregation mediated by compositions of the invention. Disaggregation is detected as decreased retention of amyloid on the filter, as shown by a decrease in staining, in the presence of increasing concentrations of the disaggregating agent.

As used herein, a composition that "reduces amyloid" does one or more of the following: inhibits amyloid formation, causes amyloid disaggregation, promotes amyloid clearance, inhibits amyloid aggregation, blocks and/or prevents the formation of toxic amyloid oligomers, and/or promotes the clearance of toxic amyloid oligomers.

Any of the products or compositions of the invention described as "protecting neurons from amyloid damage" prevent the accumulation of new amyloid and/or prevent the formation of toxic amyloid oligomers. Products or compositions of the invention described as "protecting neurons from amyloid damage" may be taken prophylactically. Whether or not a product or composition protects neurons from amyloid damage may be measured by the neuronal cell culture cytotoxicity assay described herein.

As used herein, "PrP protein," "PrP," and "prion," refer to polypeptides that are capable under appropriate conditions, of inducing the formation of aggregates responsible for protein misfolding diseases. For example, normal cellular prion protein ($PrP^c$) is converted under such conditions into the corresponding scrapie isoform ($PrP^{Sc}$) which is responsible for diseases such as, but not limited to, bovine spongiform encephalopathy (BSE), or mad cow disease, feline spongiform encephalopathy of cats, kuru, Creutzfeldt-Jakob Disease (CJD), Gerstmann-Straussler-Scheinker disease (GSS), and fatal familial insomnia (FFI).

The term "variant" as used herein in conjunction with a bacteriophage, protein, polypeptide or amino acid sequence (e.g., a g3p variant or a variant of an amyloid binding fragment of g3p), refers to a corresponding substance that contains at least one amino acid difference (substitution, insertion or deletion) as compared to the reference substance. In certain embodiments a "variant" has high amino acid sequence homology and/or conservative amino acid substitutions, deletions and/or insertions as compared to the reference sequence. In some embodiments, a variant has no more than 75, 50, 40, 30, 25, 20, 15, 12, 10, 9, 8, 7, 6, 5, 4, 3, 2, 1 amino acid differences as compared to the reference sequence. A "conservative substitution" refers to the replacement of a first amino acid by a second amino acid that does not substantially alter the chemical, physical and/or functional properties of the g3p protein or amyloid binding fragment of g3p (e.g., the g3p protein or amyloid binding fragment retains the same charge, structure, polarity, hydrophobicity/hydrophilicity, and/or preserves functions such as the ability to recognize, bind to, and/or reduce amyloid). Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine.

The term "mutant" (e.g., "mutant g3p" or "mutant amyloid binding fragment") refers to a protein that is mutated at one or more amino acids in order to modulate its therapeutic or diagnostic efficacy. In certain embodiments, a mutant contains a substitution, deletion and/or insertion at an amino that is known to interact with amyloid. In other embodiments, a mutant contains a substitution, deletion and/or insertion at an amino that is a conserved amino acid present in a wild-type g3p or amyloid binding fragment thereof. In some embodiments, a mutant has no more than 75, 50, 40, 30, 25, 20, 15, 12, 10, 9, 8, 7, 6, 5, 4, 3, 2, 1 amino acid differences as compared to the reference sequence. In some embodiments, the amino acid substitutions are conservative substitutions. The terms "variant" and "mutant" are used interchangeably herein except that a "variant" is typically non-recombinant in nature, whereas a "mutant" is typically recombinant.

The term "high stringency," as used herein, includes conditions readily determined by the skilled artisan based on, for example, the length of the DNA. Generally, such conditions are defined in Sambrook et al. Molecular Cloning: A Laboratory Manual, 2 ed. Vol. 1, pp. 1.101-104, Cold Spring Harbor Laboratory Press (1989), and include use of a prewashing solution for the nitrocellulose filters 5× SSC, 0.5% SDS, 1.0 mM EDTA (PH 8.0), hybridization conditions of 50% formamide, 6× SSC at 42° C. (or other similar hybridization solution, such as Stark's solution, in 50% formamide at 42° C.), and with washing at approximately 68° C., 0.2× SSC, 0.1% SDS. The skilled artisan will recognize that the temperature and wash solution salt concentration can be adjusted as necessary according to factors such as the length of the probe.

The term "moderate stringency," as used herein, includes conditions that can be readily determined by those having ordinary skill in the art based on, for example, the length of the DNA. The basic conditions are set forth by Sambrook et al. *Molecular Cloning: A Laboratory Manual*, 2d ed. Vol. 1, pp. 1.101-104, Cold Spring Harbor Laboratory Press (1989), and include use of a prewashing solution for the nitrocellulose filters 5× SSC, 0.5% SDS, 1.0 mM EDTA (pH 8.0), hybridization conditions of 50% formamide, 6× SSC at 42° C. (or other similar hybridization solution, such as Stark's solution, in 50% formamide at 42° C.), and washing conditions of 60° C., 0.5× SSC, 0.1% SDS.

The term "high sequence homology" means at least 70%, at least 75%, at least 80%, at least 85%, at least 90%, at least 91%, at least 92%, at least 93%, at least 94%, at least 95%, at least 96%, at least 97%, at least 98%, or at least 99% amino acid sequence homology with the reference sequence as measured using known computer programs, such as the Bestfit program.

A "fusion protein" is a non-naturally occurring protein comprising at least two polypeptide domains.

A "g3p fusion protein" comprises a g3p protein linked to a second domain.

An "N1-N2 fusion protein" (also termed "N1N2 fusion protein") comprises the N1 and N2 domains (or mutants, fragments, or variants of either), but not the N3/CT domain, of a g3p protein linked to a second domain. A N1N2 fusion protein may or may not comprise the hinge region.

An "N2 fusion protein" comprises the N2 domain (or mutants, fragments, or variants of N2), but neither the N1 nor N3/CT domains, of a g3p protein linked to a second domain. A N2 fusion protein may or may not comprise the hinge region.

As used herein, "Construct 1" is derived from wild type M13 (see, Genbank file: NC_003287.2, version GI:56718463. In Construct 1, as compared to wild type M13, Ser378(AGC) is changed to Gly(GGC), and Ile87 (ATT) is changed to Asn(AAC)). Construct 1 comprises the amino acids of SEQ ID NO: 10.

"Construct 2" is a wild type M13 isolate (GenBank JX412914.1). Construct 2 comprises the amino acids of SEQ ID NO:12.

phage. Thus, in one aspect of the invention, an isolated g3p is obtained from any naturally occurring filamentous bacteriophage. Recombinant forms of g3p can also be produced. Recombinant g3p may correspond to a wild type g3p from any naturally occurring filamentous bacteriophage. Thus, recombinant, isolated g3p is also encompassed by the invention.

One example of g3p, from phage M13, is presented in SEQ ID NO: 1. Unless otherwise clearly specified, any g3p mutations described are in reference to SEQ ID NO: 1 shown below in clean and annotated form:

```
  1 AETVESCLAK PHTENSFTNV WKDDKTLDRY ANYEGCLWNA TGVVVCTGDE TQCYGTWVPI

61 GLAIPENEGG GSEGGGSEGG GSEGGGTKPP EYGDTPIPGY TYINPLDGTY PPGTEQNPAN

121 PNPSLEESQP LNTFMFQNNR FRNRQGALTV YTGTVTQGTD PVKTYYQYTP VSSKAMYDAY

181 WNGKFRDCAF HSGFNEDPFV CEYQGQSSDL PQPPVNAGGG SGGGSGGGSE GGGSEGGGSE

241 GGGSEGGGSG GGSGSGDFDY EKMANANKGA MTENADENAL QSDAKGKLDS VATDYGAAID

301 GFIGDVSGLA NGNGATGDFA GSNSQMAQVG DGDNSPLMNN FRQYLPSLPQ SVECRPFVFS

361 AGKPYEFSID CDKINLFRGV FAFLLYVATF MYVFSTFANI LRNKES
```

Annotated
```
                                                                SEQ ID NO: 1
  1 AETVESCLAK PHTENSFTNV WKDDKTLDRY ANYEGCLWNA TGVVVCTGDE TQCYGTWVPI

61 GLAIPENEGG GSEGGGSEGG GSEGGGTKPP EYGDTPIPGY TYINPLDGTY PPGTEQNPAN

121 PNPSLEESQP LNTFMFQNNR FRNRQGALTV YTGTVTQGTD PVKTYYQYTP VSSKAMYDAY

181 WNGKFRDCAF HSGFNEDPFV CEYQGQSSDL PQPPVNAGGG SGGGSGGGSE GGGSEGGGSE

241 GGGSEGGGSG GGSGSGDFDY EKMANANKGA MTENADENAL QSDAKGKLDS VATDYGAAID

301 GFIGDVSGLA NGNGATGDFA GSNSQMAQVG DGDNSPLMNN FRQYLPSLPQ SVECRPFVFS

361 AGKPYEFSID CDKINLFRGV FAFLLYVATF MYVFSTFANI LRNKES
```

"Construct 3" is a recombinant soluble g3p fragment comprising the N1 and N2 domains of g3p (rs-g3p(N1N2)) comprising the amino acids of SEQ ID NO:20.

"Construct 4" is recombinant soluble g3p fragment IgG4 Fc fusion protein (rs-g3p(N1N2)-hIgG4-Fc) comprising the amino acids of SEQ ID NO:9. The N1N2 region of "Construct 4" is derived from the N1N2 region of "Construct 1."

"Construct 5" is a recombinant soluble g3p fragment IgG4 Fc fusion protein (rs-g3p(N1N2)-hIgG4-Fc) comprising the amino acids of SEQ ID NO:11. The N1N2 region of "Construct 5" is derived from the N1N2 region of "Construct 2."

"Construct 6" is recombinant soluble g3p fragment IgG1 Fc fusion protein (rs-g3p(N1N2)-hIgG1-Fc) comprising the amino acids of SEQ ID NO:13. The N1N2 region of "Construct 6" is derived from the N1N2 region of "Construct 2."

Sources of g3p

Filamentous bacteriophage are a group of related viruses that infect gram negative bacteria, such as, e.g., *E. coli*. See, e.g., Rasched and Oberer, *Microbiology Reviews* (1986) December:401-427. Examples of filamentous bacteriophage include, but are not limited to, phage of the Ff family (i.e., at least M13, f1, and fd) and phage of the 1-family (i.e., at least 122, Ike, If1).

All naturally occurring filamentous bacteriophage contain g3p as a minor coat protein present in 3 to 5 copies per

TABLE 1

Key for annotated SEQ ID NO: 1

| Region | Residues | Residue when signal peptide is present | Key |
| --- | --- | --- | --- |
| N1 | 1-67 | 19-85 | underline |
| G1 | 68-86 | 86-104 | highlight |
| N2 | 87-217 | 105-235 | underline and bold |
| G2 | 218-256 | 236-274 | italic |
| N3 | 257-406 | 275-424 | highlight and underline |

SEQ ID NO: 1 is GenBank NP-510891.1 with the 18 amino acid signal peptide removed, thus the amino acid numbering is for the mature g3p. The signal peptide is generally included in any expression construct, and immature g3p that includes the signal peptide is included within the scope of the various embodiments of the invention unless context makes clear that it is expressly excluded. SEQ ID NO: 1 is provided as a reference sequence only. It is in no way intended to limit the invention.

Sequences of g3p from multiple sources are known. Exemplary g3p amino acid sequences for bacteriophage of the Ff family include those sequences found in UniProt accession numbers P69169 (phage f1), P03661 (phage fd), and P69168 (phage m13). Exemplary g3p amino acid sequences for bacteriophage of the 1-family include P15415

(phage 122), P03663 (phage Ike), and O80297 (phage If1). Alignments of several g3p sequences are presented in FIG. 2.

G3p useful in this invention also includes fragments, mutants, and/or variants of g3p. Mutants or variants may be described with reference to a full length g3p or with reference to a fragment of g3p. Any full length or fragment g3p, including mutants and/or variants thereof that retain the ability to bind to amyloid, regardless of their ability to disaggregate amyloid is within the scope of the present invention. Any protein "comprising" such g3p is also encompassed by the present invention. Likewise, proteins "including," "consisting of," "consisting essentially of," or "having" such g3p are also encompassed.

Amyloid-Binding and Amyloid Disaggregating Fragments of g3p

As mentioned, g3p has two amino-terminal domains, N1 and N2, that interact to form an N1-N2 complex, and one carboxy-terminal domain, N3 (also called "CT"). In Ff phage, the N1 domain comprises residues 1-67 and the N2 domain comprises residues 87-217 of mature g3p. Residues 87-123 form the hinge that allows opening and closing between N1 and N2. Sometimes the hinge is considered part of N2, whereas in other instances it is treated as a separate element. N1 and N2 are also linked by flexible glycine-rich linker sequence. Within N1, there are two disulphide bridges between Cys7 and Cys36 and between Cys46 and Cys53. There is a single disulphide bridge in N2 between Cys188 and Cys201. The N3/CT domain comprises residues 257 to 406. Hollinger, 1999; Marvin, 1998. In the carboxy terminal domain there is a disulphide bridge between Cys354 and Cys371. Marvin, 1998. There are no interdomain disulphide bridges in g3p.

Non-limiting examples of amyloid binding fragments of g3p include the N2 domain either with the hinge (e.g., at least residues 87-217 of SEQ ID NO: 1) or without the hinge (e.g., at least residues 124-217 of SEQ ID NO: 1); and the N1-N2 domains (e.g., at least residues 1-67 and 87-217 of SEQ ID NO: 1), either with or without the intervening linker sequence (e.g., with or without residues 68-86 of SEQ ID NO: 1), and either with or without the hinge. In any of the foregoing examples, the N2 or N1N2 fragments may be the N2 or N1N2 found in a wild-type filamentous bacteriophage or a recombinant N2 or N1N2. In any of the foregoing examples, the N2 or N1N2 fragments may mutants or variants of the wild-type filamentous bacteriophage sequence.

Useful amyloid binding fragments of g3p include any fragment of g3p, including N2 and N1N2 fragments that retain the ability to bind to amyloid, regardless of the fragment's ability to disaggregate amyloid. Any protein "comprising" such amyloid binding fragment (or mutant or variant thereof) is encompassed by the present invention. Likewise, proteins "including," "consisting of," "consisting essentially of," or "having" the g3p fragment or variant are also encompassed.

N2 and N2 Polypeptide Mutants and Variants

A primary structure alignment of N2 from: fd, f1, M13, Ike, 12-2, and If1 is shown as FIG. 26. The amino acids of fd are shown in SEQ ID NO:14; f1 in SEQ ID NO:15; M13 in SEQ ID NO:16; Ike in SEQ ID NO:17; 12-2 in SEQ ID NO:18; and If1 in SEQ ID NO:19. Using this figure and alignment as guidance, one embodiment of the invention encompasses a N2 polypeptide, N2 polypeptide mutants, and N2 polypeptide variants, comprising the amino acids of SEQ ID NO: 14, 15, 16, 17, 18, or 19, including any amyloid binding fragments thereof.

In other embodiments, the N2 polypeptide is a N2 polypeptide mutant or variant that retains its ability to bind to amyloid and has an amino acid sequence that comprises no more than 75, 50, 40, 30, 25, 20, 15, 12, 10, 9, 8, 7, 6, 5, 4, 3, 2, 1 amino acid differences when aligned with the amino acid sequence of any one of SEQ ID NO: 14, 15, 16, 17, 18, or 19. In FIG. 26, an asterisk "*" indicates positions which have a single, fully conserved residue. A colon ":" indicates conservation between groups of strongly similar properties that score greater than 0.5 in the Gonnet PAM 250 matrix. A period "." indicates conservation between groups of weakly similar properties that score equal to or less than 0.5 in the Gonnet PAM 250 matrix. In some aspects of these embodiments, the N2 polypeptide mutant or variant does not comprise an amino acid difference at any position indicated with an "*" in FIG. 26. In more specific aspects, the N2 polypeptide mutant or variant does not comprise an amino acid difference at any position indicated with an "*" and comprises the same amino acid as at least one of SEQ ID NO: 14, 15, 16, 17, 18, or 19 at each position indicated with a ":" in FIG. 26. In even more specific aspects, the N2 polypeptide mutant or variant does not comprise an amino acid difference at any position indicated with an "*" and comprises the same amino acid as at least one of SEQ ID NO: 14, 15, 16, 17, 18, or 19 at each position indicated with a ":" and each position indicated with a "." in FIG. 26.

In other embodiments, a N2 polypeptide variant is described by specifying a percent amino acid similarity to SEQ ID NO: 14, 15, 16, 17, 18, or 19 again with the caveat that the N2 polypeptide variant binds amyloid. In these embodiments, the N2 polypeptide shares at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over the amino acids of reference sequences shown in SEQ ID NO: 14, 15, 16, 17, 18, or 19.

In other embodiments, a N2 polypeptide is described by specifying a percent amino acid similarity to the N2 region of SEQ ID NO: 1, again with the caveat that the N2 polypeptide variant binds amyloid. In these embodiments, the N2 polypeptide variant shares at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over N2 region of SEQ ID NO: 1.

In still other embodiments, a N2 polypeptide is described by secondary or tertiary structure. It is known that fd-N2 and If1-N2 domains use homologous parts of their surfaces to bind to the same site on the F-pilus in *E. coli*. Lorenz et al., J Mol Biol. 405:989-1003 (2011) at, for example, 990. The amino acid residues and secondary and tertiary structure that mediate N2 binding to F-pilus also mediate N2 binding to amyloid. Thus, amino acid residues and secondary and tertiary structures that are critical for N2 to F-pilus binding are also critical for N2-amyloid binding. N2 polypeptide variants comprising the amino acids required to maintain the secondary and tertiary structure in the region of N2-F-pilus binding are within the scope of the present invention.

N1N2 and N1N2 Polypeptide Mutants and Variants

A primary structure alignment of fd, f1, and M13 is shown as FIG. 2A, and Ike, 12-2, and If1 as FIG. 2B. Using this alignment as guidance, one embodiment of the invention encompasses a N1N2 polypeptide, polypeptide mutant, or polypeptide variant comprising the amino acids that are conserved between fd, f1, and M13 or as between 12-2, Ide, and If1, as identified with reference to the sequences of FIG. 2. In other embodiments, the N1N2 polypeptide is a N1N2 polypeptide mutant or variant, that retains its ability to bind to amyloid and has an amino acid sequence that comprises no more than 75, 50, 40, 30, 25, 20, 15, 12, 10, 9, 8, 7, 6, 5, 4, 3, 2, 1 amino acid differences when aligned with the amino acid sequence of any one of SEQ ID NO: 1, 2, 3, 5 or 6.

In other embodiments, a N1N2 polypeptide, mutant, or variant is described by specifying a percent amino acid similarity to the N1N2 region of SEQ ID NO: 1, again with the caveat that the N1N2 polypeptide variant binds amyloid. In these embodiments, the N1N2 polypeptide variant shares at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over N1 and N2 regions of SEQ ID NO: 1.

Fusion Proteins

In one aspect, the invention relates to fusion proteins. The fusion protein comprises g3p, an amyloid-binding fragment of g3p, a ToIA binding molecule, or a ToIA inhibitor. Fusion proteins comprising mutant or variant g3p or g3p fragments are fully encompassed. The fusion protein is linked, fused, conjugated, coupled, or associated with/to at least one additional protein or protein domain with which it is not normally associated. In one embodiment, the fusion protein is a g3p fusion protein that comprises a g3p protein linked to a second domain. In another embodiment, the fusion protein is an amyloid-binding fragment of a g3p protein linked to a second domain. In another embodiment, the fusion protein is an N1N2 fusion protein, which comprises the N1 and N2 domains, but not the CT domain, of a g3p protein. In still another embodiment, the fusion protein is an N2 fusion protein, which comprises the N2 domain, but neither the N1 nor CT domains, of a g3p protein. As noted, some aspects of the invention relate to mutated or variated g3p protein or amyloid-binding fragments thereof, and to mutated or variated N1N2 or N2 domains that bind amyloid fibers. Thus, fusion proteins comprising these mutated or variated forms are also part of the invention.

The g3p or amyloid binding fragment and the fusion partner polypeptide may be part of a continuous amino acid sequence with the fusion partner polypeptide linked directly or through a short peptide linker to either the N terminus or the C terminus of the g3p or amyloid binding fragment polypeptide. In such cases, the g3p or amyloid binding fragment thereof and the fusion partner polypeptide may be translated as a single polypeptide from a coding sequence that encodes both the g3p or amyloid binding fragment thereof and the fusion partner polypeptide.

In some embodiments, the fusion protein comprises an immunoglobulin constant region as the second domain. Fusion proteins comprised of immunoglobulin constant regions linked to a protein of interest, or fragment thereof, have been described (see, e.g., U.S. Pat. Nos. 5,480,981 and 5,808,029; Gascoigne et al. 1987, *Proc. Natl. Acad. Sci. USA* 84:2936; Capon et al. 1989, *Nature* 337:525; Traunecker et al. 1989, *Nature* 339:68; Zettmeissl et al. 1990, *DNA Cell Biol. USA* 9:347; Byrn et al. 1990, *Nature* 344:667; Watson et al. 1990, *J. Cell. Biol.* 110:2221; Watson et al. 1991, *Nature* 349:164; Aruffo et al. 1990, *Cell* 61:1303; Linsley et al. 1991, *J. Exp. Med.* 173:721; Linsley et al. 1991, *J. Exp. Med.* 174:561; Stamenkovic et al., 1991, *Cell* 66:1133; Ashkenazi et al. 1991, *Proc. Natl. Acad. Sci. USA* 88:10535; Lesslauer et al. 1991, *Eur. J. Immunol.* 27:2883; Peppel et al. 1991, *J. Exp. Med.* 174:1483; Bennett et al. 1991, *J. Biol. Chem.* 266:23060; Kurschner et al. 1992, *J. Biol. Chem.* 267:9354; Chalupny et al. 1992, *Proc. Natl. Acad. Sci. USA* 89:10360; Ridgway and Gorman, 1991, *J. Cell. Biol.* 115, Abstract No. 1448; Zheng et al. 1995, *J. Immun.* 154:5590). These molecules usually possess both the biological activity associated with the linked molecule of interest as well as the effector function, or some other desired characteristic associated with the immunoglobulin constant region (e.g., biological stability, cellular secretion).

In some embodiments, the fusion protein comprises an Fc fragment of an immunoglobulin constant region. Fc expression cassettes may be purchased commercially. The Fc fragment can be comprised of the CH2 and CH3 domains of an immunoglobulin and the hinge region of the immunoglobulin. The Fc fragment can be the Fc fragment of an IgG1, an IgG2, an IgG3 or an IgG4. In one specific embodiment, the portion of an immunoglobulin constant region is an Fc fragment of an IgG1. In another embodiment, the portion of an immunoglobulin constant region is an Fc fragment of an IgG4. In still another embodiment, the portion of an immunoglobulin constant region is an Fc fragment of an IgM.

Thus, in one embodiment, a recombinant soluble g3p or amyloid-binding fragment is fused to an immunoglobulin Fc domain using standard molecular biology techniques. The recombinant soluble g3p or amyloid-binding fragment may be mutated or variated. For example, an amyloid-binding fragment of g3p, such as the N1N2 domain or the N2 domain, can be cloned into an IgGFc fusion expression vector. Exemplary IgGFc fusion vectors include, for example, one of the pFUSE-Fc vectors available from InvivoGen. In some embodiments, the resulting bivalent (e.g., g3p(N1N2)-IgGFc or g3p(N2)-IgGFc fusion protein will have higher avidity for amyloid binding than the recombinant soluble g3p since it is now bivalent.

In other embodiments, the fusion protein comprises a non-Fc protein linked to a g3p or amyloid binding fragment of g3p.

In other embodiments, the fusion protein comprises at least two g3p polypeptides or amyloid-binding fragments thereof. In other embodiments, the fusion protein comprises three or more g3p polypeptides, or amyloid-binding fragments thereof. In other embodiments, the fusion protein comprises five g3p polypeptides, or amyloid-binding fragments thereof. Such dimeric and multimeric fusion proteins provide higher avidity interactions since they include more than one g3p, or amyloid-binding fragments thereof.

In other embodiments, the fusion protein comprises albumin. See for example, U.S. Pat. No. 6,686,179 to Fleer.

In all instances, the g3p or amyloid binding fragment of g3p in the fusion protein encompasses mutants and variants thereof.

In general, the fusion proteins bind to amyloid at least as effectively as the corresponding unlinked g3p or g3p fragment thereof. When applicable, the fusion proteins are at least as effective in mediating disaggregation of amyloid, promoting amyloid clearance, inhibiting amyloid aggregation, and/or removing or preventing the formation of toxic oligomers as the corresponding unlinked g3p or fragment thereof. In some embodiments, the fusion protein binds amyloid and is at least as effective in mediating disaggregation of amyloid, promoting amyloid clearance, inhibiting amyloid aggregation, and/or removing or preventing the formation of toxic oligomers as is a recombinant, soluble g3p comprising SEQ ID NO: 1. In still other embodiments, the fusion protein binds amyloid and is at least as effective in mediating disaggregation of amyloid, promoting amyloid clearance, inhibiting amyloid aggregation, and/or removing or preventing the formation of toxic oligomers as phage M13. In yet other embodiments, the fusion protein binds amyloid and is more effective in mediating disaggregation of amyloid, promoting amyloid clearance, inhibiting amyloid aggregation, and/or removing or preventing the formation of toxic oligomers than phage M13. In some embodiments, the fusion protein binds amyloid and is at least as effective in reducing amyloid in a protein misfolding disease as phage M13. In still other embodiments, the fusion protein binds amyloid and is more effective in reducing amyloid in a protein misfolding disease as phage M13. In still other embodiments, the fusion protein binds amyloid and is at least or more effective in preventing amyloid formation as phage M13.

Fusion proteins can be synthesized using techniques well known in the art. For example, the fusion proteins of the invention can be synthesized recombinantly in cells (see, e.g., Sambrook et al. 1989, *Molecular Cloning A Laboratory Manual*, Cold Spring Harbor Laboratory, N.Y. and Ausubel et al. 1989, *Current Protocols in Molecular Biology*, Greene Publishing Associates and Wiley Interscience, N.Y.). Alternatively, the fusion proteins of the invention can be synthesized using known synthetic methods such as solid phase synthesis. Synthetic techniques are well known in the art (see, e.g., Merrifield, 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, The Proteins (3d ed.) 2:105; Erikson et al. 1976, *The Proteins* (3d ed.) 2:257; U.S. Pat. No. 3,941,763. Alternatively, the final construct may share essentially the same function as a recombinantly produced fusion protein, but simply be produced using non-recombinant techniques, such as ligation chemistry. Components of the fusion proteins may be prepared using the same general methodology described for g3p expression and g3p mutations.

In some embodiment, the g3p or amyloid binding fragment (or mutant or variant form thereof) may be fused to a marker sequence, such as a peptide that facilitates purification of the fused polypeptide (either alone or in addition to fusion to another protein or incorporation of a carrier molecule). The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* (1989) 86:821-824, for instance, hexa-histidine provides for convenient purification of the fusion protein. Another peptide tag useful for purification, the hemagglutinin (HA) tag, corresponds to an epitope derived from the influenza HA protein. (Wilson et al., (1984) *Cell* 37:767).

Phage Overexpressing g3p

In another aspect, the invention relates to bacteriophage modified to increase the number of copies of g3p expressed by the phage to more than the 3-5 copies typically found in wild type filamentous bacteriophage. In one embodiment, phage that express increased numbers of g3p may be selected from naturally occurring variants. In another embodiment, recombinant techniques are used to increase the copy number of g3p.

In some embodiments, a wild type sequence encoding g3p or amyloid binding fragments of g3p (including mutants or variants thereof) can be used to replace one of the genes encoding another bacteriophage coat protein. Depending upon the bacteriophage gene replaced, the number of g3p can be increased to 6, 7, 8, 9, 10, 15, 20, 25, 30, 35, 40, 50, 75, 100, 500, 1000, or even nearly 3000 copies (for example, if the gene 3 coding sequence were used to replace the gene 8 coding sequence or were fused to the end of the gene 8 coding sequence).

To produce phage expressing additional copies of g3p, a g3p coding sequence (or mutant or variant form thereof) is cloned as described elsewhere in the description. The g3p coding sequence (or mutant or variant form thereof) may then be used to replace another phage gene and expressed, if necessary in conjunction with helper phage.

Alternatively, in some embodiments the g3p coding sequence (or mutant or variant form thereof) is fused in frame to the coding sequence of another phage gene, either with or without an intervening "spacer" sequence. Methods of preparing phage proteins to which another protein or peptide is "fused" are well known in the phage display art, and g3p or an amyloid binding fragment thereof can be "displayed" in the same manner as, for example, antigens or antibody chains. E.g. Scott & Smith, Science (1990) 249: 386-90; Devlin et al., Science (1990) 249:404-06. When expression of only a fragment of g3p is desired, the coding sequence for the fragment (or mutant or variant form thereof) may be linked to the other gene so that one of the natural Ser/Gly linker sequences present in g3p serves as the linker. In some embodiments, only coding sequence for N2 or N1N2 domains (or mutant or variant form thereof) is fused in frame to the other gene.

Mutant G3P and Amyloid Binding Fragments

In another aspect, the invention relates to mutant g3p proteins and mutant amyloid-binding fragments thereof. Fusion proteins and phage comprising the mutant g3p proteins and amyloid-binding fragments are also part of the invention. Mutant g3p and mutant amyloid-binding fragments thereof may be produced, or selected, for properties that contribute to the therapeutic efficacy of the pharmaceutical compositions described in this application. For example, g3p or amyloid-binding fragments thereof may be recombinantly mutated or otherwise selected to posses one or more of the following properties relative to g3p of M13: increased affinity for amyloid binding, a reduced hinge $T_M$, increased avidity (avidity being distinguished from affinity in that avidity is used to describe the sum of all available amyloid binding where a g3p comprises more than one amyloid binding site), increased ability to disaggregate amyloid aggregates, or increased ability to prevent aggregation of amyloid fibrils. Alternatively, or in addition, the mutant g3p or mutant amyloid fragments thereof may incorporate other useful properties described elsewhere in the description.

Mutant g3p proteins can be produced by mutagenesis of phage, or by recombinant techniques, such as PCR-based site directed mutagenesis or random mutagenesis.

In some embodiments, mutants with higher affinity are produced by mutagenizing M13 and then selecting phage on an amyloid affinity column coupled with stringent washing conditions. Successive rounds of binding, washing, elution, and then expansion of selected phage enriches for those phage with high affinity binding to amyloid. Once increased affinity of the phage population is achieved using amyloid panning, individual clones with high affinity are selected and analyzed. In this way, phage mutants may be selected for high affinity binding following random mutagenesis.

G3p, or any amyloid binding fragments thereof, (e.g., N1N2 domains or N2 domains) may also be mutagenized using recombinant techniques. For example, a vector as described herein carrying g3p or an amyloid binding fragment thereof (e.g., N1N2 or N2) may be mutated using PCR-based mutagenesis strategies. The encoded, mutated protein is then expressed and amyloid binding and affinity of the mutants assessed as described.

Mutant amyloid binding fragments of g3p may also be derived from mutant g3p. For example, by mutating g3p and/or selecting for a mutated g3p with desirable properties and then obtaining the desired amyloid binding fragment therefrom, e.g., by proteolysis and subsequent purification.

Screening of phage bearing mutant g3p for increased affinity of amyloid binding, changes in temperature-sensitivity of binding, etc., may be used to identify phage for further characterization of the g3p of that phage. Screening for properties such as temperature sensitivity of binding can utilize an amyloid affinity column with one or more of the binding, washing, or elution steps conducted in a temperature dependent fashion.

In some embodiments, the mutant g3p or g3p amyloid-binding fragment binds amyloid with an affinity that is at least 3, 5, 10, 20, 30, 40, 50, 100, 200, 300, 400, 500 or even 1000 higher than binding of the corresponding unmutated g3p or g3p fragment from M13. In other embodiments, the mutant g3p or g3p amyloid-binding fragment retains amyloid-binding that is at least 70, 75, 80, 85, 90, 91, 92, 93, 94, 95, 96, 97, 98, or 99% as strong as binding of the corresponding unmutated g3p or amyloid-binding g3p fragment from M13. In some embodiments a mutant g3p or amyloid binding fragment that displays lower amyloid-binding affinity than the corresponding unmutated form also possesses another desirable biological (e.g., greater ability to disaggregate amyloid; greater ability to prevent aggregation of amyloid fibrils) or pharmaceutical (e.g., greater metabolic stability, favorable pharmacokinetic profile, greater solubility) property that is improved as compared to the corresponding unmutated form. Amyloid binding may be assessed by surface plasmon resonance or in a competitive ELISA, as described in the Examples.

In some embodiments, variants and/or mutants of g3p may be identified by screening DNA libraries using hybridization to M13 g3p to select related DNAs that hybridize to M13 g3p under either high stringency or moderate stringency conditions.

In some embodiments, a mutated g3p is a recombinantly produced g3p or amyloid-binding fragment thereof that differs from mature M13 g3p protein (SEQ ID NO: 1) by at least one amino acid residue but still binds amyloid. In some embodiments, individual point mutations are specified by providing the amino acid of the M13 g3p at a particular residue of the mature protein and the replacement amino acid at that residue. For example, "F194A" means the phenylalanine at position 194 of the mature M13 sequence has been changed to an alanine. In other embodiments, a mutated g3p is described by specifying a percent amino acid similarity to SEQ ID NO: 1, again with the caveat that the mutated g3p binds amyloid fibrils. In these embodiments, the mutated g3p shares at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over the full length of SEQ ID NO: 1. In those embodiments involving a mutated amyloid binding fragment of g3p, the mutated amyloid-binding fragment shares at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over the full length of the corresponding fragment of SEQ ID NO: 1.

As a practical matter, whether any particular polypeptide is at least 70%, 80%, 85%, 86%, 87%, 88%, 89%, 90%, 91%, 92%, 93%, 94%, 95%, 96%, 97%, 98%, or 99% identical to SEQ ID NO: 1 can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the portion of the reference amino acid sequence that is homologous to the query sequence.

In some embodiments of the various aspects, mutant g3p and amyloid binding fragments thereof include no mutations at an amino acid residue that is conserved among g3p of the Ff family, the I-family, or both the Ff and I-families. In other embodiments, the mutant g3p and amyloid binding fragments thereof include at most mutations at 1, 2, 3, 4, 5, 6, 7, 8, 9, or 10 amino acid residues that are conserved among g3p of the Ff family, the I-family, or both the Ff and I-families. In still other embodiments, the mutant g3p and amyloid binding fragments thereof include at most mutations at 0, 1, 2, 3, 4, 5, 6, 7, 8, 9, or 10 amino acid residues that are not conserved among g3p of the Ff family, the I-family, or both the Ff and I-families. In still another embodiment, the mutant g3p and amyloid binding fragments thereof include at most mutations at 0, 1, 2, 3, 4, 5, 6, 7, 8, 9, or 10 amino acid residues that are not conserved between one or more of 122, Ike, and If1. In yet other embodiments, the mutant g3p and amyloid binding fragments thereof include at most mutations at 1, 2, 3, 4, 5, 6, 7, 8, 9, or 10 amino acid residues that are not conserved among g3p of the Ff family, the I-family, or both the Ff and I-families. In some embodiments, the at most 1, 2, 3, 4, 5, 6, 7, 8, 9, or 10 mutations are located within the N1 domain. In some embodiments, the at most 1, 2, 3, 4, 5, 6, 7, 8, 9, or 10 mutations are located within the N2 domain. In some embodiments, the at most 1, 2, 3, 4, 5, 6, 7, 8, 9, or 10 mutations are located within the N2 domain and are not within the hinge region.

Site directed mutagenesis may target residues known to be important for stability of g3p, N1N2, or the N2 domain. For example, alanine replacement mutations at D94 and T95; E115, N122; L125; E126 and E127; E127 and E128; Q129; Q145; T154 and T156; Q157; T159 and D160; K163 and T164; Y166; and E196 and D197 have been previously shown to not significantly affect phage binding to F-pili, Deng & Perham, 2002. Accordingly, these positions are tolerant of mutation and a mutation at one or more of these positions may either enhance or have a neutral effect on the amyloid-binding ability in the g3p and g3p amyloid-binding fragments of the invention. Thus, in some embodiments, the invention includes a g3p or g3p amyloid-binding fragment that is mutated at one or more of D94, T95, E115, N122, L125, E126, E127, E128, Q129, Q145, T154, T156, Q157, T159, D160, K163, T164, Y166, E196, or D197 (relative to SEQ ID NO: 1). In some embodiments, the mutation at one or more of D94, T95, E115, N122, L125, E126, E127, E128, Q129, Q145, T154, T156, Q157, T159, D160, K163, T164, Y166, E196, or D197 is not exclusively a mutation to alanine.

Alanine replacement mutations at F194; F190 and H191, K184, R186, and D187; R142 and R144 have been previously shown to decrease binding to F-pili, Deng & Perham, 2002. Thus, in some embodiments, a mutation is chosen from a mutation that does not include one or more of the following residues: R142, R144, W181, K184, R186, D187, F190, H191, or F194 (numbering relative to SEQ ID NO: 1).

However, replacement of R142, R144, W181, K184, R186, D187, F190, H191, or F194 with a non-alanine residue may increase amyloid binding. Thus, in one embodiment, the mutation is a non-alanine mutation at one or more of R142, R144, W181, K184, R186, D187, F190, H191, or F194. In one embodiment, the mutation is a non-alanine mutation at F194. In another embodiment, the mutation is a non-alanine mutation at F190 and H191. In another embodiment, the mutation is a non-alanine mutation at K184, R186, and D187. In another embodiment, the mutation is a non-alanine mutation at W181. In another embodiment, the mutation is a non-alanine mutation at R142 and R144. In certain embodiments, the mutation is not exclusively one, some, or all of: T131, T101I, Q129H, G153D, W181A, F190A, F194A, and D209Y.

In some embodiments, the mutation is at one or more residues located on the surface of the N2 domain, which is the portion of g3p that binds F-pili. In one embodiment, the mutation is at one or more residues located on the outer rim of the N2 domain. In other embodiments, the mutation is at one or more residues located on the surface of the N1 domain, which is the portion of g3p that binds TolA. In one embodiment, the mutation is at one or more residues located on the outer rim of the N1 domain. In another embodiment, the mutation is at one or more solvent accessible residues on g3p. In yet another embodiment, the mutation(s) shifts the cis/trans equilibrium at Pro213 to greater than 50, 60, 70, 80, 90, or 95% trans. Thus, in some embodiments, the g3p is a mutated g3p with a cis/trans equilibrium at Pro213 that is at least 50, at least 60, at least 70, at least 80, at least 90, or at least 95% trans.

In some embodiments, the g3p mutant or amyloid binding fragment thereof does not include mutations at structurally conserved residues. Examples of structurally conserved residues include residues that, despite potential sequence insertions, are involved in providing domain structure in both Ff and I-family members.

In some embodiments, any mutation made preserves amyloid binding. In other embodiments, the mutation does not replace a proline residue.

In some embodiments, any mutation made preserves amyloid binding and does not replace a cysteine residue. In some embodiments, the mutation preserves all, at least one, at least two, at least three or all four of the disulphide bridges found within g3p. Thus, in one embodiment, any mutation preserves the two disulphide bridges in N1 between Cys7 and Cys36 and between Cys46 and Cys53. In another embodiment, any mutation preserves either, but not both, of the disulphide bridges in N1 between Cys7 and Cys36 and between Cys46 and Cys53. In one embodiment, the disulphide bridge between Cys188 and Cys201 is preserved. In some embodiments, each of the disulphide bridges Cys7 and Cys36, Cys46 and Cys53, and Cys188 and Cys201 are preserved. In one embodiment, the mutations preserve the disulphide bridge between Cys354 and Cys371. In some embodiments, the mutations preserve the disulphide bridges between Cys7 and Cys36, Cys46 and Cys53, Cys188 and Cys201, and Cys354 and Cys371.

In some embodiments, any mutation made preserves amyloid binding and decreases the melting temperature ($T_M$) of N1N2. $T_M$ may be measured using any of the methods described in the Examples. Mutants that decrease the $T_M$ of N1N2 are expected to exhibit better binding to Aβ, inhibit Aβ assembly to a greater extent, and to be at least as effective in a disaggregation assay as g3p of M13. Accordingly, such mutants, as well as fusion proteins and phage comprising these mutants are expected to be at least as efficacious therapeutically as the corresponding sequences in M13, fusion proteins thereof, and intact M13, respectively, in treating one or more protein misfolding diseases.

Mutants may also be designed to include a targeting sequence. Such targeting sequences may be inserted into the flexible linker regions between N1N2, or between N2 and another domain in an N2 fusion protein. Targeting nuclear localization sequences (NLS) might be beneficial in Huntington's disease. Targeting the endosome may be beneficial in Parkinson's Disease's.

In addition to targeting specific regions in the cell, targeting sequences may be used to target different kinds of amyloid. Nucleating sequences may increase affinity and direct the mutant protein to a particular amyloid. Other mutants may be prepared that include peptide sequences that are so hydrophobic that they precipitate on their own. For example, multiple AVVAI sequences can be added to g3p and or amyloid binding fragments thereof (e.g., N2 and N1N2) and/or their fusion proteins to generate chimeric proteins that have enhanced, multiple binding sequences. Some examples of peptides that bind amyloid and may be incorporated into the mutant or chimeric proteins comprising g3p, N2, and N1N2 and/or their fusion proteins are the peptide inhibitors based on the GxFxGxF (SEQ ID NO: 21) framework described in Sato, Biochemistry (2006) 45:5503-16 and the KLVFF (SEQ ID NO: 22) peptide described in Tjernberg et al., J. Biol. Chem. (1996) 271:8545-48. Other targeting moieties are known and may also be used in the present invention. See, e.g., Sciarretta et al., Methods in Enzymology (2006) 413:273-312.

Amyloid-Binding Display Vehicles and Carriers

In another aspect of the invention g3p and amyloid-binding fragments thereof (including mutants and variants of any of the foregoing), including but not limited to N1N2 domains and N2 domains, as well as molecules, polypeptides and fusion proteins that comprise them may be combined with other organic or even inorganic carriers that provide molecular scaffolds that preserve amyloid binding but provide additional features.

In some embodiments, the g3p or amyloid binding fragment thereof, or g3p fusion protein, and the carrier are covalently linked through non-recombinant means, such as, for example, a chemical linkage other than a peptide bond. Any suitable chemical crosslinker may be used. Any known methods of covalently linking polypeptides to other molecules (for example, carriers) may also be used. In some embodiments, the g3p or amyloid binding fragment thereof, or g3p fusion protein, and the carrier may be fused through a linker that is comprised of at least one amino acid or chemical moiety.

In some embodiments, the g3p or amyloid binding fragment thereof, or g3p fusion protein, and the carrier are noncovalently linked. In some such embodiments, they may be linked, for example, using binding pairs. Exemplary binding pairs include, but are not limited to, biotin and avidin or streptavidin, an antibody and its antigen, etc.

Examples of carriers include, but are not limited to, viral particles (including phage, see below) in which a g3p protein or amyloid binding fragment thereof not native to the virus is incorporated as part of the viral structure; polymers, whether natural, synthetic, or mixed; polymer-coated structures, such as beads (including surface derivatized beads); polyamino acids, nucleic acids; and liposomes. The carrier may be linked either directly or indirectly to the g3p or amyloid-binding fragment. Depending upon the carrier, intermediate linkages may be used to provide appropriate spacing between the carrier and the amyloid-binding domain.

A polyaminoacid may be a carrier protein. Such polyaminoacids may be chosen from serum album (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. The location of attachment of the polyaminoacid may be at the N terminus or C terminus, or other places in between, and also may be connected by a chemical linker moiety to the g3p or amyloid binding fragment thereof.

In some embodiments, carriers include molecules with oligomerization domains. Oligomerization offers functional advantages when one of the functions of a protein or fragment thereof is binding, including multivalency, increased binding strength, and the combined function of different domains. These features are seen in natural proteins and may also be introduced by protein engineering. Accordingly, the invention also provides g3p and amyloid binding fragments (including mutants and variants thereof) such as the N1N2 domain and N2 domain, comprising an oligomerization domain, for example, a dimerization domain. Suitable oligomerization domains include coiled-coil domains, including alpha-helical coiled-coil domains; collagen domains; collagen-like domains, and dimeric immunoglobulin domains. Suitable coiled-coil polypeptide fusion partners of the invention include tetranectin coiled-coil domain, the coiled-coil domain of cartilage oligomeric matrix protein; angiopoietin coiled-coil domains; and leucine zipper domains. When collagen or collagen-like oligomerization domains are used, they may comprise, for example, those found in collagens, mannose binding lectin, lung surfactant proteins A and D, adiponectin, ficolin, conglutinin, macrophage scavenger receptor, and emilin. While some of these domains may be incorporated as fusion proteins, in many embodiments they are non-recombinantly linked to the g3p, N1N2 domain, N2 domain or other amyloid-binding fragments, for example, through covalent bonding.

In addition, the invention provides g3p or amyloid-binding fragments thereof, or g3p fusion proteins, linked to a polymer. Polymers employed in the invention will be pharmaceutically acceptable for the preparation of a therapeutic product or composition.

Polymers are typically attached to a g3p or amyloid binding fragment thereof with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

PEG moieties of the invention may be branched or linear chain polymers. In an embodiment, the present invention contemplates a chemically derivatized polypeptide which includes mono- or poly- (e.g., 2-4) PEG moieties. Pegylation may be carried out by any of the pegylation reactions known in the art. Methods for preparing a pegylated protein product are generally known in the art. Optimal reaction conditions will be determined on a case by case basis, depending on known parameters and the desired result.

There are a number of PEG attachment methods available to those skilled in the art, for example, EP 0 401 384; Malik et al., *Exp. Hematol.*, (1992) 20:1028-1035; Francis, *Focus on Growth Factors*, 3:4-10 (1992); EP 0 154 316; EP 0 401 384; WO 92/16221; WO 95/34326; and the other publications cited herein that relate to pegylation.

When a g3p, N1N2 domain, N2 domain or other amyloid-binding fragment (as well as mutants and variants thereof and compounds, polypeptides and fusion proteins comprising any of the foregoing) is PEGylated, the PEG may be attached by either chemically derivatizing the g3p, N1N2 domain, N2 domain or other amyloid-binding fragment. In other embodiments, an amino acid residue suitable for modification by a PEG molecule may be recombinantly introduced into the g3p, N1N2 domain, N2 domain or other amyloid-binding fragment.

Pegylation may be performed via an acylation reaction or an alkylation reaction with a reactive polyethylene glycol molecule. Thus, protein products of the present invention include pegylated proteins wherein the PEG groups are attached via acyl or alkyl groups. Such products may be mono-pegylated or poly-pegylated (for example, those containing 2-6 or 2-5 PEG groups). An example of a suitable activated PEG ester is PEG esterified to N-hydroxysuccinimide (NHS).

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

In some embodiments, g3p, N1N2 domain, N2 domain or other amyloid-binding fragment is expressed as part of a phage and the g3p, N1N2 domain, N2 domain or other amyloid-binding fragment is prepared by isolating it from the phage particles. In general, however, recombinant techniques are used to prepare the g3p, amyloid binding fragment of g3p (including mutants and variants thereof). In general, the resulting protein is isolated prior to combining with a carrier.

In some embodiments, the display vehicle is a phage. In these embodiments, a gene encoding a g3p protein, N1N2 domain, N2 domain, and other amyloid-binding fragment (including mutants and variants of all the foregoing) is incorporated into a bacteriophage genome and expressed as part of the phage. For example, in one embodiment, a mutant g3p protein with higher amyloid-binding affinity than the g3p of M13 phage is used to replace the wild type g3p of M13 phage. The resulting phage thus also has improved binding relative to wild type M13. However, any of the g3p or amyloid binding fragments described may be incorporated into a phage. In these embodiments, the wild type gene 3 may be replaced entirely by a g3p of the invention.

Alternatively, as discussed for phage with increased copy number of g3p, the recombinant molecule may be fused to a gene encoding a phage coat protein (including wild type g3p) and displayed on the phage in a manner analogous to antigen and antibody chains in phage display libraries. Any filamentous bacteriophage may be modified to express a g3p of the invention, including, but not limited to M13, fd, f1, 122, Ike, or If1. In some embodiments, a helper phage may be used in conjunction with the modified phage.

Recombinant Techniques

In general a DNA encoding a g3p protein or amyloid binding fragment thereof (as well as mutants and variants thereof and compounds, polypeptides and fusion proteins comprising any of the foregoing) is prepared using conventional recombinant DNA techniques, such as cloning of the g3p gene, direct DNA synthesis, or by isolating the corresponding DNA from a library using, for example, the M13 sequence as a probe. (See, e.g., Sambrook et al. 1989, *Molecular Cloning A Laboratory Manual*, Cold Spring Harbor Laboratory, N.Y. and Ausubel et al. 1989, *Current Protocols in Molecular Biology*, Greene Publishing Associates and Wiley Interscience, N.Y.).

For recombinant production, a nucleic acid sequence encoding a g3p or amyloid binding fragment thereof is inserted into an appropriate expression vector which contains the necessary elements for the transcription and translation of the inserted coding sequence, or in the case of an RNA viral vector, the necessary elements for replication and translation. The encoding nucleic acid is inserted into the vector in proper reading frame.

Accordingly, the invention provides vectors comprising polynucleotides that encode g3p or an amyloid binding fragment thereof (including mutants and variants thereof). Vectors comprising polynucleotides that encode a g3p or g3p-fusion molecule are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells. Exemplary such vectors are described, e.g., in Running Deer et al., *Biotechnol. Prog.* (2004) 20:880-889.

In some embodiments, a vector is chosen for in vivo expression of g3p, amyloid binding fragment thereof and/or g3p fusion molecules in animals, including humans. In some such embodiments, expression of the polypeptide is under the control of a promoter that functions in a tissue-specific manner.

Expression vectors are transfected or co-transfected into a suitable target cell, which will express the polypeptides. Nonlimiting exemplary transfection methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art. A variety of host-expression vector systems may be utilized to express the proteins described herein including either prokaryotic or eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., CHO, Cos, HeLa cells). The proteins may also be produced recombinantly in duckweed. See, e.g., U.S. Pat. No. 8,022,270.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. Another amplifiable marker is the DHFRr cDNA (Simonsen and Levinson, *Proc. Natl. Acad. Sci.* (*USA*), (1983) 80:2495). Selectable markers are reviewed by Thilly (*Mammalian Cell Technology*, Butterworth Publishers, Stoneham, Mass.) and the choice of selectable markers is well within the level of ordinary skill in the art.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV, the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the expression product of the invention may be driven by any of a number of promoters. For example, viral promoters such as the 35S RNA and 19S RNA promoters of CaMV (Brisson et al., *Nature* (1984) 310:511-514), or the coat protein promoter of TMV (Takamatsu et al., *EMBO J.* (1987) 6:307-311) may be used; alternatively, plant promoters such as the small subunit of RUBISCO (Coruzzi et al., *EMBO J.* (1984) 3:1671-1680; Broglie et al., Science (1984) 224:838-843) or heat shock promoters, e.g., soybean hsp17.5-E or hsp17.3-B (Gurley et al., *Mol. Cell. Biol.* (1986) 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach 1988, *Methods for Plant Molecular Biology*, Academic Press, NY, Section VIII, pp. 421-463; and Grierson & Corey 1988, *Plant Molecular Biology*, 2d Ed., Blackie, London, Ch. 7-9.

In one insect expression system that may be used to produce proteins of the invention, *Autographa californica* nuclear polyhidrosis virus (AcNPV) is used as a vector to express the foreign genes. The virus grows in *Spodoptera*

*frugiperda* cells. A coding sequence may be cloned into non-essential regions (for example, the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed. (see, e.g., Smith et al., J. Virol. (1983) 46:584; U.S. Pat. No. 4,215,051). Further examples of this expression system may be found in Ausubel et al., eds. 1989, *Current Protocols in Molecular Biology*, Vol. 2, Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts (see, e.g., Logan & Shenk, *Proc. Natl. Acad. Sci.* (*USA*) (1984) 81:3655). Alternatively, the vaccinia 7.5 K promoter may be used (see, e.g., Mackett et al., *Proc. Natl. Acad. Sci.* (*USA*) (1982) 79:7415; Mackett et al., *J. Virol.* (1984) 49:857; Panicali et al., *Proc. Natl. Acad. Sci.* (*USA*) (1982) 79:4927). Other viral expression systems include adeno-associated virus and lentiviruses.

Host cells containing the DNA constructs are grown in an appropriate growth medium. As used herein, the term "appropriate growth medium" means a medium containing nutrients required for the growth of cells. The recombinantly produced protein of the invention can be isolated from the culture media using techniques conventional in the art.

In Vitro Assays

In some embodiments, disaggregation of amyloid may be monitored using the Thioflavin T Fluorescence (ThT) assay.

In some embodiments, disaggregation is tested by monitoring detergent solubilization in the presence or absence of a composition of the invention. For example, aggregated α-synuclein can be treated with a composition of the invention. A composition that disaggregates the aggregated α-synuclein will cause the α-synuclein fibers to solubilize faster in detergents such as SDS, compared to untreated fibers. This conversion of the amyloid fibers into soluble forms can be monitored by incorporating a proportion of labeled (e.g., with Cy5) α-synuclein monomers during aggregation.

In some embodiments, preventing the formation of toxic amyloid oligomers is tested by a neuronal cell culture cytotoxicity assay. In this assay, differentiated N2a neuroblastoma cells or equivalents are coincubated with Aβ42 oligomers. The oligomers bind membranes and cause membrane perturbation and the leaking of cytosolic enzymes into the media. Prolonged incubation with high concentrations of oligomers will kill cells. When oligomers are pre-treated with phage or g3p prior to incubating with cells, the oligomers are at least less toxic and sometimes nontoxic. This neutralizing effect may be quantitated by measuring the release of adenylate kinase, one exemplary cytosolic enzyme released by the neuronal cells after membrane perturbation.

In some embodiments, a composition of the invention inhibits conversion of soluble prion protein into proteinase K resistant conformer in the protein misfolding cyclic amplification (PMCA) assay. Wang et al., Science, (2010) 327: 1132-35. In this assay, recombinant PrP is mixed with the lipid POPG and RNA in either the presence or absence of a composition of the invention. The material is then subjected to multiple (e.g., 48) cycles of a 30 second sonication followed by 29.5 minute incubation. A fraction of the reaction mixture is then used to seed another substrate tube and the cycle repeated. Each round is tested for the presence of proteinase K resistant material, which is indicative of the infectious form of PrP. Reduction in proteinase K resistant material in the presence of a composition of the invention indicates that the composition inhibits formation of the PK resistant conformer.

As noted above, amyloid forms of certain prion proteins, such as yeast prion protein NM, can also be detected in the filter trap assay. Accordingly, depending upon the prior protein, in some embodiments the ability of a composition of the invention to disaggregate prion protein aggregates may be tested in the filter trap assay.

In Vivo Functional Assays

In addition to activities such as increased binding affinity for amyloid or decrease in $T_M$, that can be demonstrated in in vitro assays, compositions of the invention may also reduce amyloid in one of several in vivo assays. One method for determining amyloid reduction in vivo uses positron emission tomography (PET) with the imaging agent florbetapir (F18-AV-45, Eli Lilly) before and after treatment to compare the number and/or distribution of β-amyloid. Of course, as additional biomarkers are identified, they may also be used to measure reduction of amyloid.

Another method of determining whether a composition reduces amyloid in vivo uses the hAPP mouse model. Rockenstein, J Neurosci Res. (2001) 66(4):573-82. These mice develop high levels of β-amyloid at an early age (3-4 months). The ability of a composition to reduce amyloid can be determined by injecting mice with a composition of the invention then comparing levels of amyloid in those mice compared to non-injected controls. It is also possible to inject a composition into only one hemisphere of an hAPP mouse, allowing comparison of amyloid levels between injected and non-injected hemispheres in the same mouse.

In another example, compositions of the invention are tested in the transgenic mouse model for Alzheimer's disease (TgAD) described in US2011/0142803, Hsiao et al., Science (1996) 274:99-102, or Duyckaerts et al., Acta Neuropathol (2008) 115:5-38. Briefly, wild-type, as well as transgenic mice, are challenged. To assess the potential of a composition of the invention to act as disaggregating agent, a composition is injected intracranially to transgenic mice (Taconic, APPSWE(2576), 10 month-old). For example, for compositions comprising phage, 2.5 µl the filamentous phage solution ($10^{14}$ phages/ml) are injected over 10 minutes (Bregma -2.8 mm, lateral 2.5 mm, ventral 2.5 mm) to one hemisphere, while to the contra-lateral side, phosphate-buffered-saline (PBS) is applied as a control. Treated mice are then sacrificed at different time points and brains post-fixed overnight in 4% paraformaldehyde, and cut using a microtome. Thioflavin-S (ThS) staining is performed to evaluate amyloid load. Sections are stained with Mayer's hematoxylin to quench nuclear autofluorescence and after washing ThS solution (1%) is applied for 3 minutes. Differentiation is done using 1% acetic acid for 20 min, and after washes the slides are dried and mounted with anti fade mounting medium. Amyloid load is calculated using LEICA Qwin program. Alternatively, amyloid load can be assessed with an anti-amyloid antibody.

Biodistribution of radioactive (e.g., $I^{125}$) or fluorescently labeled compositions, or unlabelled compositions, including filamentous phage, can also be measured to show that a composition binds amyloid in vivo. For example, when the composition comprises phage, the filamentous phage may be radioactively or fluorescently labeled. BALB/c mice are divided into groups. Each mouse then receives intranasally 100 μl of phage ($1.25 \times 10^{12}$ phage) over an hour. The first group of mice is sacrificed an hour after administration of intra-cardial perfusion using 4% paraformaldehyde. The second group is sacrificed 3 hours post-treatment, and the last group, after 24 hours. After perfusion, brains as well as peripheral organs are removed and the label is measured. Alternatively, unlabelled compositions or phage can be assessed for binding using similar methods but co-staining brain sections with a stain that recognizes amyloid and a stain that recognizes the composition or phage.

Intranasal administration of filamentous phage is also used to fully evaluate compositions comprising phage, such as phage comprising a mutant g3p or amyloid-binding fragment of g3p, or phage with an increased number of g3p relative to wild type phage, as provided by the invention. For example, phage are administered intranasally to SWE/APP2576 transgenic mice (Taconic, 10 month-old), a mouse model of Alzheimer's Disease. Twenty microliters of phage solution ($5 \times 10^{12}$/ml) are applied every two weeks, for 4 to 12 months and cognitive functions are evaluated. After the treatment period, a novel object recognition test is carried out to study the influence of phage treatment on memory improvement. On the first day, mice are exposed to two new objects for 20 minutes. On the following day, one object is replaced, and the curiosity of the mice to explore the novel item is tested. A recognition index is calculated for each mouse by dividing the time it spent near the new object by the total time spent near both objects. Thus, values above 0.5 are indicative for recognizing the old item and spending more time around the new object for its investigation.

Other transgenic models of protein misfolding disease may also be used to demonstrate that a composition of the invention reduces amyloid. Non limiting examples include the "D line" α-synuclein mice (a model of Parkinson's Disease, Masliah et al., Science (2000) 287:1265-1269); Tg2576 mice (a model of Alzheimer's Disease, Hsiao et al., Science (1996) 274:99-102 and Duyckaerts et al., Acta Neuropathol (2008) 115:5-38 at 9); various Jax® Mice for Parkinson's Disease Research (Jackson Laboratories, Bar Harbor, Me.); and mouse and rat models available from JSW Lifescience, including those for Parkinson's Disease, Alzheimer's Disease, Huntington's Disease.

Phage in which g3p has been rendered inactive are expected to be inactive in these assays, whereas wild type phage co-localize to amyloid, reduce amyloid load, prevent amyloid formation, and/or remove toxic oligomers and result in improvement in cognitive function. Phage comprising a g3p or an amyloid-binding fragment thereof, as provided by the invention, can thus be tested for in vivo activity relative to these negative and positive controls.

Pharmaceutical Compositions

In another aspect, the invention provides pharmaceutically acceptable compositions comprising any of the above-described agents of the invention (i.e., (a) g3p, amyloid binding fragments of g3p, or mutants or variants thereof; (b) compounds, polypeptides and fusion proteins comprising g3p, amyloid binding fragments of g3p, or mutants or variants thereof; (c) filamentous bacteriophage bearing an increased number of copies of g3p as compared to wild-type phage; (d) amyloid binding display vehicles bearing g3p, amyloid binding fragments of g3p, mutants or variants thereof, or compounds, polypeptides and fusion proteins comprising g3p, amyloid binding fragments of g3p, or mutants or variants thereof; or (e) modified filamentous phage bearing variants of g3p, amyloid binding fragments of g3p (not as part of a displayed g3p protein), mutants or variants of such binding fragments, or fusion proteins or other heterologous polypeptides that comprise g3p, amyloid binding fragments of g3p, or mutants or variants thereof).

A "pharmaceutical composition" refers to a therapeutically effective amount of a composition as described herein with a physiologically suitable carrier and/or excipient. A pharmaceutical composition does not cause significant irritation to an organism. The phrases "physiologically acceptable carrier" and "pharmaceutically acceptable carrier" which may be used interchangeably refer to a carrier or a diluent that does not cause significant irritation to an organism and does not abrogate the biological activity and properties of the administered composition.

The term "excipient" refers to an inert substance added to a pharmaceutical composition to further facilitate administration of an active ingredient. Examples, without limitation, include, for example, saline, calcium carbonate, calcium phosphate, various sugars and types of starch, cellulose derivatives, gelatin, vegetable oils, polyethylene glycols, and surfactants, including, for example, polysorbate 20.

Pharmaceutical compositions for use in accordance with the present invention may be formulated in a conventional manner using one or more physiologically acceptable carriers comprising excipients and auxiliaries, which facilitate processing of the active ingredients into compositions which can be used pharmaceutically. Proper formulation is dependent upon the route of administration chosen and upon the nature of the composition delivered (e.g., protein versus phage).

Suitable routes of administration for the pharmaceutical compositions of the invention may, for example, include transmucosal, especially transnasal delivery; parenteral delivery, including intramuscular, subcutaneous, intramedullary, intrathecal, intraventricular, intravenous, intraperitoneal, intranasal, or intraocular injections; oral; or rectal delivery.

In some embodiments, a pharmaceutical composition is administered in a local rather than systemic manner, for example, via injection of the pharmaceutical composition directly into the brain of a patient. In some embodiments, the injection technique is any technique that avoids the blood-brain barrier, for example, by direct intramedullary, intrathecal, or intraventricular injection.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

In some embodiments, a pharmaceutical composition of the invention is administered via intranasal administration. Intranasal delivery has been reported to enable the direct entry of viruses and macromolecules into the cerebrospinal fluid (CSF) or CNS. Mathison et al, 1998; Chou et al, 1997; Draghia et al, 1995.

For administration by the intranasal route, compositions are conveniently delivered in the form of an aerosol spray from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The various proteins described herein as components of pharmaceutical compositions may also be delivered to the brain using olfactory receptor neurons as a point of delivery. For example, an adenovirus vector comprising a gene encoding any of those proteins may be delivered via olfactory receptor neurons. Draghia et al, 1995.

The compositions described herein may be formulated for parenteral administration, e.g., by bolus injection or continuous infusion. Pharmaceutical compositions for parenteral administration include aqueous solutions of the composition in water-soluble form. Additionally, suspensions of the active ingredients may be prepared as oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents (e.g., surfactants such as polysorbate (Tween 20)) which increase the solubility of the active ingredients to allow for the preparation of highly concentrated solutions. A protein based agent such as, for example, albumin may be used to prevent adsorption of M13 to the delivery surface (i.e., IV bag, catheter, needle, etc.).

For oral administration, the compositions can be formulated readily by combining the active compounds with pharmaceutically acceptable carriers well known in the art.

Formulations may be presented in unit dosage form, e.g., in vials, ampoules or in multidose containers with optionally, an added preservative. The compositions may be suspensions, solutions or emulsions in oily or aqueous vehicles, and may contain formulatory agents such as suspending, stabilizing and/or dispersing agents. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, such as by infusion, or via an implanted pump, such as an ICV pump. In the latter embodiment, the single dosage form may be an infusion bag or pump reservoir pre-filled with the indicated number of filamentous bacteriophage. Alternatively, the infusion bag or pump reservoir may be prepared just prior to administration to a patient by mixing a single dose of the filamentous bacteriophage with the infusion bag or pump reservoir solution.

Another aspect of the invention includes methods for preparing a pharmaceutical composition of the invention. Techniques for formulation of drugs may be found, for example, in "Remington's Pharmaceutical Sciences," Mack Publishing Co., Easton, Pa., latest edition, which is incorporated herein by reference in its entirety.

Pharmaceutical compositions suitable for use in the context of the present invention include compositions wherein the active ingredients are contained in an amount effective to achieve the intended purpose.

Determination of a therapeutically or diagnostically effective amount is well within the capability of those skilled in the art, especially in light of the detailed disclosure provided herein.

Dosage amount and interval may be adjusted individually to provide brain levels of the phage display vehicle which are sufficient to treat or diagnose a particular brain disease, disorder, or condition (minimal effective concentration, MEC). The MEC will vary for each preparation, but can be estimated from in vitro data. Dosages necessary to achieve the MEC will depend on individual characteristics.

Dosage intervals can also be determined using the MEC value. Preparations should be administered using a regimen, which maintains brain levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated or diagnosed, the severity of the affliction, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is to be understood that both the foregoing and following description are exemplary and explanatory only and are not restrictive of the invention, as claimed.

Therapeutic Uses

As noted, filamentous bacteriophage M13, and related filamentous phage, have shown utility in animal models of protein misfolding disease. See United States patent publication US 2011/0142803, incorporated by reference herein in its entirety. In particular, it has been discovered that filamentous bacteriophage have the ability to disaggregate amyloid that have already formed in the brain. Removal of amyloid is expected to reduce, slow the progression of, or even to reverse the symptoms associated with a variety of diseases characterized by misfolded and/or aggregated proteins in the brain. See, e.g., WO2006083795 and WO2010060073, incorporated by reference herein in their entirety.

Further, M13 has been shown to disaggregate at least four different amyloid fibers: amyloid-β 1-42 fibers (fAβ42), α-synuclein fibers (fαsyn), yeast prion NM fibers (fNM), and tau fibers (ftau).

Accordingly, another aspect of the invention relates to the use of any of the compositions of the invention, such as those comprising g3p, N1N2 domain, N2 domain or other amyloid-binding fragments (including mutants or variants of all of the foregoing), or g3p fusion proteins, display vehicles, or phage comprising any of the above, in the treatment of protein misfolding diseases, including, but not limited to, those diseases involving any of fAβ42, fαsyn, fNM, or ftau.

In the context of treatments, the terms "patient", "subject" and "recipient" are used interchangeably and include humans as well as other mammals. In some embodiments, a patient is a human who is positive for a biomarker associated with a protein misfolding disease. In one embodiment, the patient exhibits β-amyloid deposits as detected by PET imaging with florbetapir.

The term "treating" is intended to mean reducing, slowing, or reversing the progression of a disease in a patient exhibiting one or more clinical symptoms of a disease. "Treating" is also intended to mean reducing, slowing, or reversing the symptoms of a disease in a patient exhibiting one more clinical symptoms of a disease. In one embodiment, the patient exhibits β-amyloid deposits as detected by PET imaging with florbetapir and the number of β-amyloid deposits is reduced by the treatment. In one embodiment, the patient exhibits β-amyloid deposits as detected by the g3p compositions of the present invention and the number of β-amyloid deposits are reduced or maintained by the treatment. In another embodiment, the patient exhibits any type of amyloid deposits as detected by PET imaging and the cognitive function of the patient is improved by the treatment. Improvement in cognitive function may be assayed by the methods and tests of McKhann et al., Alzheimer's & Dementia (2011) May; 7(3):263-9.

"Prophylaxis" is distinct from treating and refers to administration of a composition to an individual before the onset of any clinical symptoms. Prophylaxis using any of the g3p and/or ToIA compositions of the present invention is encompassed. Prophylaxis may be implicated in individuals who are known to be at increased risk for a disease, or whom are certain to develop a disease, solely on the basis of one or more genetic markers. Many genetic markers have been identified for the various protein misfolding diseases. For examples, individuals with one or more of the Swedish mutation, the Indiana mutation, or the London mutation in human amyloid precursor protein (hAPP) are at increased risk for developing early-onset Alzheimer's Disease and so are candidates for prophylaxis. Likewise, individuals with the trinucleotide CAG repeat in the huntingtin gene, particularly those with 36 or more repeats, will eventually develop Huntington's Disease and so are candidates for prophylaxis.

In some embodiments, a protein or fragment is used directly as a therapeutic. In these embodiments, a g3p, N1N2 domain, N2 domain, or other amyloid-binding fragments (including mutants or variants of any of the foregoing) is directly incorporated into a pharmaceutical composition or formulation. In other embodiments, a g3p, N1N2 domain, N2 domain, or other amyloid-binding fragment (including mutants or variants of any of the foregoing) is part of a fusion protein or display vehicle, such as a phage, and in these embodiments it is the fusion protein or display vehicle that is incorporated into a pharmaceutical composition or formulation of the invention. In other embodiments, the composition comprises a phage comprising g3p or amyloid binding fragment thereof that is more efficacious than g3p of wild type M13 phage in reducing or maintaining levels of amyloid. In some embodiments, the phage that is more efficacious in reducing or maintaining levels of amyloid than M13 expresses more than 5 copies of a g3p.

The term "protein misfolding" refers to diseases characterized by formation of amyloid protein by an aggregating protein (amyloid forming peptide), such as, but not limited to, β-amyloid, serum amyloid A, cystatin C, IgG kappa light chain, or a prion protein. Diseases known to be associated with misfolded and/or aggregated amyloid protein include Alzheimer's disease, which includes early onset Alzheimer's disease, late onset Alzheimer's disease, and presymptomatic Alzheimer's disease, Parkinson's disease, SAA amyloidosis, cystatin C, hereditary Icelandic syndrome, senility, multiple myeloma, prion diseases including but not limited to kuru, Creutzfeldt-Jakob disease (CJD), Gerstmann-Straussler-Scheinker disease (GSS), fatal familial insomnia (FFI), scrapie, and bovine spongiform encephalitis (BSE); amyotrophic lateral sclerosis (ALS), spinocerebellar ataxia (SCA1), (SCA3), (SCA6), (SCA7), Huntington disease, entatorubral-pallidoluysian atrophy, spinal and bulbar muscular atrophy, hereditary cerebral amyloid angiopathy, familial amyloidosis, frontotemporal lobe dementia, British/Danish dementia, and familial encephalopathy. The g3p compositions of the invention may be used to treat "protein misfolding" diseases.

Many of these misfolded and/or aggregated amyloid protein diseases occur in the central nervous system (CNS). Some examples of diseases occurring in the CNS are Parkinson's Disease; Alzheimer's Disease; frontotemporal dementia (FTD) including those patients having the following clinical syndromes: behavioral variant FTD (bvFTD), progressive non-fluent aphasia (PNFA) and semantic dementia (SD); frontotemporal lobar degenerations (FTLDs), and Huntington's Disease. The g3p compositions of the invention may be used to treat diseases characterized by misfolded and/or aggregated amyloid protein that occur in the central nervous system (CNS).

Misfolding and/or aggregation of proteins may also occur outside the CNS. Amyloidosis A (AA) (for which the precursor protein is serum acute phase apolipoprotein, SAA) and multiple myeloma (precursor proteins immunoglobulin light and/or heavy chain) are two widely known protein misfolding and/or aggregated protein diseases that occur outside the CNS. Other examples include disease involving amyloid formed by $β_2$-microglobulin, transthyretin (Familial Amyloidotic Polyneuropathy [FAP], Familial Amyloidotic Cardiomyopathy [FAC], and Senile Systemic Amyloidosis [SSA]), (apo)serum AA, apolipoproteins AI, AII, and AIV, gelsolin (Finnish form of Familial Amyloidotic Polyneuropathy), lysozyme, firbrinogen, cystatin C (Cerebral Amyloid Angiopathy, Hereditary Cerebral Hemorrhage with Amyloidosis, Icelandic Type), (pro)calcitonin, islet amyloid polypeptide (IAPP amyloidosis), atrial natriuretic factor, prolactin, insulin, lactadherin, kerato-epithelin, lactoferrin, odontogenic ameloblast-associated protein, and semenogelin I. The g3p compositions of the invention may be used to treat diseases involving misfolding and/or aggregation of proteins that occur outside the CNS.

Neurodegenerative diseases may also involve tau lesions. (Reviewed in Lee et al. (2001) Annu. Rev. Neurosci. 24:1121-159). Tau proteins are microtubule-associated proteins expressed in axons of both central and peripheral nervous system neurons. Neurodegenerative tauopathies (sometimes referred to as tauopathies) are encompassed. Examples of tauopathies include Alzheimer's Disease, Amyotrophic lateral sclerosis/parkinsonism-dementia complex, Argyrophilic grain dementia, Corticobasal degeneration, Creutzfeldt-Jakob disease, Dementia pugilistica, diffuse neurofibrillary tangles with calcification, Down's syndrome, Frontotemporal dementias including frontotemporal dementia with parkinsonism linked to chromosome 17, Gerstmann-Sträussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, and Tangle only dementia. Some of these diseases may also include deposits of fibrillar amyloid β peptides. For example, Alzheimer's disease exhibits both amyloid β deposits and tau lesions. Similarly, prion-mediated diseases such as Creutzfeldt-Jakob disease, prion protein cerebral amyloid angiopathy, and Gerstmann-Sträussler-Scheinker syndrome may have also have tau lesions. Thus an indication that a disease is a "tauopathy" should not be interpreted as excluding the disease from other neurodegenerative disease classifications or groupings, which are provided merely as a convenience. The g3p compositions of the invention may be used to treat neurodegenerative diseases as well as diseases involving tau lesions.

In one embodiment, a pharmaceutical composition or formulation is for use in a method of reducing amyloid in a patient exhibiting symptoms related to the presence of amyloid or that is positive for a biomarker associated with a protein misfolding disease, such as florbetapir (AV-45, Eli Lilly), comprising administering to the patient an effective amount of a pharmaceutical composition or formulation as described herein. In one embodiment, the route of administration is selected from intrathecal injection, direct intraventricular injection, intraparenchymal injection, or intranasal delivery.

In one embodiment, a pharmaceutical composition or formulation is for use in a method of maintaining the level of amyloid in a patient exhibiting symptoms related to the presence of amyloid or that is positive for a biomarker associated with a protein misfolding disease, such as florbetapir (AV-45, Eli Lilly), comprising administering to the patient an effective amount of a pharmaceutical composition or formulation as described herein. In one embodiment, the route of administration is selected from intrathecal injection, direct intraventricular injection, intraparenchymal injection, or intranasal delivery.

In one embodiment, a pharmaceutical composition or formulation is for use in a method of disaggregating amyloid in a patient comprising administering to a patient having amyloid an effective amount of a pharmaceutical composition or formulation as described herein. In one embodiment, the route of administration is selected from intrathecal injection, direct intraventricular injection, intraparenchymal injection, or intranasal delivery.

In one embodiment, a pharmaceutical composition or formulation is for use in a method of causing the disaggregation of β-amyloid deposits in the brain, comprising injecting directly into the brain of a patient in need thereof an effective amount of pharmaceutical composition as described herein, thereby causing a reduction in β-amyloid deposits in the brain.

In one embodiment, a pharmaceutical composition or formulation is for use in a method of reducing amyloid formation in the brain. Reducing amyloid formation in the brain may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery.

In one embodiment, a pharmaceutical composition or formulation of the invention is for use in a method for promoting amyloid clearance in the brain. Promoting amyloid clearance may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery.

In one embodiment, a pharmaceutical composition or formulation of the invention is for use in a method for inhibiting amyloid aggregation in the brain. Inhibiting amyloid aggregation in the brain may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery.

In one embodiment, a pharmaceutical composition or formulation of the invention is for use in a method for clearing toxic amyloid oligomers in the brain. Clearing toxic amyloid oligomers in the brain may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery.

In one embodiment, a pharmaceutical composition or formulation of the invention is for use in a method for preventing the formation of toxic amyloid oligomers in the brain. Preventing the formation of toxic oligomers in the brain may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery.

In one embodiment, a pharmaceutical composition or formulation of the invention is for use in a method for protecting neurons from amyloid damage. Protecting neurons from amyloid damage may prevent, treat or reduce the symptoms or severity of a protein-misfolding or neurodegenerative disease. In one embodiment, the route of administration is selected from intrathecal injection, direct intraventricular injection, intraparenchymal injection, or intranasal delivery. In one embodiment, a pharmaceutical composition or formulation of the invention for use in protecting neurons from amyloid damage is given prophylactically.

In some embodiments, the patient is positive for a biomarker associated with a protein misfolding and/or aggregation disease. In one embodiment, the biomarker is florbetapir (AV45, Eli Lilly).

In some embodiments, the patient is exhibiting symptoms of a neurodegenerative disease that is associated with the presence of amyloid. In various embodiments, the amyloid is any of fAβ42, fαsyn, fNM, or ftau.

In certain embodiments, the neurodegenerative disease is Parkinson's disease, Alzheimer's disease, or Huntington's disease. In one embodiment, the neurodegenerative disease is Alzheimer's disease. In one embodiment, the neurodegenerative disease is Alzheimer's disease and the patient exhibits β-amyloid as detected by the imaging agent florbetapir (AV-45, Eli Lilly).

In some embodiments, the patient is exhibiting symptoms of a prion-mediated disease.

In certain embodiments, the prion-mediated disease is chosen from Creutzfeldt-Jakob disease, kuru, fatal familial insomnia, or Gerstmann-Sträussler-Scheinker syndrome.

In some embodiments, the patient is exhibiting symptoms of a neurodegenerative tauopathy other than Alzheimer's disease. In certain embodiments, the disease to be treated is selected from Argyrophilic grain dementia, Corticobasal degeneration, Dementia pugilistica, diffuse neurofibrillary tangles with calcification, Down's syndrome, Frontotemporal dementias including frontotemporal dementia with parkinsonism linked to chromosome 17, Hallervorden-Spatz disease, Myotonic dystrophy, Niemann-Pick disease type C, Non-Guamanian motor neuron disease with neurofibrillary tangles, Pick's disease, Postencephalitic parkinsonism, Progressive subcortical gliosis, Progressive supranuclear palsy, Subacute sclerosing panencephalitis, and Tangle only dementia.

Diagnostics

In another aspect of the invention, the g3p and ToIA compositions described herein, including g3p fusion proteins, are used in diagnostic applications associated with the various diseases described herein. For example, binding of a composition of the invention when used as an imaging agent either in vivo or in vitro may be part of a diagnosis of one of the protein misfolding diseases described.

Diagnostic agents, otherwise referred to herein as diagnostic compositions, are encompassed, and may comprise any of the above-described agents of the invention (i.e., (a) g3p, amyloid binding fragments of g3p, or mutants or variants thereof; (b) compounds, polypeptides and fusion proteins comprising g3p, amyloid binding fragments of g3p, or mutants or variants thereof; (c) filamentous bacteriophage bearing an increased number of copies of g3p as compared to wild-type phage; (d) amyloid binding display vehicles bearing g3p, amyloid binding fragments of g3p, mutants or variants thereof, or compounds, polypeptides and fusion proteins comprising g3p, amyloid binding fragments of g3p, or mutants or variants thereof; or (e) modified filamentous phage bearing variants of g3p, amyloid binding fragments of g3p (not as part of a displayed g3p protein), mutants or variants of such binding fragments, or fusion proteins or other heterologous polypeptides that comprise g3p, amyloid binding fragments of g3p, or mutants or variants thereof). The diagnostic agent may further comprise a detectable label, or may be otherwise detected in vivo.

In some embodiments, a composition of the invention, such as one comprising a soluble g3p or an amyloid binding fragment (including mutants and variants thereof), or a g3p fusion protein, is used as an amyloid imaging agent. The imaging agent can detect amyloid and diagnose diseases associated with amyloid. Because the compositions of the invention bind amyloid irrespective of the type of fiber, they are advantageous in that they can image any amyloid aggregate (Aβ, tau, α-synuclein, etc.)—all with a single imaging agent. At present, there are no acceptable imaging agents/methods for tau or alpha synuclein aggregates in the CNS. And while imaging agents for β-amyloid exist, there is still a need for additional agents that may provide improved correlation between cognitive function and imaging results and/or that better predict which patients will deteriorate versus remain stable. For a review, see Resnick & Sojkova, Alzheimer's Res Ther. (2011) 3(1):3.

The diagnostic compositions of the invention may be used as imaging agents in combination with an imaging agent that is specific for β-amyloid such as, for example, F18-AV-45, Eli Lilly. Since there are currently no known imaging agents for non-β-amyloid aggregates, the use of a diagnostic composition of the invention together with a β-amyloid-specific imaging agent will result in the detection of non-β-amyloid aggregates based on differential detection. Thus, in one embodiment, a diagnostic composition of the invention is used as an imaging agent in combination with a β-amyloid imaging agent to detect nonβ-amyloid aggregates.

In another embodiment, a diagnostic composition of the invention is used as an imaging agent to detect β-amyloid in the CNS, including the brain.

A diagnostic composition of the invention generally requires that the amyloid-binding component be attached to one or more detectable labels when it is used as an imaging agent. Various labels can be attached to the amyloid binding component of the diagnostic composition using standard techniques for labeling proteins. Examples of labels include fluorescent labels and radiolabels. There are a wide variety of radiolabels that can be used, but in general the label is often selected from radiolabels including, but not limited to, $^{18}F$, $^{11}C$, and $^{123}I$. These and other radioisotopes can be attached to the protein using well known chemistry. In one embodiment, the label is detected using positron emission tomography (PET). However, any other suitable technique for detection of radioisotopes may also be used to detect the radiotracer.

Diagnostic compositions of the invention may be administered using the same routes described for therapeutic compositions. In one embodiment, intrathecal administration is used as the route for administering the diagnostic composition. In another embodiment, intravenous administration is used as the route for administering the diagnostic composition.

EXAMPLES

Although the demonstrated therapeutic efficacy of filamentous phage as binding and anti-aggregation agents is not contingent upon any particular mechanism of action, understanding the mechanism permits the design of phage with greater therapeutic efficacy. In addition, it serves as a basis for preparing additional anti-aggregation agents.

As noted previously, M13 has been shown to bind to and disaggregate at least four different amyloid fibers: amyloid-β-42 fibers (fAβ42), α-synuclein fibers (fαsyn), yeast prion NM fibers (fNM), and tau fibers (ftau). The four proteins that make up these amyloid fibers have unrelated primary amino acid sequence, but all four are misfolded into the canonical amyloid fold. Eichner & Radford, 2011. The ability of M13 to bind to and mediate disaggregation of each of these indicates that M13 recognizes a structural motif, such as cross-beta sheet conformation or a conformational feature such as hydrophobic groves, both of which are defining characteristics of all amyloid fibers.

But amyloid disaggregation is not a general property of all phage. For example, the structurally distinct icosahedral phage T7 does not mediate disaggregation of fAβ42, even when T7 is incubated with fAβ42 for 3 days at 37° C. Bacteriophage T7 did not show any dissociation activity even at concentrations at which M13 dissociates over 70% of the co-incubated amyloid fibers. In contrast, the bacteriophage fd, which carries a negatively charged amino acid in its g8p compared to M13 (and therefore displays 2800 more negative charges/phage than M13 given the copy number of g8p), bound and disaggregated fAβ42 similar to M13. These initial studies, along with the finding that amyloid disaggregation could also be mediated by tobacco mosaic virus (TMV) E. coli pili, and the tail tubes of T4, all of which also have a helical cylinder shape and repeating units (see US 2011/0182948), suggested that it may be the shape of the phage that is critical for its amyloid fiber-disassociation activity.

However, the following examples describe an alternate (although not mutually exclusive) mechanism for the reported binding and anti-aggregation property of filamentous phage. Based on these examples and the mechanism of action they support, modified phage with improved binding to amyloid are provided along with new amyloid-binding agents.

Example 1: M13 Phage Preferentially Binds Aβ Fibrils

Binding of M13 to Aβ fibrils versus Aβ monomers was determined by surface plasmon resonance (SPR).

Figures 3A, 3B:
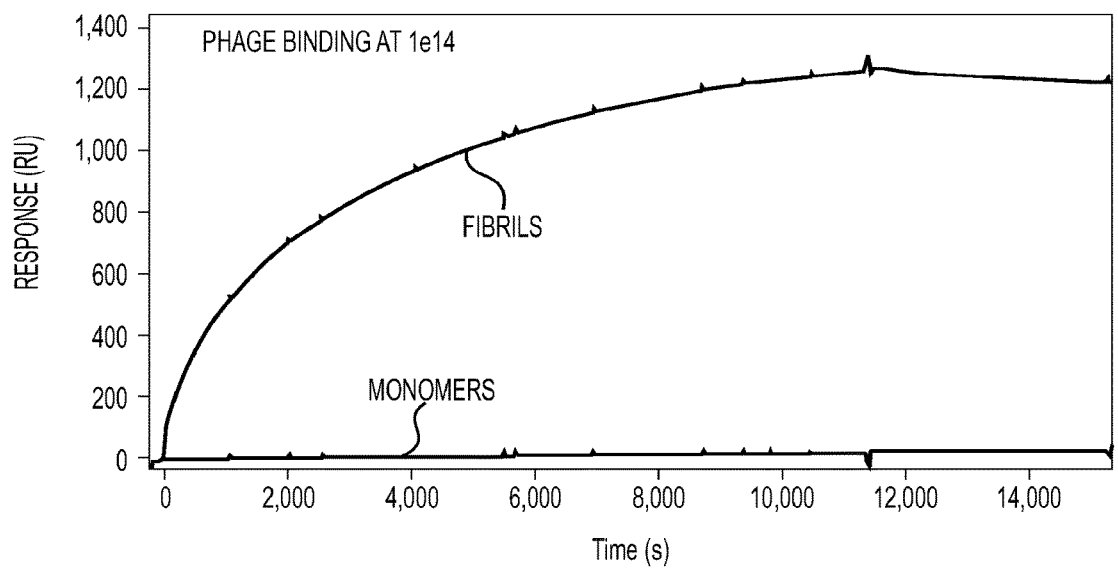
FIG. 3A presents a surface plasmon resonance (SPR) study of phage binding. Binding to Aβ fibrils was compared to binding to Aβ monomers using $10^{14}$ phage/mL flowed across the biosensor chip.
FIG. 3B shows the $K_a$, $K_d$, and $K_D$ calculated from the SPR data shown in FIG. 3A.

M13 phage preferentially binds Aβ fibrils; it does not bind Aβ monomers. Surface plasmon resonance studies using $10^{14}$ phage/mL flowed across a biosensor chip with immobilized fAβ are reported in FIG. 3. FIG. 3 shows that the $K_D$ of M13 binding is about 4 nM, which is comparable to binding by a monoclonal antibody. This high affinity interaction indicates that a specific binding process is occurring between phage and the amyloid fiber.

Example 2: Binding of M13 to Ab Fibrils is Dose Dependant

Figure 4A:
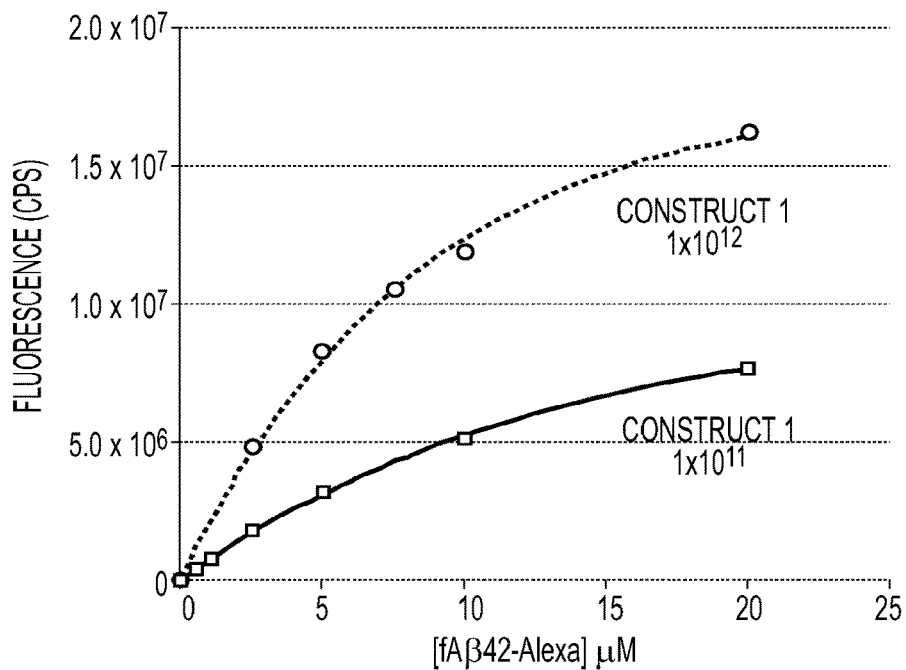
FIGS. 4A and 4B present binding studies.
Figure 4B:
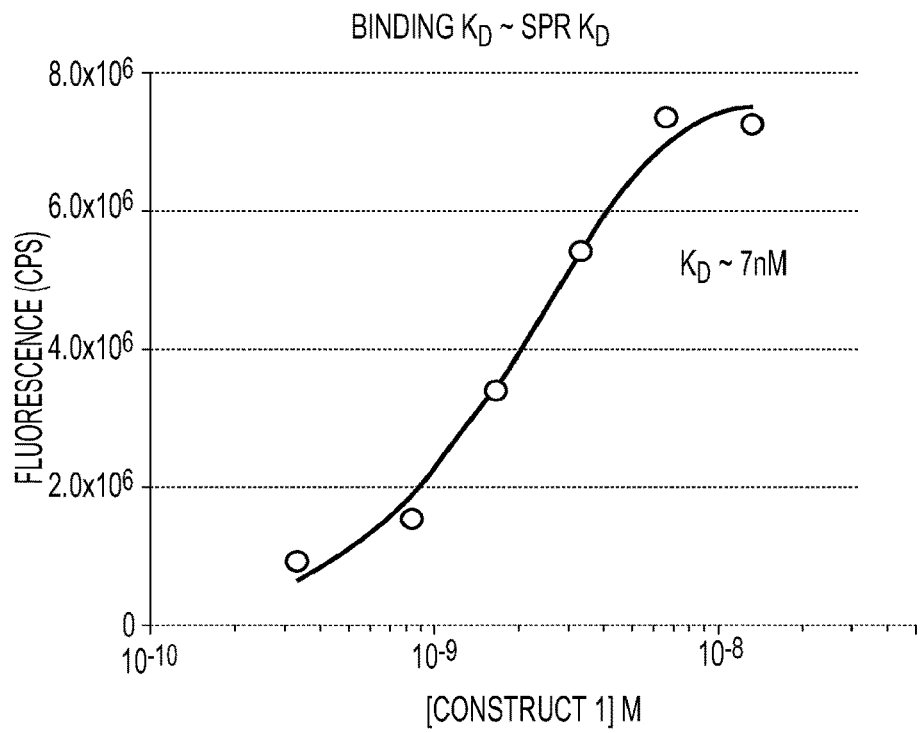

M13 binding to fAβ42 is also dose dependent. In FIG. 4A, the binding of two phage doses with increasing molar amounts of fAβ42 was compared. In this M13-Amyloid fiber binding assay, M13-Alexa488 was mixed with Aβ (fAβ) for 2-3 hours to allow complexes to form, then the complex sedimented by centrifugation at 7500 rpm for 10 minutes. The fluorescence in the pellet was proportional to the M13 bound to the amyloid. This assay provides both a quantitative measure of binding of phage to fAβ and provides a system for assessing the ability of other agents to compete with phage for binding. FIG. 4B shows that the $K_D$ for M13 binding competition is similar to that observed for binding using surface plasmon resonance.

Example 3: Binding of M13 to Aβ Fibrils Requires Native Conformation

Figure 5:
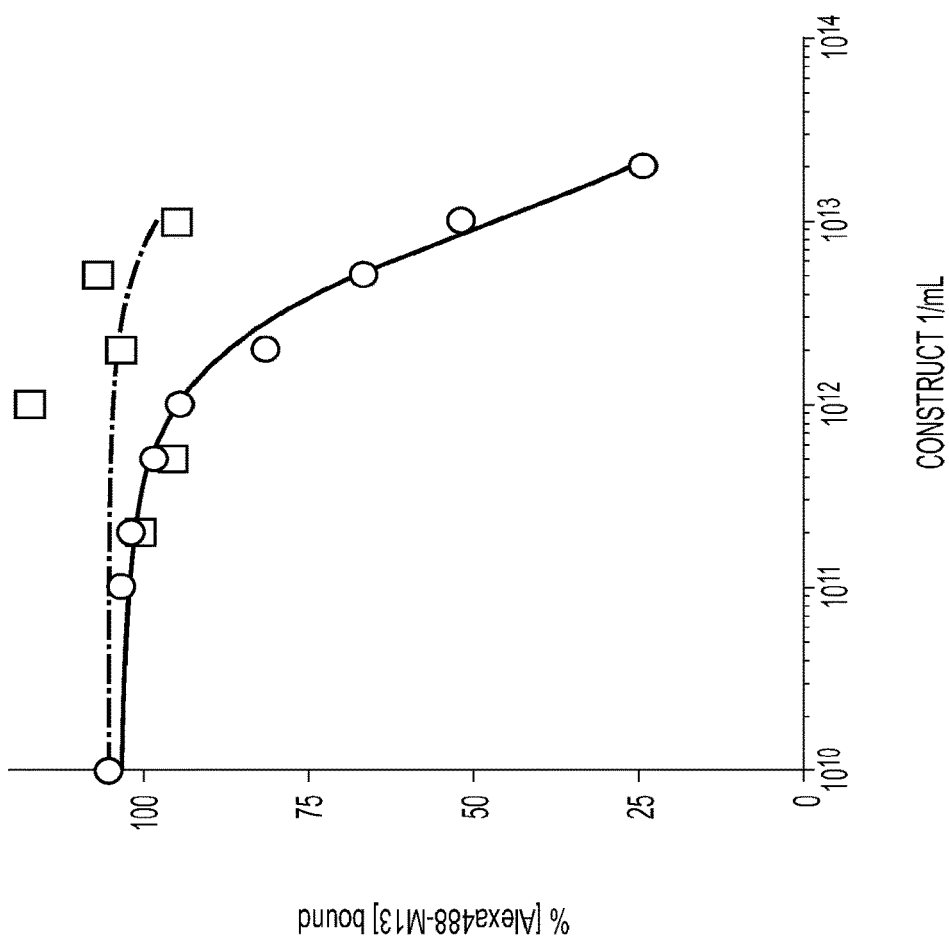
FIG. 5 shows binding competition results using heat denatured (boxes –90° C. for 10 minutes) versus native conformation (circles) M13 (Construct 1) in the amyloid fiber binding competition assay.

When M13 phage is heated at 90° C. for 10 minutes, its ability to compete for binding is essentially abrogated. FIG. 5 shows binding competition results using heat treated (boxes) versus native conformation (circles) M13 in the amyloid fiber competition binding assay.

Example 4: Temperature Correlates with M13-Amyloid Interactions

Figure 6:
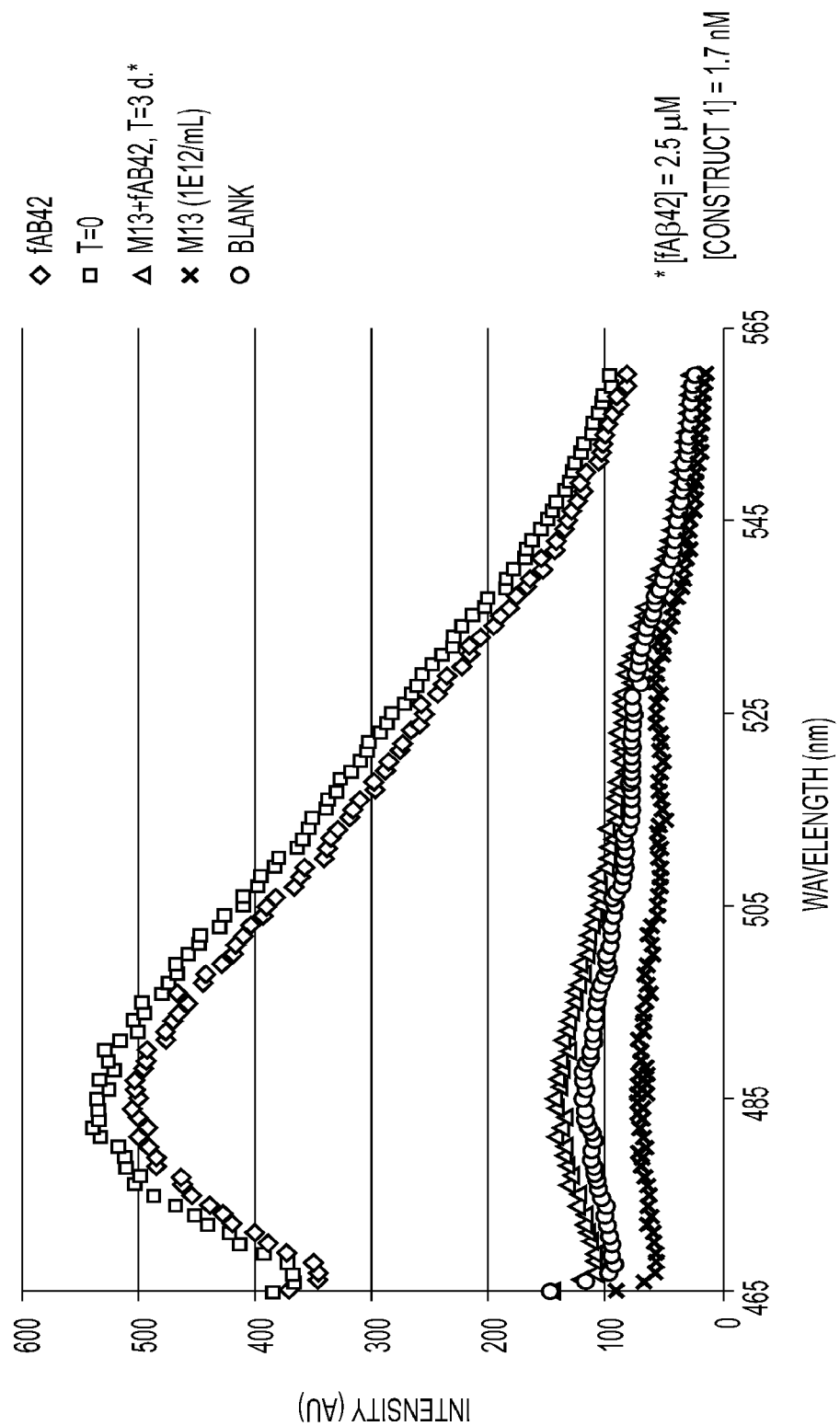
FIG. 6 shows a Thioflavin T (ThT) fluorescence assay using fAβ42 incubated in the presence or absence of 2 concentrations of M13 phage (Construct 1).

M13 potently disaggregates amyloid fibers. FIG. 6 shows a Thioflavin T (ThT) fluorescence assay using fAβ. In the presence of M13, fAβ42 disaggregates.

FIG. 7A shows that changing the salt concentration in the ThT fluorescence 10 fold (from 0.15 to 1.5 M) results in only a 2-3 fold difference in the percentage of fAβ that is disaggregated. This indicates that hydrophobic interactions are responsible for most of the disaggregation observed.

In contrast to the relatively minor effect of salt concentration, FIG. 7B shows that changing the temperature from 4° C. to 37° C. results in an 8-10 fold difference in disaggregation.

These results indicate that M13 disaggregation is dependent on a protein that is more active at a higher temperature and that is relatively insensitive to the effect of salt in the assay, implying a hydrophobic interaction. Phage g3p fits this description. Its N1 and N2 domains are linked by a flexible glycine-rich linker that "opens" up following binding of N2 to the bacterial F-pilus. N1 is then available for binding a bacterial co-receptor as part of the infection process. Increasing the temperature in the disaggregation assay is expected to "open" up the N2 and N1 domains of g3p.

Figure 8A:
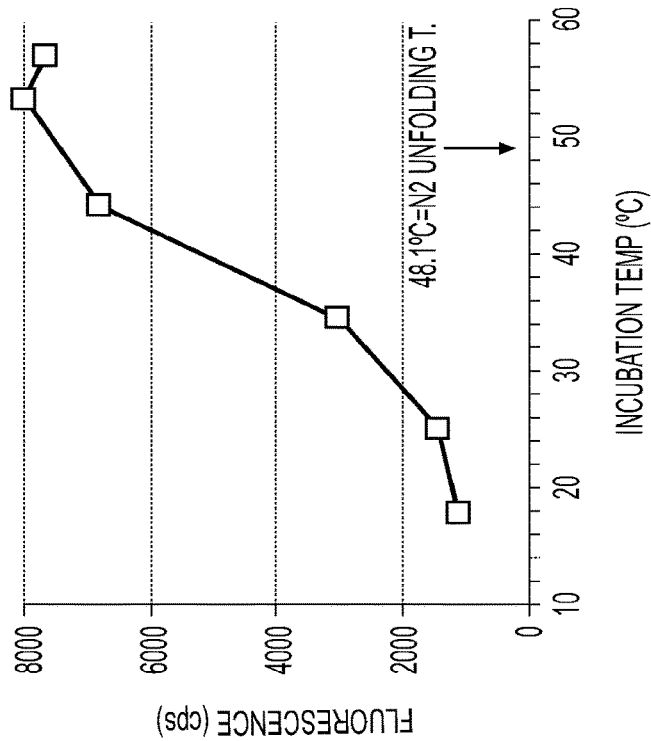
FIGS. 8A and 8B represent M13-amyloid binding assays using fAβ42.
Figure 8B:
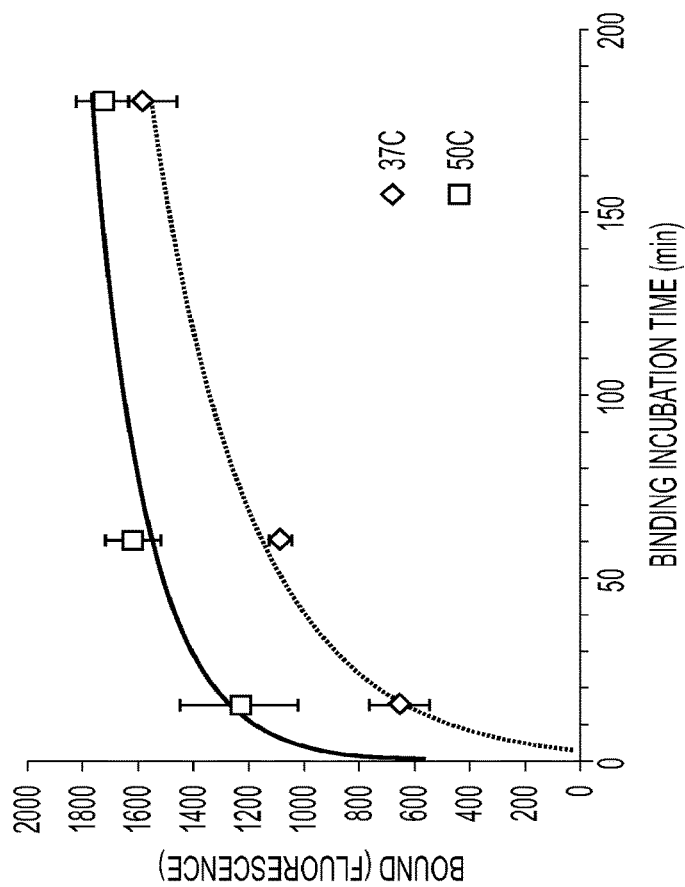

While inactivating M13 at high temperature (90° C., 10 minutes, see FIG. 5) abrogates binding, increasing the incubation temperature in the M13-amyloid binding assay has a positive effect on binding. FIG. 8A shows that increasing the temperature from 18° C. to 58° C. results in progressively better binding up to about the hinge unfolding $T_M$ of about 50° C., at which point binding begins to decrease. This optimal binding temperature is consistent with the temperature of the N1-N2 unfolding (the so-called melting temperature, or $T_M$) in g3p, which is 48.1° C. Increasing the incubation temperature to 50° C. vs 37° C. also results in more rapid binding of M13 to fAβ42. FIG. 8B.

Example 5: g3p is Required for M13-β-Amyloid Interaction

To directly test whether g3p is required for M13-β-amyloid interaction, g3p was removed from phage by proteolytic treatment with ArgC (M13Δg3p) and the M13Δg3p phage compared to refolded phage for Aβ binding. Treatment with ArgC, a *Bacillus* protease, selectively removes the g3p subunits from phage. The results are presented in FIG. 9A. Refolded M13 still competes with wildtype M13 in the competition binding assay, albeit at a decreased level. However, even 15 fold of M13Δg3p competed poorly, if at all with wildtype M13. This inability to compete with wild type M13 is consistent with a loss of infectivity in the M13Δg3p phage. FIG. 9B. ArgC treatment also caused a loss of disaggregation activity. FIG. 9C.

Figure 10A:
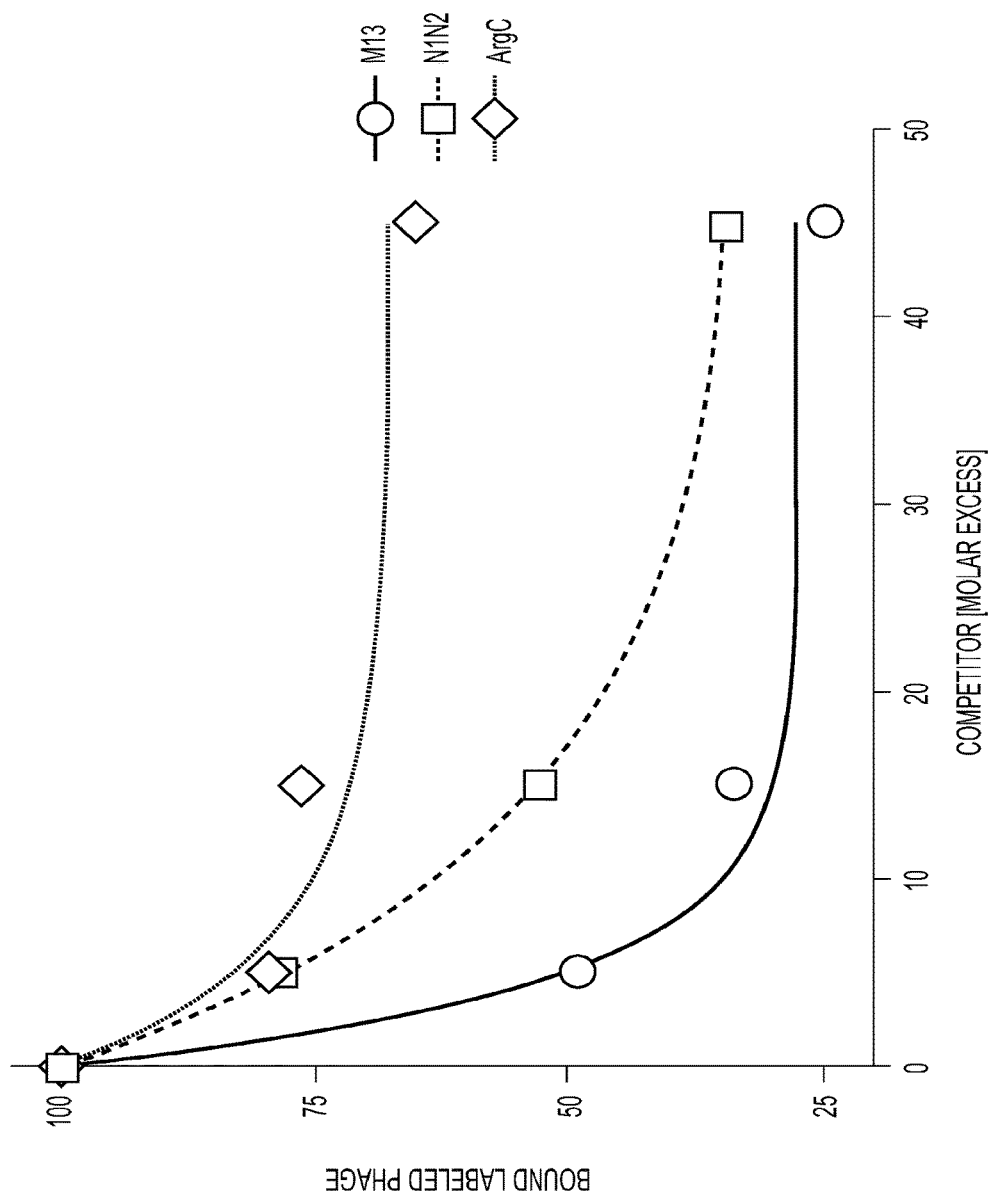
FIGS. 10A and 10B present the results of a binding competition assay using a N1-N2 fragment of g3p, herein referred to as recombinant soluble N1N2 (rs-g3p(N1N2); "Construct 3"), M13Δg3p (Arg C treated), and M13 as competitors of labeled M13 binding to fAβ42.
Figure 10B:
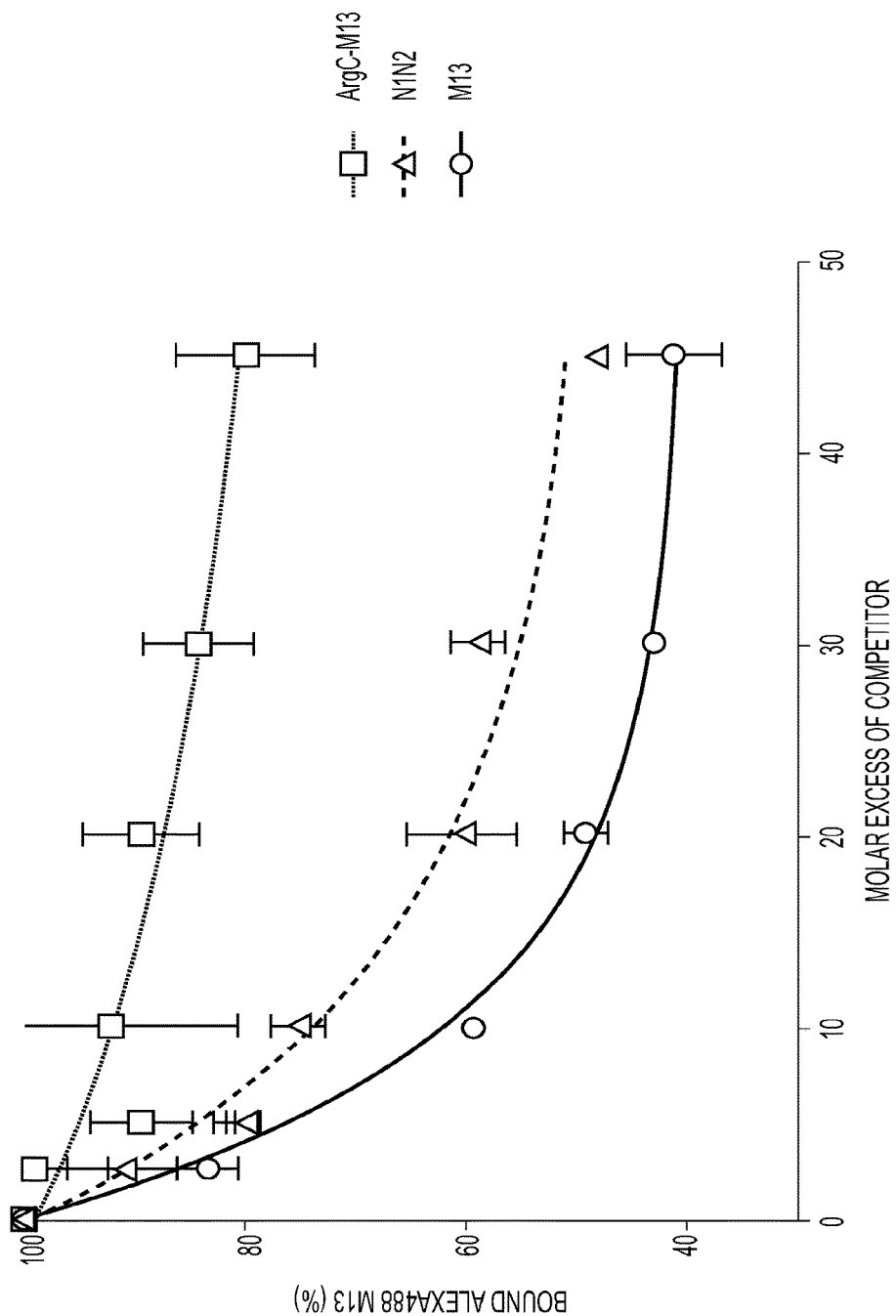

If g3p is mediating binding in a manner analogous to its role in infection, then the N1 and N2 domains that are important for infection should also compete with M13 for binding. To test this, recombinant soluble N1N2 ("rs-g3p (N1N2)"; "Construct 3") was prepared and tested in the competition assay. As shown in FIGS. 10A and 10B, M13 competes with the labeled M13 for binding to fAβ42, but M13Δg3p does not. In contrast, rs-g3p(N1N2) was able to compete with M13, indicating that the N1 and N2 domains of g3p are sufficient for β-amyloid binding. Similar results were obtained in a repeat of the competition assay. FIG. 10B.

Example 6: g3p Hinge Unfolding Mutations Modulate Amyloid Binding

Mutations that affect the ability of the hinge between the N1 and N2 domains of g3p to open up should also affect the ability of phage bearing those mutations to compete with wildtype M13 for binding to Aβ. Eckert & Schmid, 2007, described several variant phage that were used to test this hypothesis. Variant "AAA" (also known as "3A") impairs pilus binding and decreases the stability of the N2 domain. AAA carries the following mutations in g3p: W181A, F190A, and F194A. IIHY contains the mutations T13I, T101I, Q129H, and D209Y, which stabilize the N2 domain and increase $T_M$.

Figure 11:
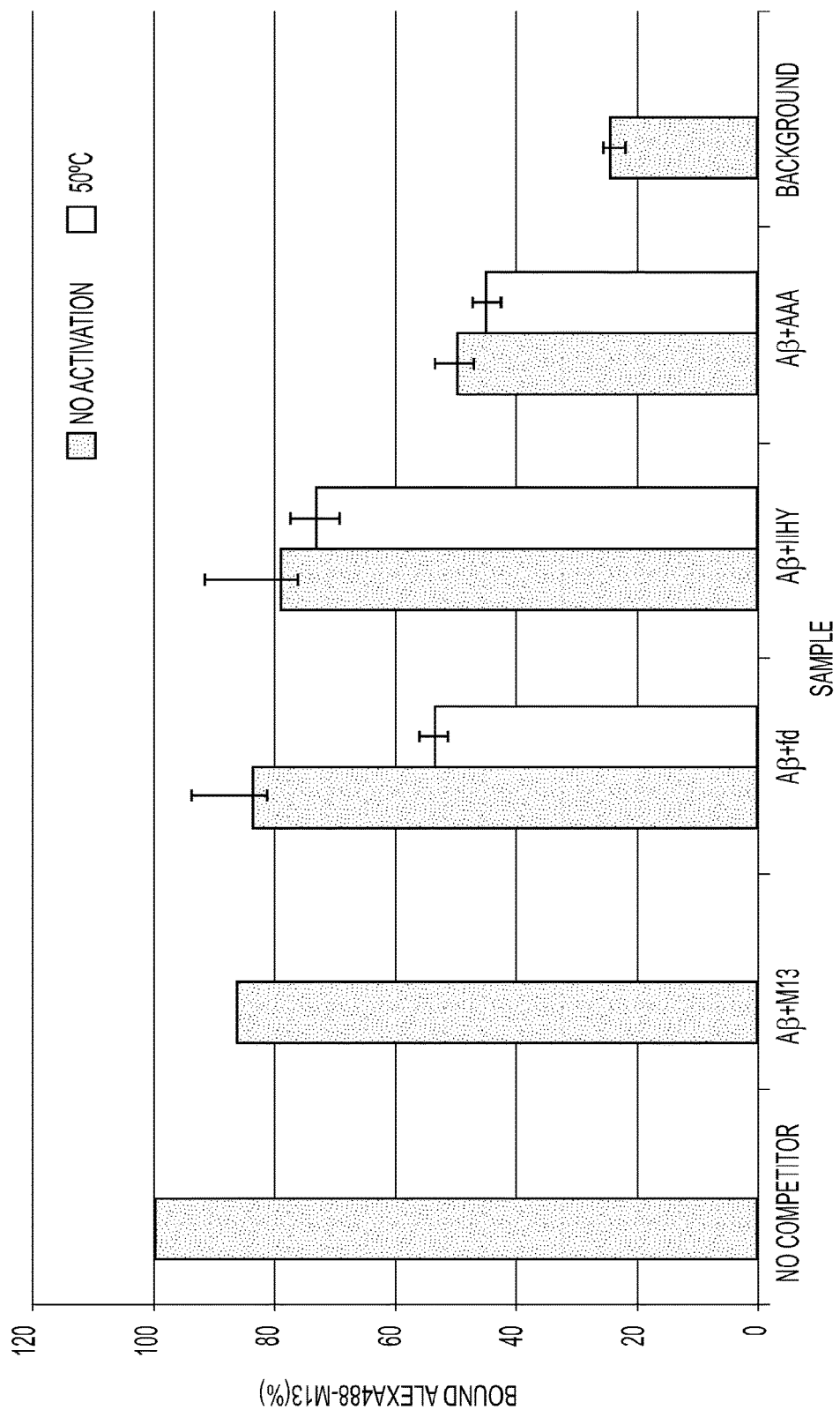
FIG. 11 presents competition data for phage fd, IIHY, AAA, and M13. Phages fd, AAA, and IIHY were pre-activated at 50° C. for 1.5 hours, then activated and non-activated Fd, AAA, & IIHY were compared for their ability to compete with labeled M13 for binding to Aβ during a 45 minute incubation at 37° C.
Figure 12C:
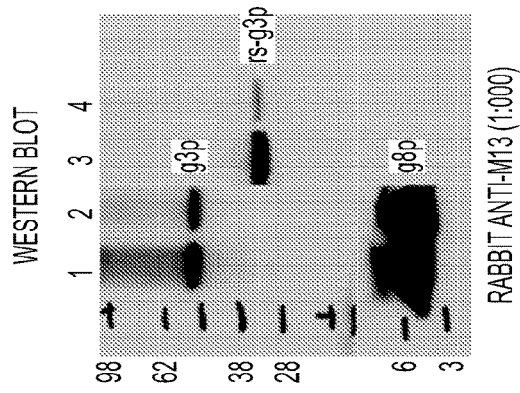
FIG. 12C shows the results of a gel filtration assay using Sephacryl S-300 and rs-g3p(N1N2).
Figure 12D:
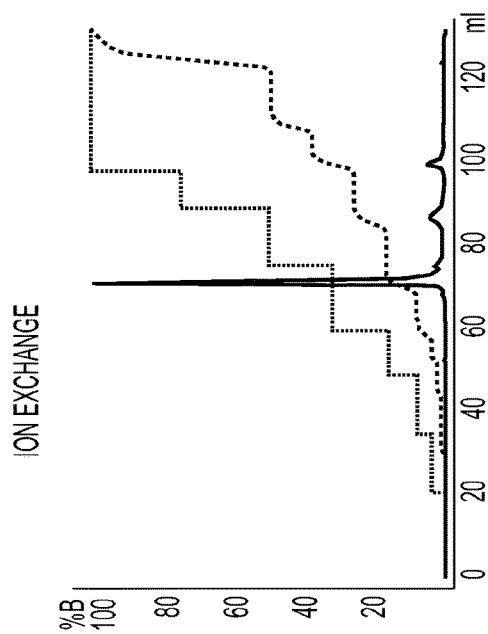
FIG. 12D shows a Western Blot of rs-g3p(N1N2) together with g3p and g8p controls. M13 phage are run in lanes 1 and 2 as a positive control, and detected with a polyclonal anti-M13 antibody, which detects both g8p and g3p. Purified rs-g3p is run in lanes 3 and 4, and detected with the same polyclonal anti-M13 antibody.
Figure 12A:
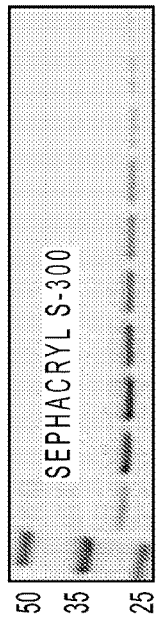
FIG. 12A shows a schematic of rs-g3p(N1N2) (Construct 3).
Figure 12B:
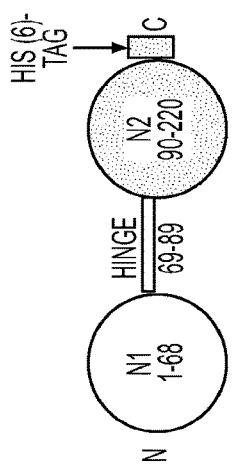
FIG. 12B presents an ion exchange profile for rs-g3p (N1N2).

Binding competition was assessed for phage fd, which has the same amino acid sequence as M13 g3p in the N1 and N2 domains (FIG. 2); IIHY, which has a higher hinge Tm than M13, and AAA. Phages fd, AAA, and IIHY were pre-activated at 50° C. for 1.5 hours, then activated and non-activated Fd, AAA, & IIHY were compared for their ability to compete with labeled M13. FIG. 11 presents the results. Wild type fd was a better competitor when activated by heating. In contrast, heating had little effect on IIHY, which has a higher hinge Tm. AAA, which has decreased N2 domain stability relative to M13, was a better competitor with or without heat pretreatment.

These data support the conclusion that the interaction of M13 with β-amyloid is via a mechanism similar to that by which M13 infects bacteria. First, they indicate that hydrophobic interactions are important for the M13-β-amyloid interaction. Second, the temperature dependence of M13 binding and disaggregation activities reflect the N1-N2 hinge unfolding Tm. Third, selective proteolysis of g3p abrogates M13-β-amyloid interactions.

Figure 13:
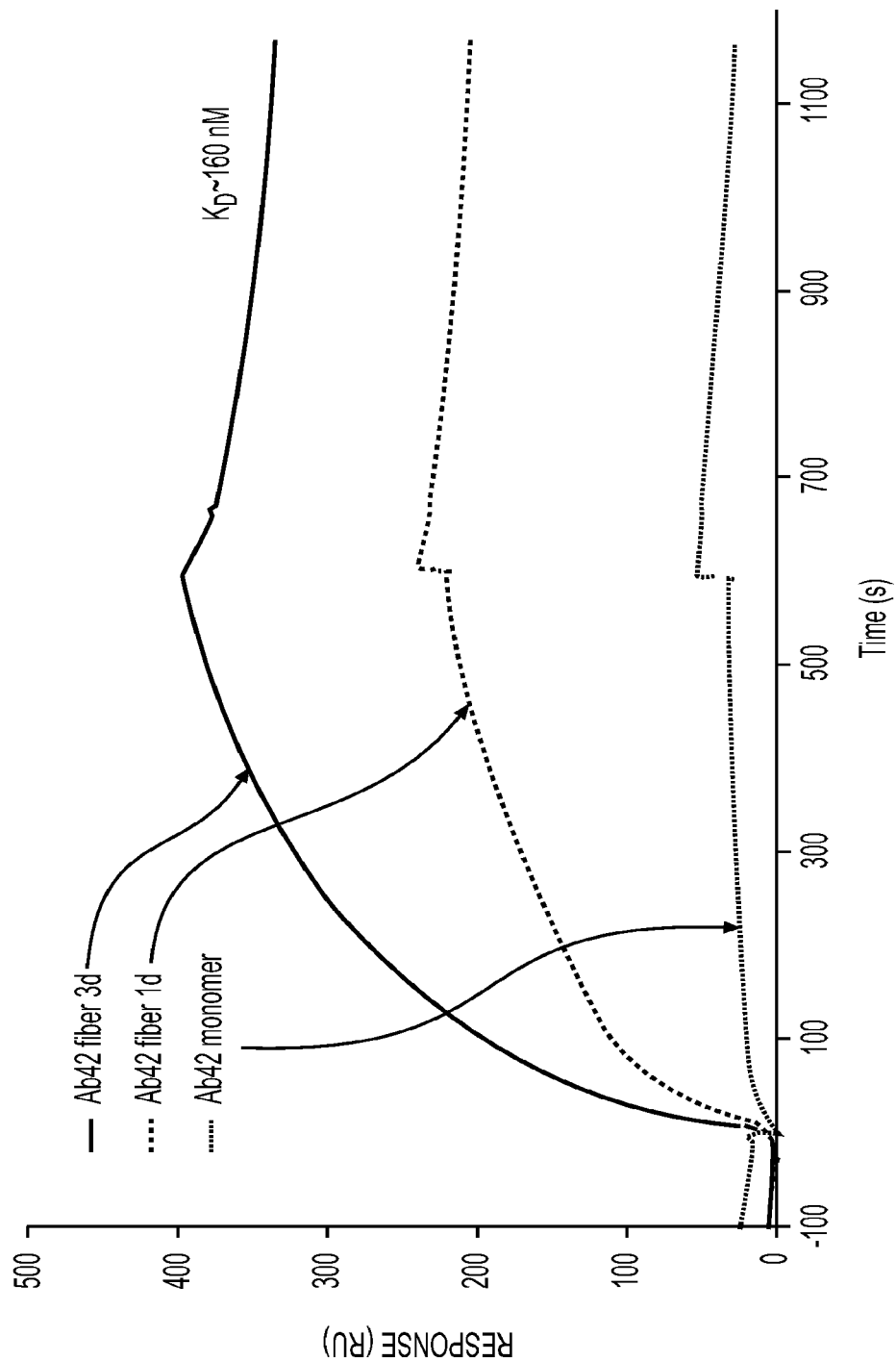
FIG. 13 presents SPR data using rs-g3p(N1N2) (Construct 3). rs-g3p(N1N2) potently binds fAβ42 with a $K_D$ of about 160 nM, but does not bind monomers.

Example 7: A g3p Fragment Selectively & Potently Binds Amyloid, but not Monomers To assess whether a g3p fragment retains the ability to bind to amyloid, a g3p fragment comprising N1 and N2 was prepared and assessed for its ability to bind Aβ fibrils versus Aβ monomers by surface plasmon resonance (SPR). The results indicate that rs-g3p(N1N2) preferentially binds Aβ fibrils; it does not bind Aβ monomers. Surface plasmon resonance studies using 4 μM rs-g3p(N1N2) are reported in FIG. 13, which also shows the $K_D$ of rs-g3p(N1N2) binding to be about 160 nM. This high affinity interaction indicates that a specific binding process is occurring between rs-g3p(N1N2) and the amyloid fiber.

Additional constructs were assessed by SPR. The table below summarizes the results.

| Analytes | ka (1/M · s) | kd (1/s) | $K_D$ |
|---|---|---|---|
| Construct 1 M13 | 2.6e3 | 9.2e−6 | 3.59 nM |
| Construct 3 rs-G3P(N1N2), 25° C. | 1.5e3 | 2.4e−4 | 0.15 uM |
| Construct 3 rs-G3P(N1N2), preheated at 37° C. | 4.1e3 | 2e−4 | 0.05 uM |
| Construct 4 rs-g3p (N1N2)-hIgG4Fc fusion protein, 25° C. | 1.75e4 | 1.28e−4 | 7.32 nM |
| Construct 5 rs-g3p (N1N2)-hIgG4Fc fusion protein, 25° C. | 1.52e4 | 1.66e−4 | 10.9 nM |
| Construct 6 N1N2-IgG1Fc fusion protein, 25° C. | 1.71e4 | 1.58e−4 | 9.2 nM |

Example 8: A g3p Fragment Potently Disaggregates Aβ42 Fibers

Figures 14A, 14B:
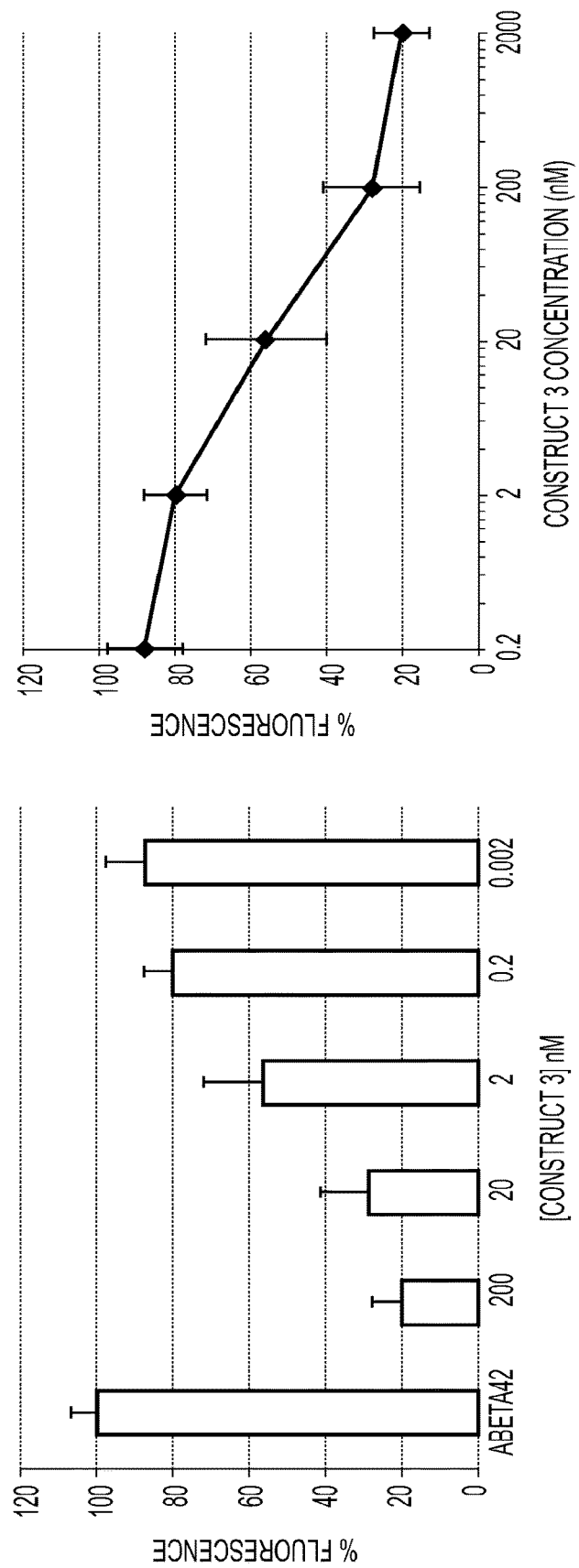
FIG. 14A and FIG. 14B present a ThT fluorescence assay used to measure the amyloid present in a given sample. 10 μM of Aβ42 monomers was incubated in the presence or absence of 5 concentrations of rs-g3p(N1N2) (Construct 3) at 37° C. for 3 days. The amount of fibers formed at the end of 3 days as measured by quantitating the bound ThT fluorescence. The $IC_{50}$ is approximately 20 nM indicating that rs-g3p(N1N2) potently inhibits formation of Aβ42 fibers (FIG. 14B).

To test whether a g3p fragment can disaggregate amyloid fibers, rs-g3p(N1N2) was tested in a ThT fluorescence assay for its ability to degrade preformed fAβ42 fibrils. The results indicate that rs-g3p(N1N2) potently disaggregates fAβ42. FIG. 14A shows the results of this experiment, that rs-g3p (N1N2) disaggregates fAβ42 in a dose dependent fashion. FIG. 14B shows the $10_{50}$ to be approximately 20 nM.

Figure 15A:
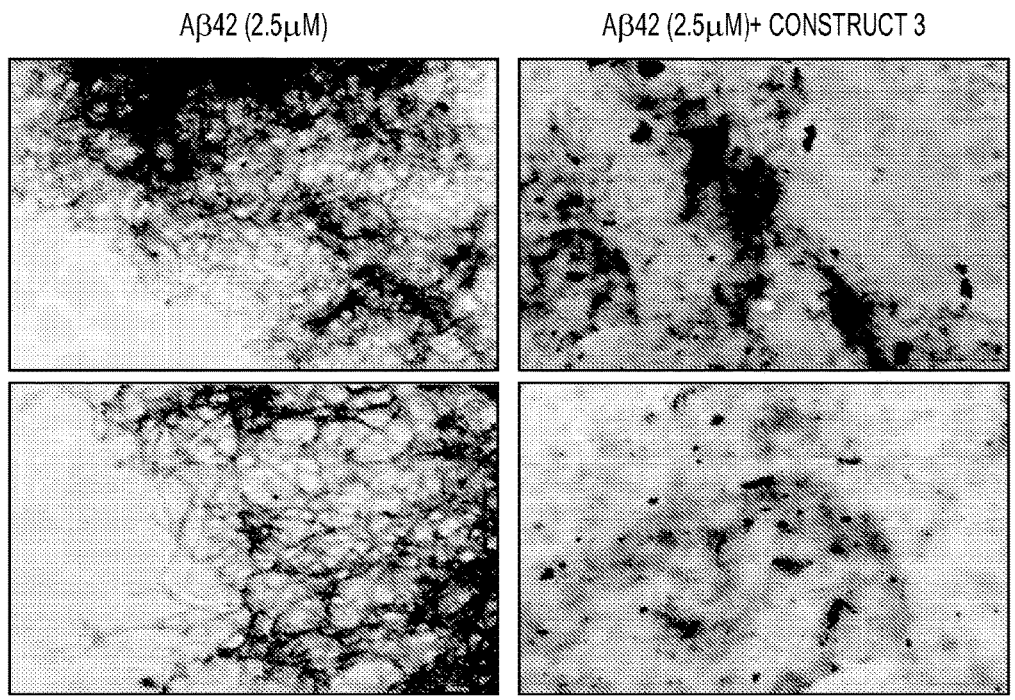
FIG. 15A shows the transmission electron micrography (TEM) results of incubating fAβ42 in the presence or absence of rs-g3p(N1N2) (Construct 3).
Figure 15B:
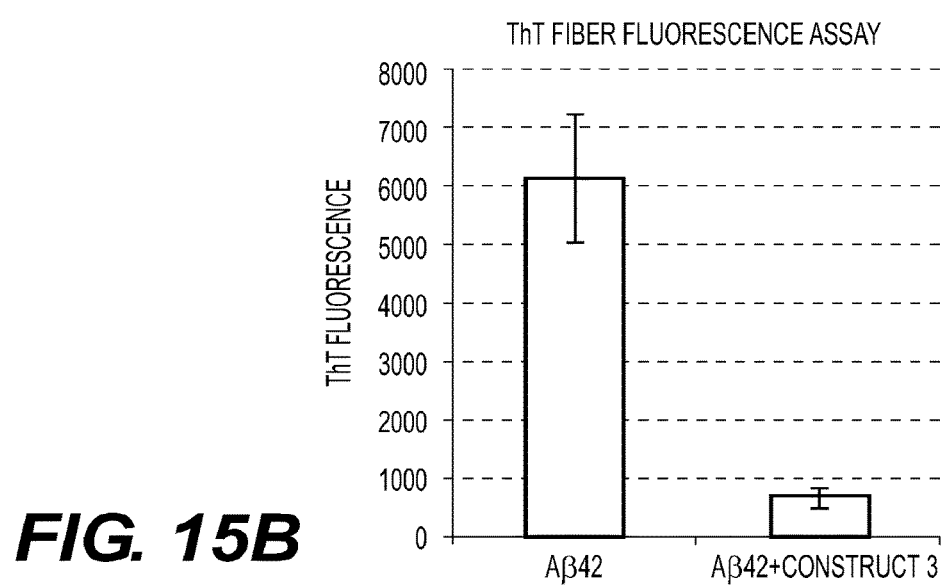
FIG. 15B shows the results of a ThT fluorescence assay using Aβ42 and 2 μM rs-g3p(N1N2) (Construct 3) incubated at 37° C. for 7 days. rs-g3p(N1N2) blocks the formation of fAβ42.

In a separate experiment, Aβ42 was incubated with or without rs-g3p(N1N2) at a concentration of 2 μM for seven days at 37° C. and the integrity of the Aβ42 fibers was assessed by transmission electron micrograpy. FIG. 15A shows the results of this experiment, that rs-g3p(N1N2) disaggregates Aβ42 fibers. FIG. 15B reports the results of a ThT assay on these same samples. Rs-g3p(N1N2) degraded preformed Aβ42 fibers in this ThT assay.

Example 9: rs-g3p(N1N2) Blocks α-Synuclein and Aβ Assembly and rs-g3p(N1N2)-hIgG1-Fc Blocks Assembly and Inhibits Aggregation of Aβ

Figure 16:
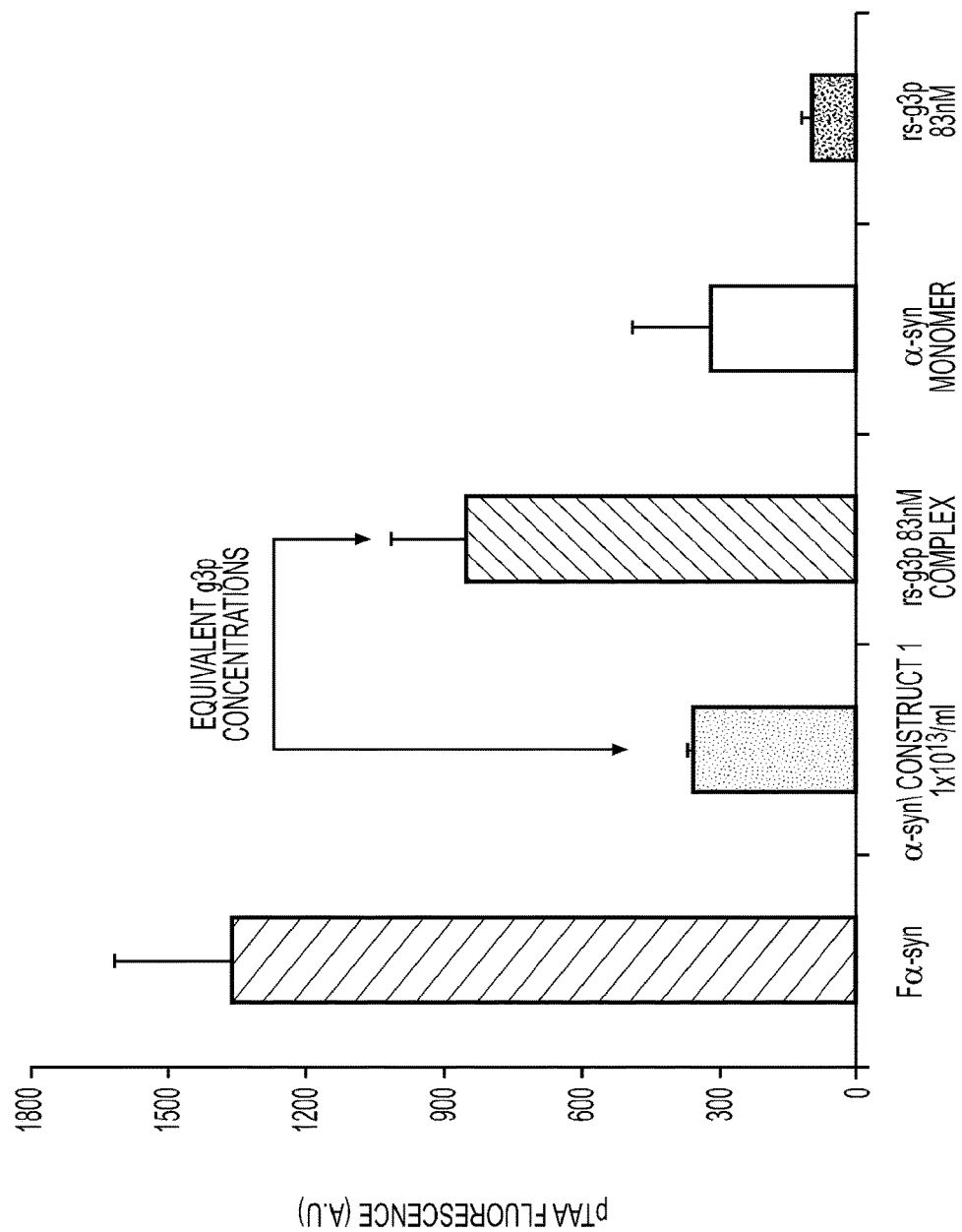
FIG. 16 demonstrates that rs-g3p(N1N2) (Construct 3) potently inhibits the formation of α-synuclein fibers. 25 μM of α-synuclein was assembled by agitating at 300 rpm for 4 days at 37° C. (see, Bar 1). The second bar on the graph represents alpha-synuclein monomers plus $1 \times 10^{-13}$ pentameric M13 phage shaking at 37° C. for 3 days. The results shown in bar 2 indicate that pentameric M13 blocks assembly of α-synuclein fibers. The third bar on the graph represents alpha-synuclein monomers +83 nM rsg3p monomers. The results shown in bar 3 indicate that monomers are less effective at inhibiting α-synuclein fiber formation than pentameric M13. Bar 4 is a negative control showing alpha synuclein monomers at time zero. In bar 5, g3p monomers without α-synuclein fibers is shown to determine whether g3p binds to pTAA and sequesters the dye from binding to the fibers. The results shown in bar 5 indicate that g3p does not bind to pTAA.

To determine whether g3p can block α-synuclein fiber assembly, and also to determine whether the valency (i.e., the number of copies of g3p) plays a role, an assay testing the ability of pentameric g3p (5 copies of g3p) and monomeric g3p (one copy of g3p) to block α-synuclein activity was conducted. The results show that g3p blocks α-synuclein fiber assembly, and that pentameric g3p is more efficient than monomeric g3p at this activity. See FIG. 16.

Figure 30A:
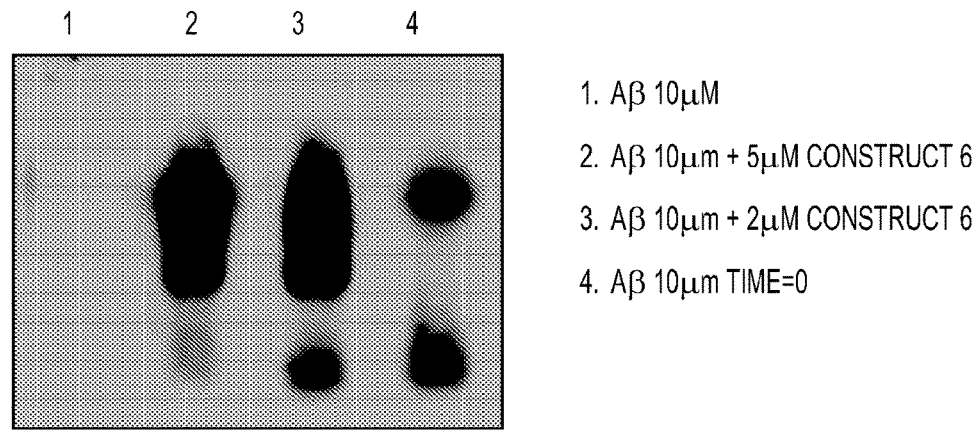
FIG. 30A and FIG. 30B show assembly inhibition of Aβ42 with rs-g3p(N1N2)-hIgG1-Fc (Construct 6).
Figure 30B:
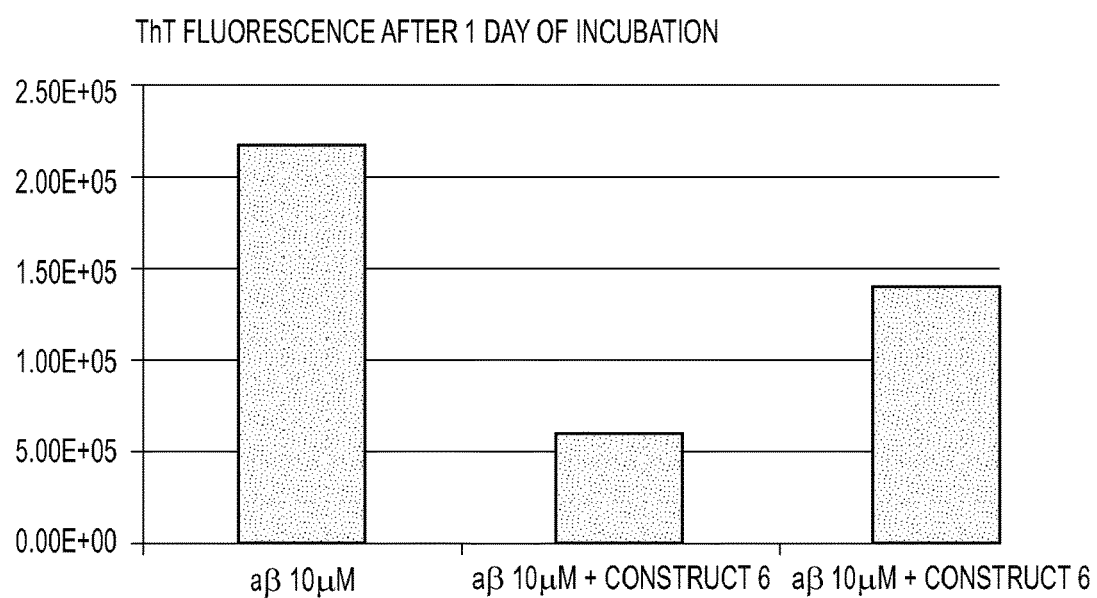
Figure 31A:
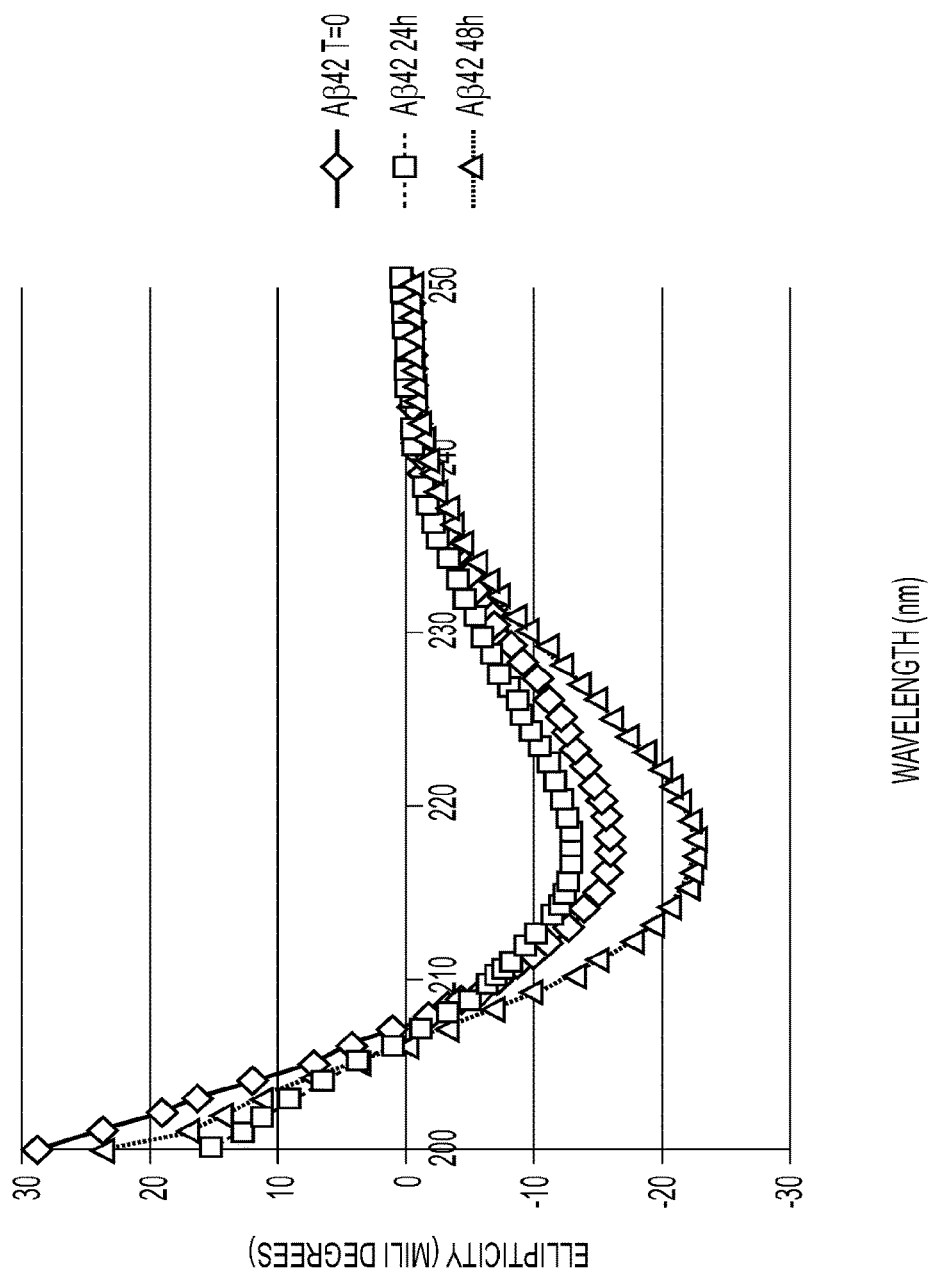
FIG. 31A, FIG. 31B, FIG. 31C, and FIG. 31D present representative circular dichroism data showing that Aβ42 assembly is inhibited by rs-g3p(N1N2) (Construct 3). Circular dichroism measures the α-helix and β-sheet content of the Aβ fibers to be assessed.
Figure 31B:
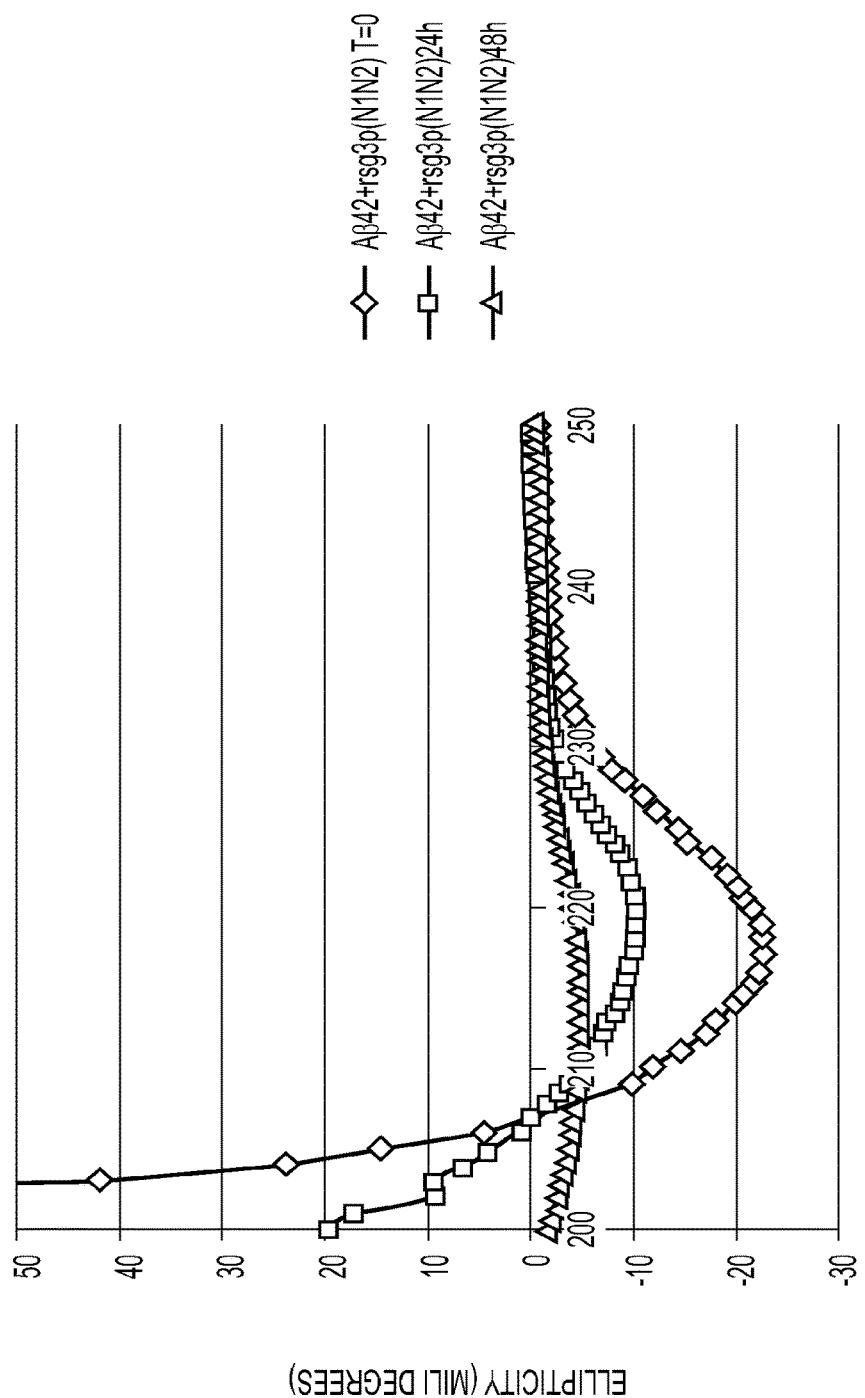
Figure 31C:
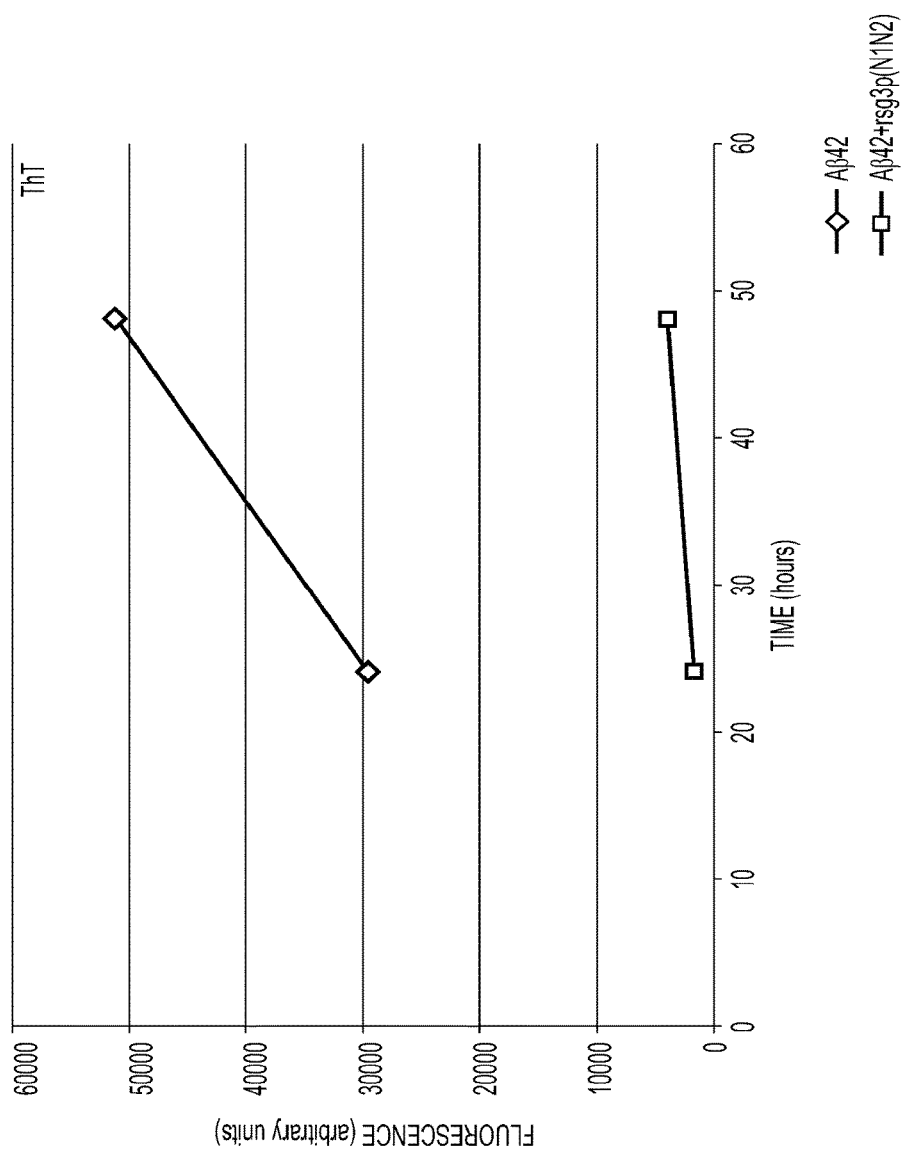
Figure 31D:
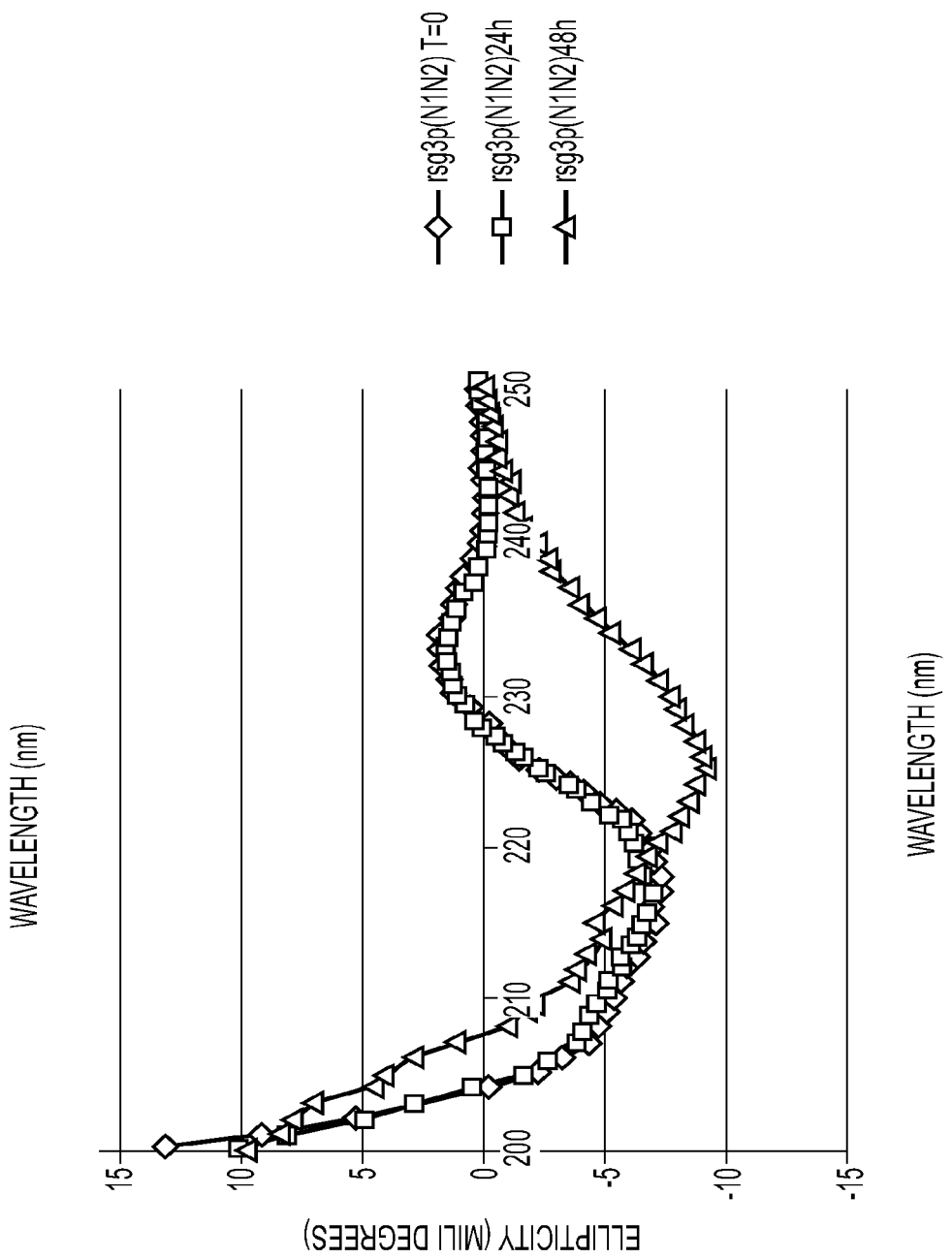

The ability of rs-g3p(N1N2) (Construct 3) and rs-g3p (N1N2)-hIgG1-Fc (Construct 6) to inhibit assembly of Aβ42 was also assessed. As shown in FIG. 30 and FIG. 31, Construct 3 and Construct 6 are capable of inhibiting the assembly of fAβ42 in a dose-dependent fashion. As shown in FIG. 37, Construct 3 and Construct 6 are capable of inhibiting fAβ42 aggregation.

Example 10: rs-g3p(N1N2)-Ig Fusion Protein Binds to and Disaggregates Aβ

Figure 17:
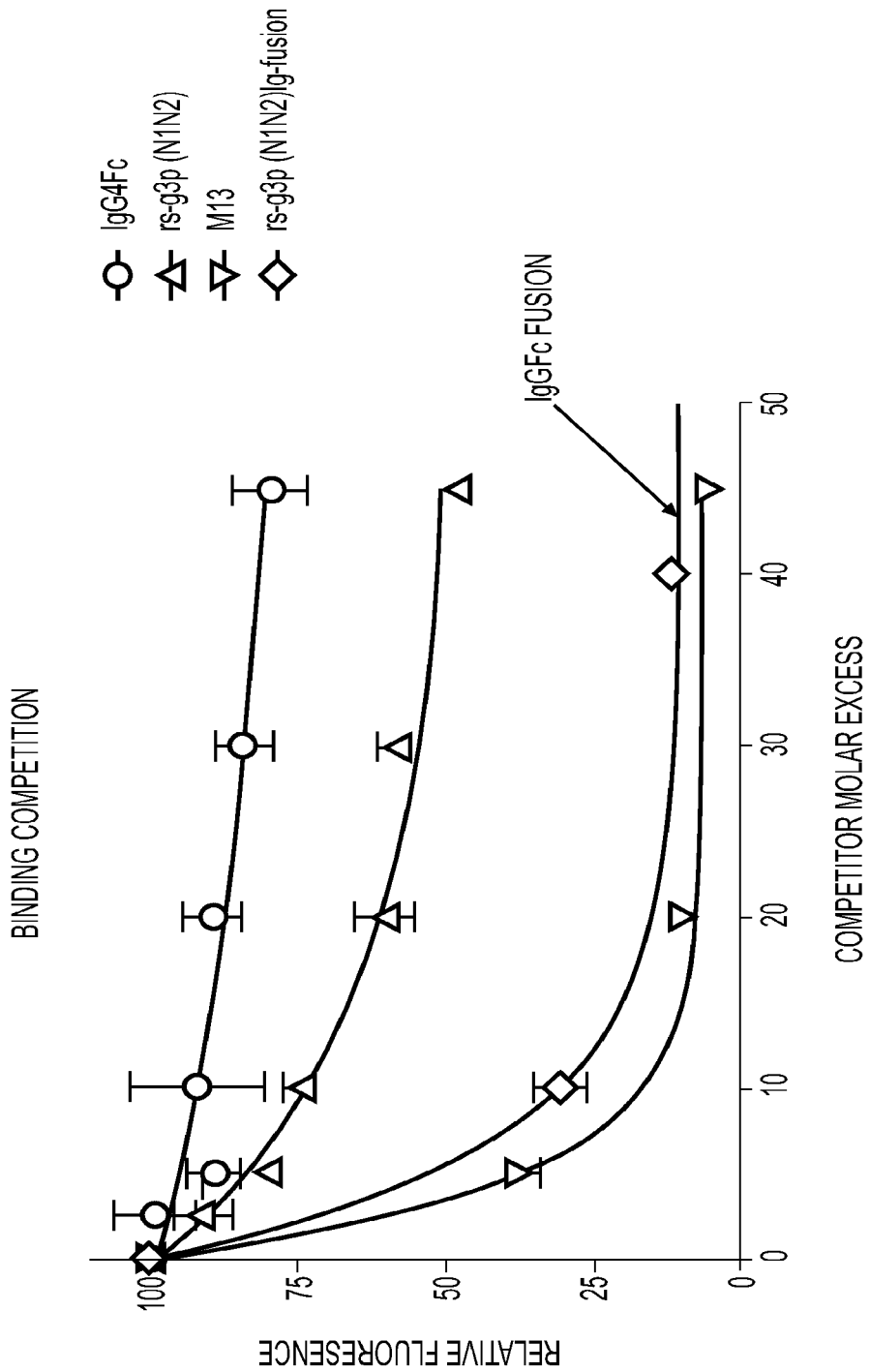
FIG. 17 presents competition binding data for rs-g3p (N1N2) (Construct 3), M13 (Construct 2), rs-g3p(N1N2)-hIgG4-Fc fusion protein (Construct 4), and an IgG4-Fc negative control.
Figure 18:
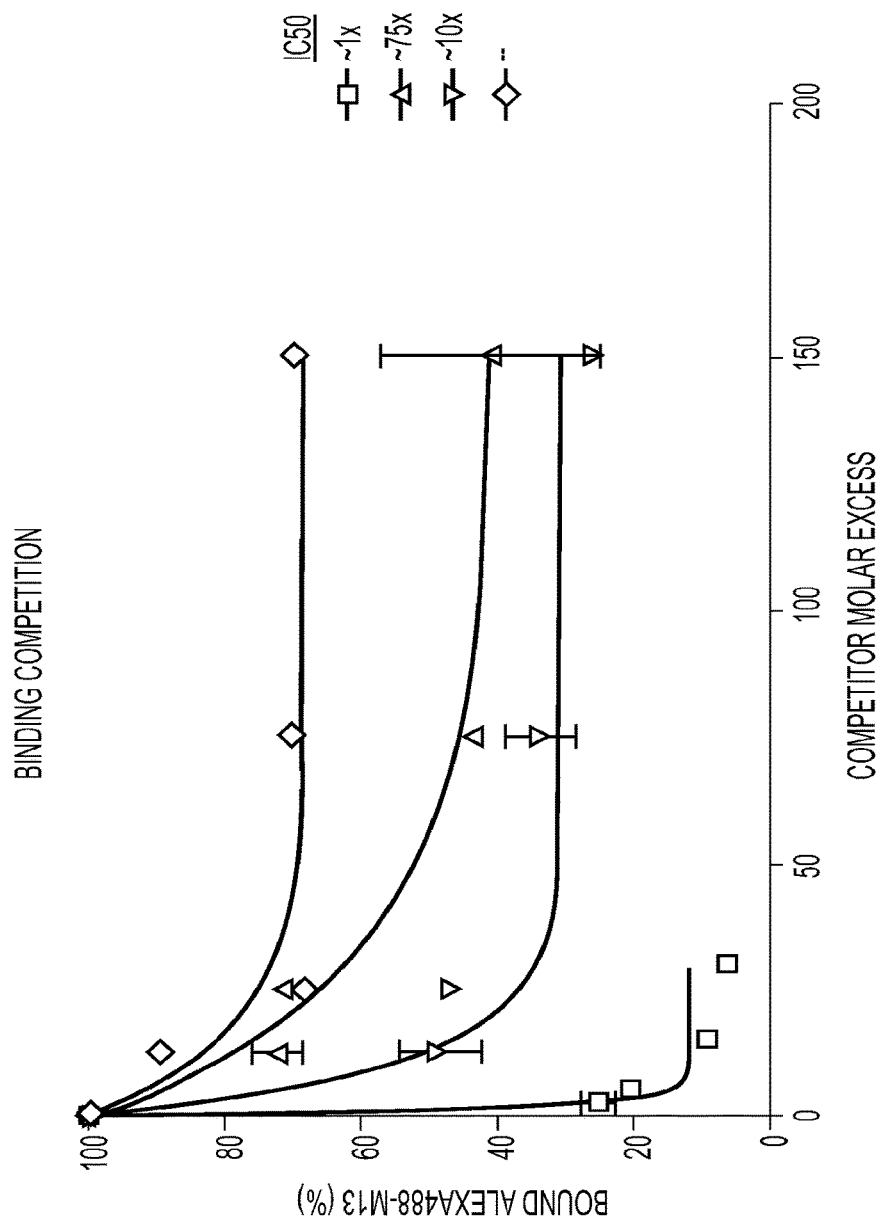
FIG. 18 presents competition binding data comparing M13 (Construct 2; squares), rs-g3p(N1N2) (Construct 3; triangles), rs-g3p(N1N2)-hIgG4-Fc fusion protein (Construct 4; upside down triangles), and a recombinant IgG4-Fc negative control (diamonds).

To assess whether g3p valency plays a role in the potency of g3p binding to amyloid, an Ig fusion protein that is bivalent for rs-g3p(N1N2) ("rs-g3p(N1N2)-Ig fusion") was made and compared with pentavalent M13 for its ability to bind to Aβ fibers. As shown in FIG. 17, rs-g3p(N1N2)-Ig fusion binds to Aβ with similar affinity as M13, and more potently than rs-g3p(N1N2) alone, indicating that the valency of g3p may be important. Similar results were obtained in a repeat of the competition assay. FIG. 18. In FIG. 18, the squares represent Construct 2 (M13); the triangles represent Construct 3 (rs-g3p(N1N2)); the upside down triangles represent Construct 4 (rs-g3p(N1N2)-Ig fusion); and the diamonds represent a r-IgG4 Fc negative control.

Figure 19:
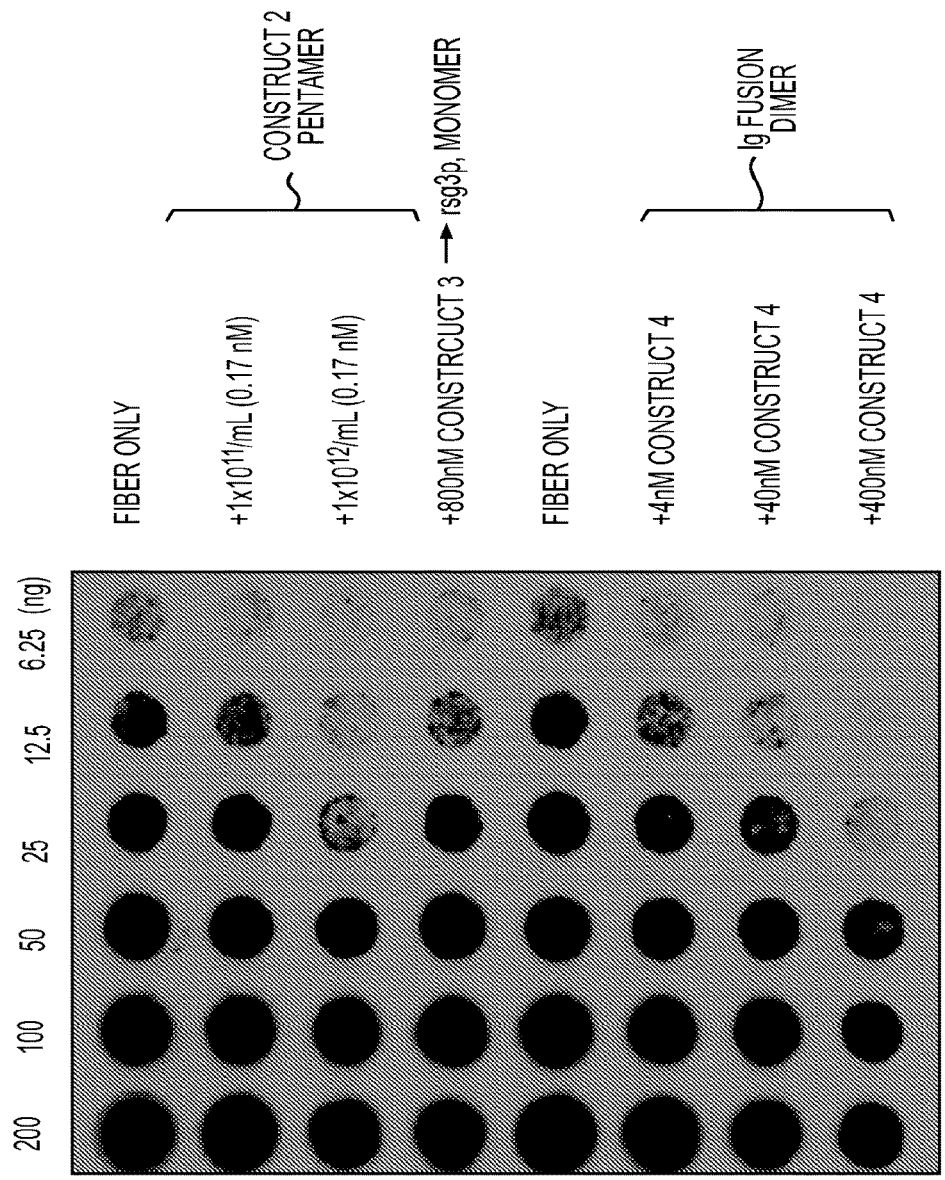
FIG. 19 shows a filter trap assay comparing five concentrations of A342 fibers plus or minus two concentrations of M13 (Construct 2), 800 nM rs-g3p(N1N2) (Construct 3), and three concentrations of rs-g3p(N1N2)-hIgG4-Fc fusion protein (Construct 4).

To assess whether or not valency also plays a role in disaggregation, bivalent rs-g3p(N1N2)-Ig fusion ("Construct 4") was compared to pentavalent M13 in a filter trap assay. FIG. 19. The results indicate that both bivalent rs-g3p(N1N2)-Ig fusion and pentavalent M13 potently disaggregate β-amyloid fibers. Also indicated is that valency may be important for potency of disaggregation, as indicated by the ability of 1.7 nM pentavalent M13 to reduce aggregates at a level similar to 40 nM rs-g3p(N1N2)-Ig fusion. FIG. 19.

In a similar assay, 1×10$^{12}$/ml M13 (Construct 2); 80 nm and 800 nM rs-g3p(N1N2)-hIgG4-Fc (Construct 5); and 80 nm and 800 nM of rs-g3p(N1N2)-hIgG1-Fc (Construct 6) were assayed for their ability to disaggregate Aβ42 fibers in a filter trap assay. Constructs 2, 5, and 6 potently disaggregate β-amyloid fibers. FIG. 33.

Example 11: Tetrameric Streptavidin-[Biotin-g3p(N1N2)] Protein Binds to and Disaggregates fAβ

Figure 20:
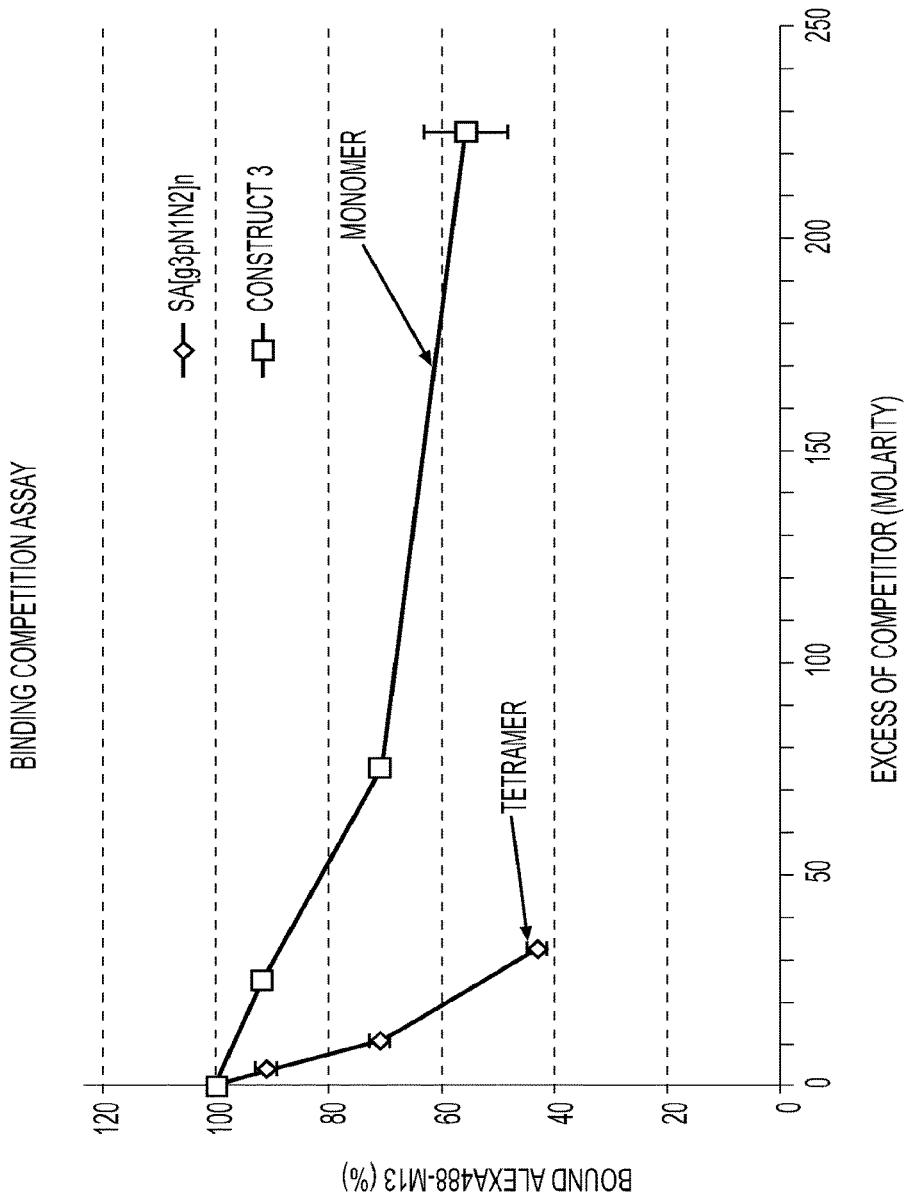
FIG. 20 presents competition binding data for rs-g3p (N1N2) (Construct 3; "monomer") and streptavidin conjugated rs-g3p(N1N2) ("SA[g3pN1N2]$_{n=2-4}$", "SA-g3p"; "tetramer"). rs-g3p(N1N2) and SA-g3p were compared for their ability to compete with labeled M13 for binding to Aβ during a three hour incubation at 37° C.

To further assess the role of valency on g3p's ability to bind and disaggregate amyloid, a tetrameric streptavidin conjugated g3p(N1N2) was prepared by combining rs-g3p (N1N2) with Biotin-Lys-NTA in the presence of $NiSO_4$. Excess ligand was removed using a MWCO 3 KDa membrane. Streptavidin was added, and excess rs-g3p(N1N2)-Biotin was removed using a MWCO 100 KDa membrane. The resulting g3p construct, streptavidin-[biotin-g3p (N1N2)], has four rs-g3p(N1N2) moieties. Streptavidin-[biotin-g3p(N1N2)] was compared to rs-g3p(N1N2) ("Construct 3") in a binding assay. FIG. 20. Tetrameric streptavidin-[biotin-g3p(N1N2)] bound to fAβ more potently than monomeric rs-g3p(N1N2), providing a further indication that valency is important for potency of binding. FIG. 20. However, even monomeric rs-g3p(N1N2) bound to fAβ in therapeutically acceptable levels.

Figure 21:
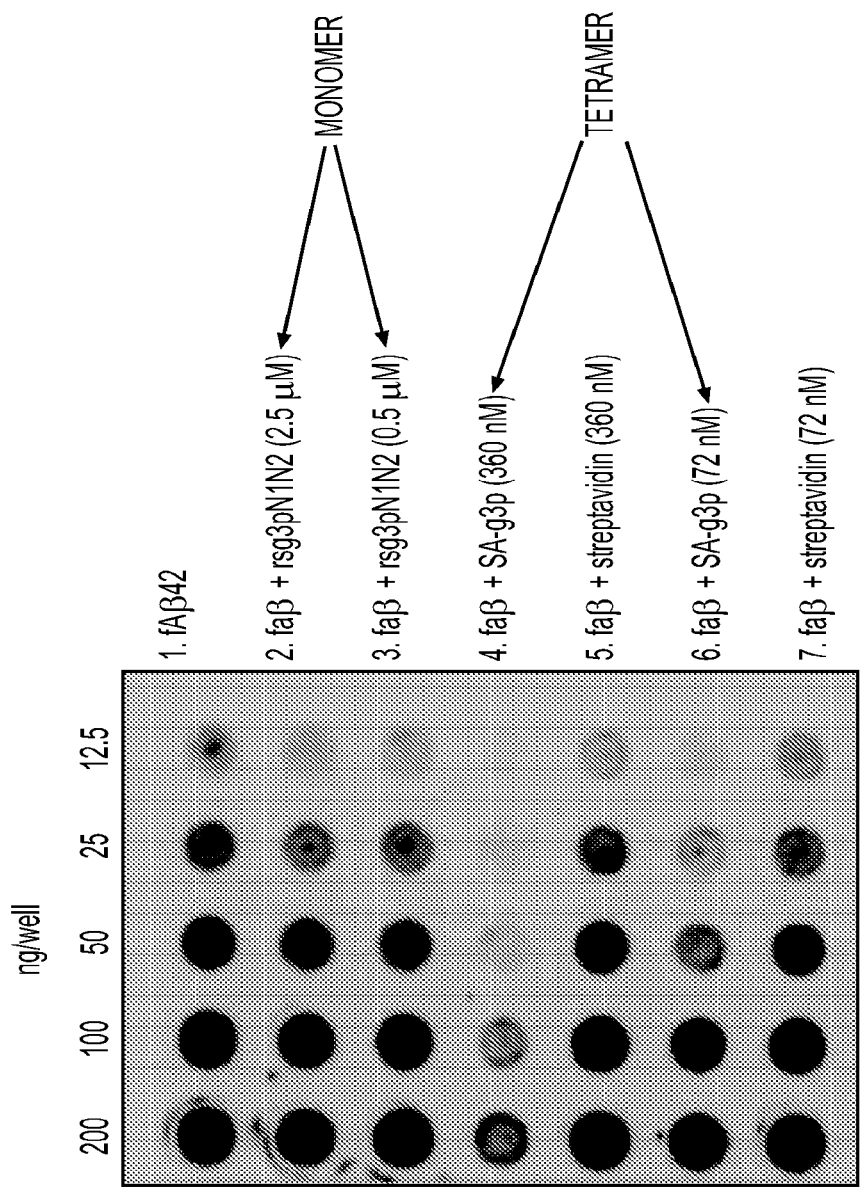
FIG. 21 shows a filter trap assay comparing five concentrations of fAβ42 plus or minus two concentrations of rs-g3p(N1N2) (Construct 3; "monomer") and two concentrations of SA-g3p ("tetramer").

To assess whether or not valency also plays a role in disaggregation, monomeric rs-g3p(N1N2) was compared to tetrameric streptavidin-[biotin-g3p(N1N2)] in a filter trap assay. FIG. 21. The results indicate that both monomeric rs-g3p(N1N2) and tetrameric streptavidin-[biotin-g3p (N1N2)] potently disaggregate fAβ fibers. Also indicated is that valency may be important for potency of disaggregation, as indicated by the superior ability of 360 nM tetrameric streptavidin-[biotin-g3p(N1N2)] to abrogate up to 200 ng fAβ aggregates, as compared to the reduced disaggregation of Aβ by 2.5 μM monomeric rs-g3p(N1N2). FIG. 21, row 2 compared to row 4, for example.

Figure 22B:
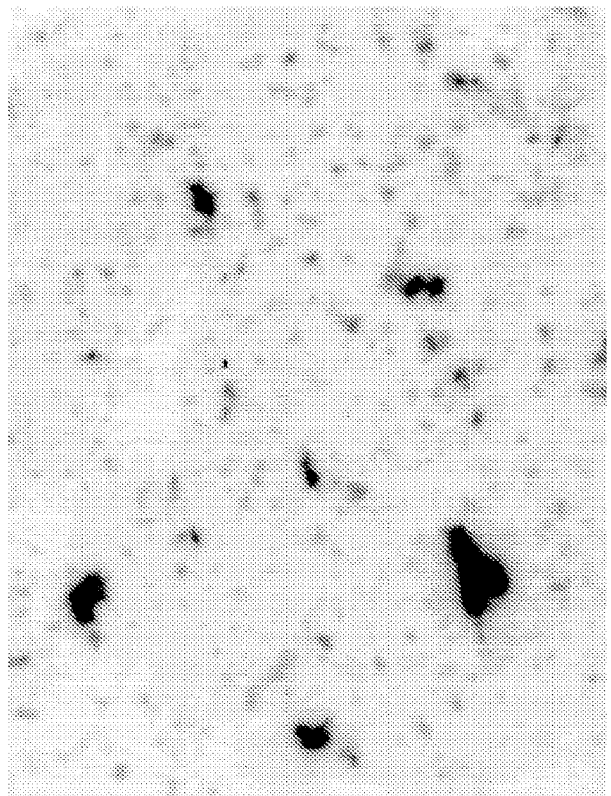
FIGS. 22A and 22B show TEMs of fAβ42 at times zero (FIG. 22A) and three days after incubation with SA-g3p (FIG. 22B).
Figure 22A:
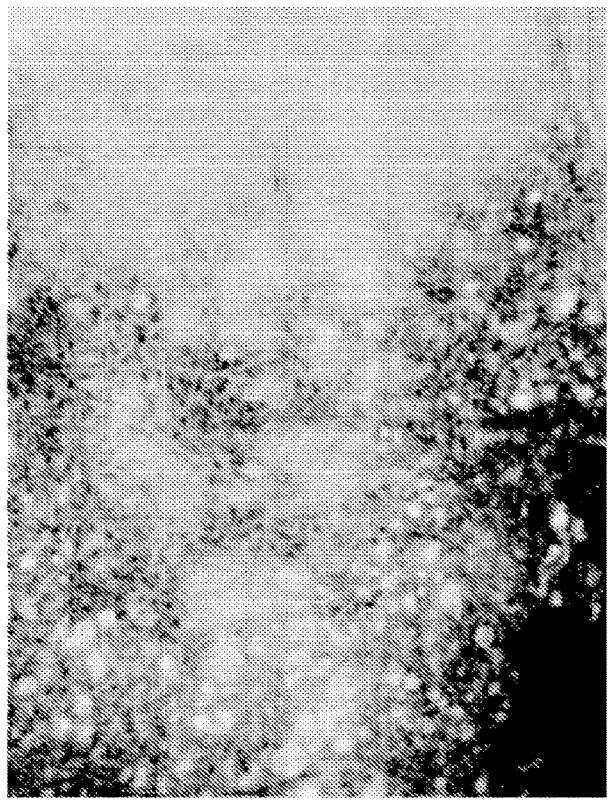

Disaggregation of Aβ by streptavidin-[biotin-g3p(N1N2)] was also assessed by TEM. Streptavidin-[biotin-g3p (N1N2)] completely disaggregated fAβ42 after a three day incubation. FIG. 22.

Figure 28:
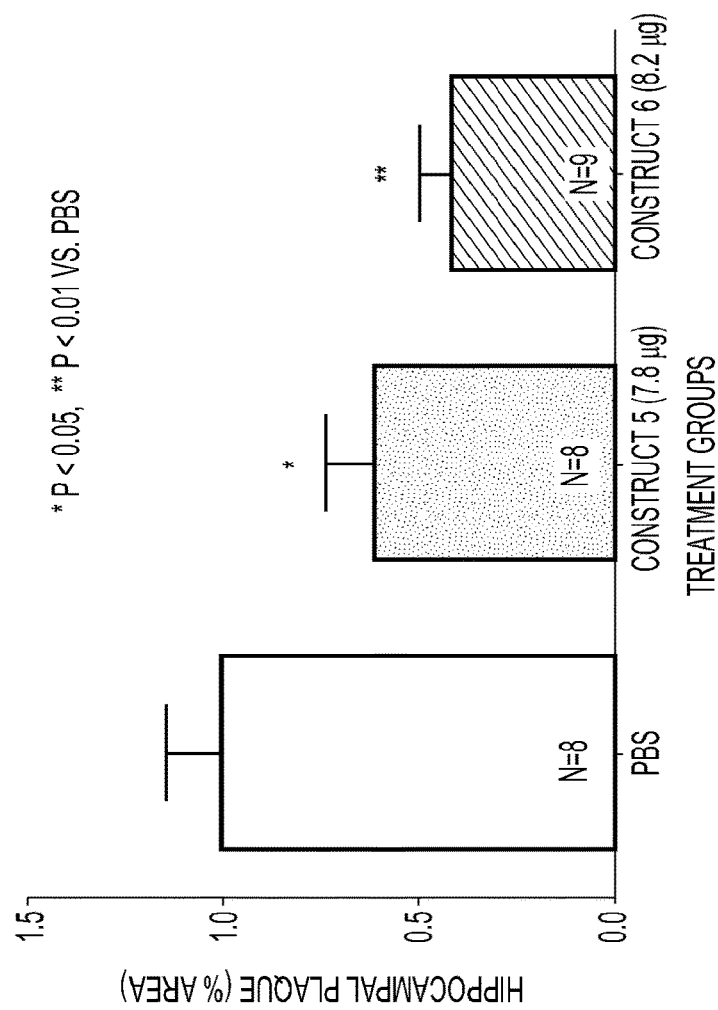
FIG. 28 shows the results of an experiment testing two rs-g3p(N1N2)-IgG fusion proteins for their ability to reduce amyloid β in a transgenic mouse model of Alzheimer's Disease. rs-g3p(N1N2)-hIgG4-Fc (Construct 5) and rs-g3p (N1N2)-hIgG1-Fc (Construct 6) both significantly reduced the level of amyloid β in the hippocampus of Alzheimer's Diseased mice.
Figure 29:
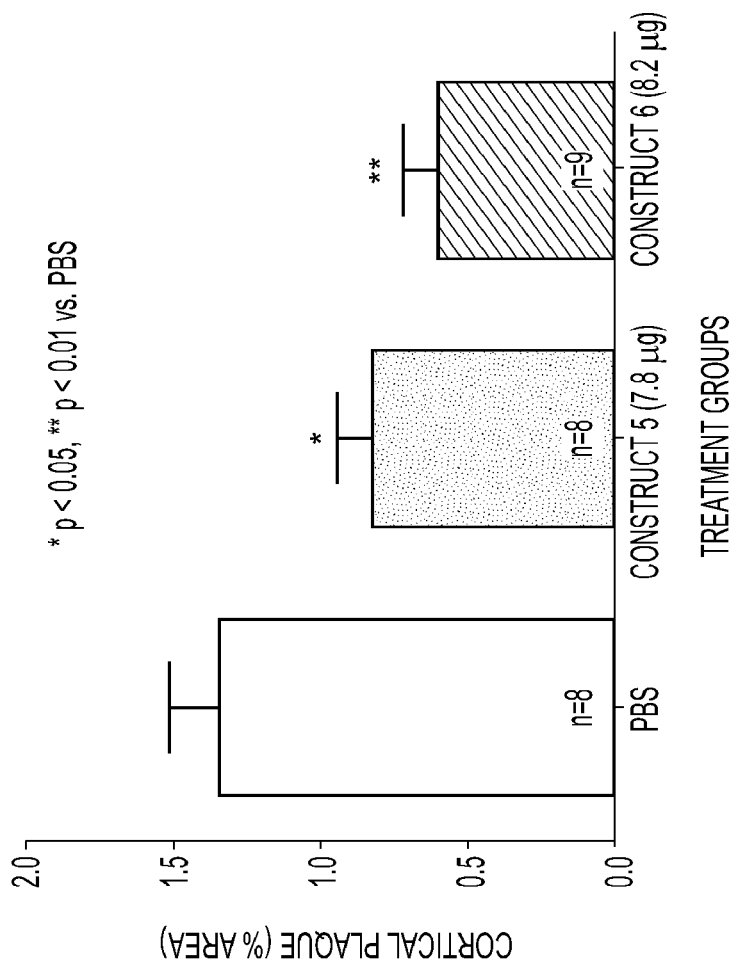
FIG. 29 shows the results of an experiment testing two rs-g3p(N1N2)-IgG fusion proteins for their ability to reduce amyloid β in a transgenic mouse model of Alzheimer's Disease. rs-g3p(N1N2)-hIgG4-Fc (Construct 5) and rs-g3p (N1N2)-hIgG1-Fc (Construct 6) were both able to significantly reduce the level of amyloid β in the cerebral cortex of Alzheimer's Disease mice.

Example 12: N1N2-Ig Fusion Protein Significantly Reduces Aβ in a Murine Model of Alzheimers Disease Using a well known mouse model for studying Alzheimer's Disease (Hsiao et al., Science (1996) 274:99-102; Duyckaerts et al., Acta Neuropathol (2008) 115:5-38), male Tg2576 mice were aged to greater than 500 days, injected (2 μL/injection) bilaterally into the hippocampus with two different preparations of N1N2-Ig fusions (Construct 5 at 7.8 μg/injection and Construct 6 at 8.2 μg/injection) or saline as a negative control, and sacrificed on day 7. Brain tissue was harvested, sectioned, and stained for plaque load quantification using an anti-amyloid beta monoclonal antibody (82E1; cat. # MBS490005-IJ10323 from MyBioSource). As shown in FIG. 28, both N1N2-Ig fusion proteins significantly reduced the plaque load measured in the hippocampus compared to saline-treated mice. As shown in FIG. 29, both N1N2-Ig fusion proteins significantly reduced the plaque load measured in the cerebral cortex compared to saline-treated mice.

Example 13: N1N2-Ig Fusion Protein Blocks Aβ Oligomer Induced Cytotoxicity

Figure 32:
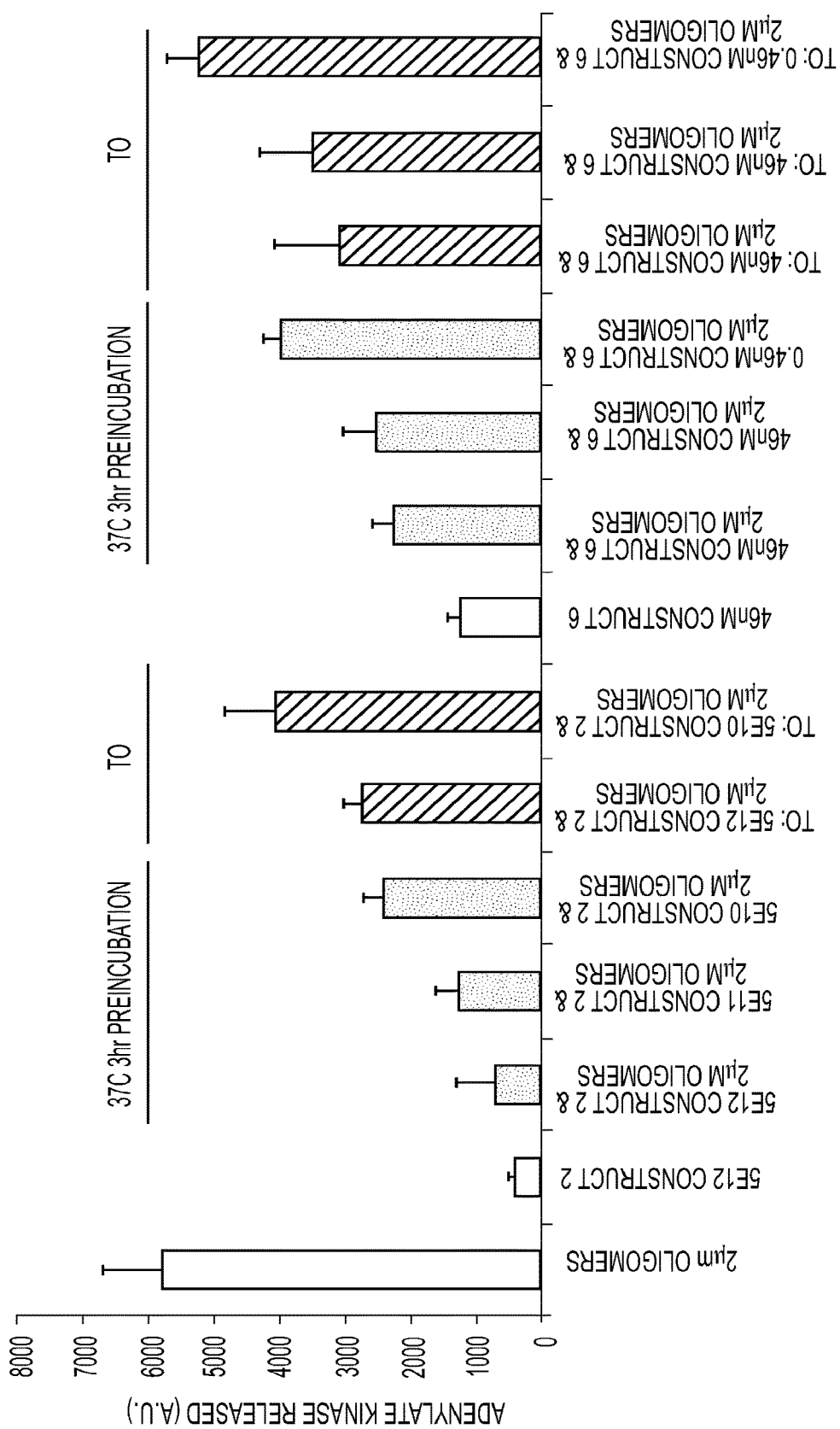
FIG. 32 presents representative data showing that M13 (Construct 2) and rs-g3p(N1N2)-hIgG1-Fc (Construct 6) block oligomer-induced toxicity of N2a cells. See, e.g., Stine et al. (2003) J. Biol. Chem. 278(13): 11612-11622 and Stine et al. (2011) Erik D. Roberson (ed.) Alzheimer's Disease and Frontotemporal Dementia, Methods in Molecular Biology, vol. 670: 13-32. N2a cells were differentiated by serum starvation for 48 hours prior to treatment. Aβ42 oligomers (2 uM) were pre-incubated with Construct 2 and Construct 6 at 37° C. for 3 hrs before addition to N2a cells. Time zero ("T0") complexes were not pre-incubated. After 24 hours of incubation, adenylate kinase ("AK") release was monitored. AK release into the medium indicates cell death/lysis. Aβ42 oligomers were made as described by Stine et. al., 2011. The results indicate that M13 and rs-g3p(N1N2)-hIgG1-Fc are potent inhibitors of toxic oligomers.
Figure 34A:
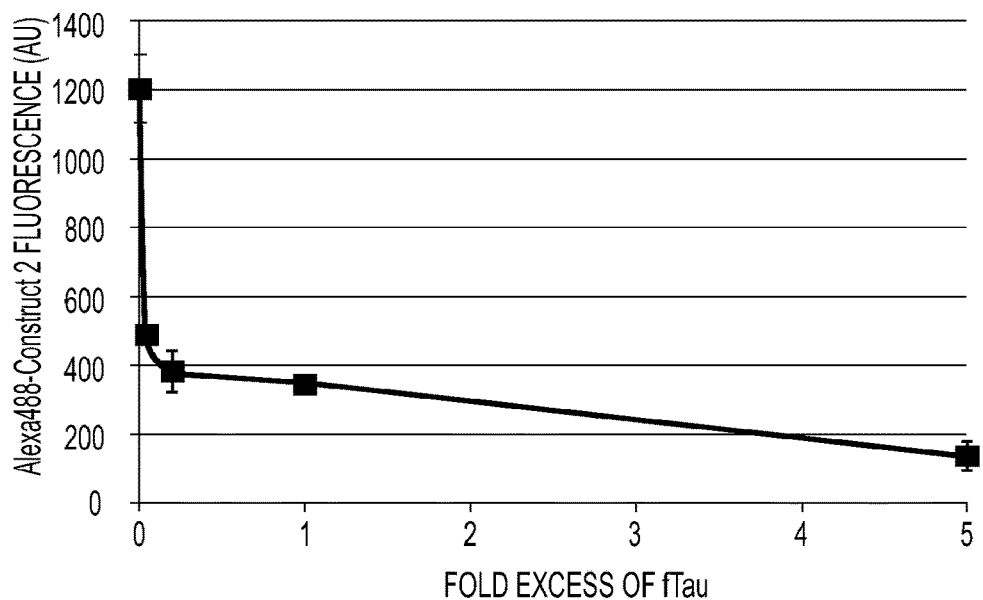
FIGS. 34A and 34B present representative assays used to measure the amount of M13 (Construct 2) bound to fAβ42 after 3 hours of preincubation with ftau. 5 µM of Aβ42 monomers bound to Construct 2 was incubated in the presence or absence of 4 concentrations of ftau at 37° C. for 3 hours. Since fAbeta:M13-Alexa488 pellets but ftau:M13-Alexa488 does not pellet, measuring the loss of fluorescence from the pelleted material indicates that ftau competed the fAbeta binding. Here, the amount of M13-fAβ42 formed at the end of 3 hours was measured by quantitating the Alexa488 fluorescence in the pelleted binding competition reaction. The results indicate that ftau is able to compete with M13-Alexa488 (Construct 2) for fAβ42 binding.
Figure 34B:
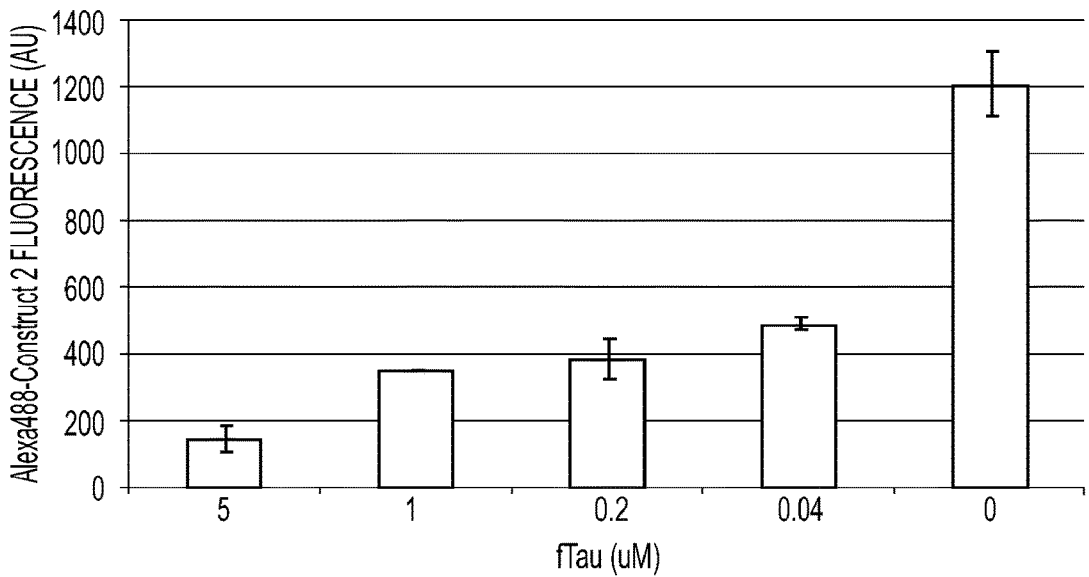

Aβ oligomers cause the release of certain toxic enzymes in neuronal cells. The enzyme can be assayed to determine whether a compound can inhibit the Aβ oligomer induced cytotoxicity. FIG. 32 presents representative data showing that M13 (Construct 2) and rs-g3p(N1N2)-hIgG1-Fc (Construct 6) block oligomer-induced toxicity to N2a cells. g3p fragments are therefore potent inhibitors of Aβ oligomer induced cytotoxicity.

Example 14: N1N2-Ig Fusion Protein Binds and Disaggregates Tau

Figure 35:
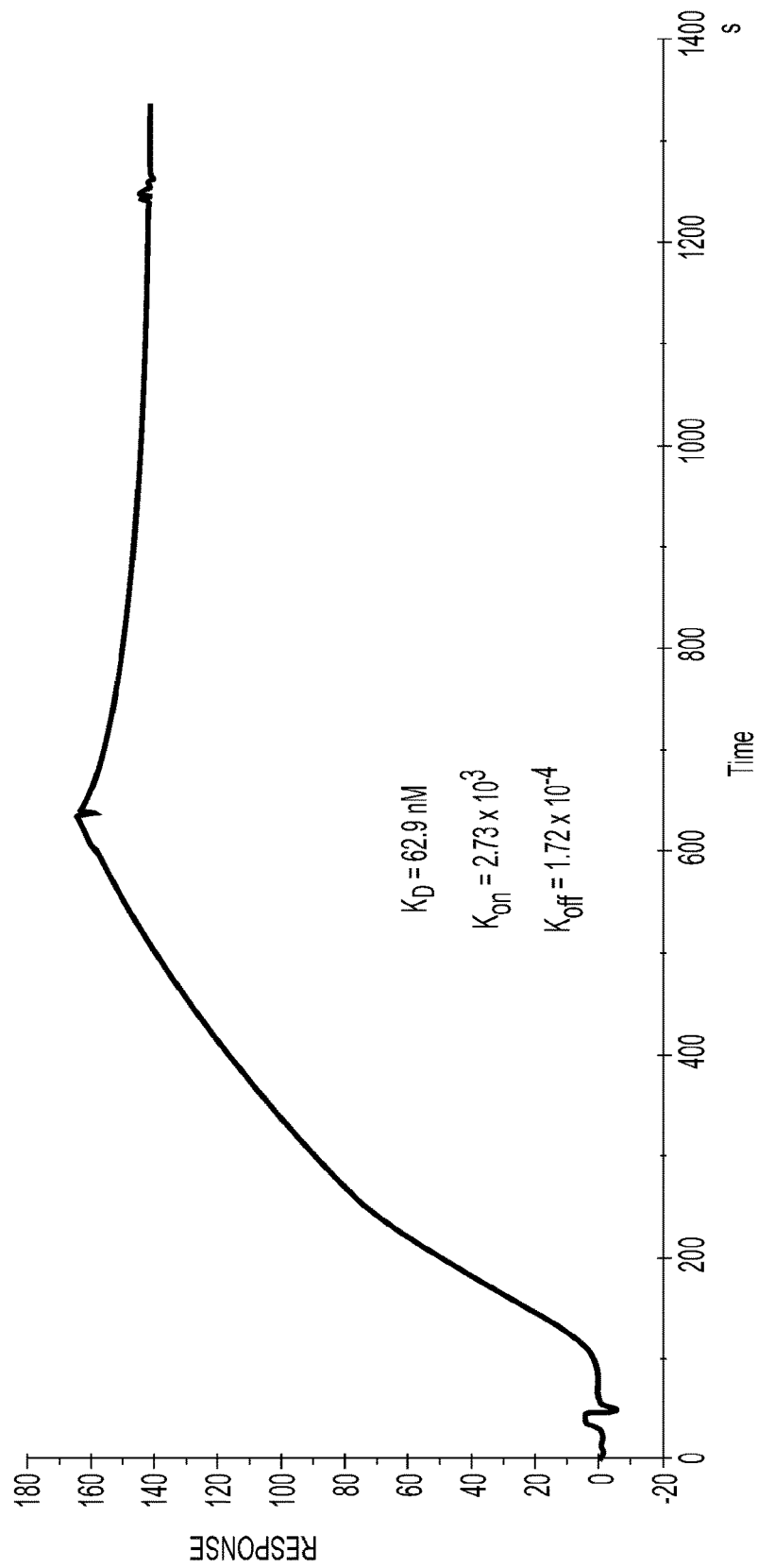
FIG. 35 shows the results of one representative SPR assay testing the ability of rs-g3p(N1N2)-hIgG4-Fc (Construct 4) to bind to ftau. The results indicate that Construct 4 potently binds ftau.

To assess whether a g3p fragment binds to tau, a g3p fragment-Ig fusion protein comprising N1 and N2 was prepared and assessed for its ability to bind ftau by surface plasmon resonance (SPR). FIG. 35 shows the results of one representative SPR assay showing that rs-g3p(N1N2)-hIgG4-Fc (Construct 4) potently binds ftau.

Figure 36A:
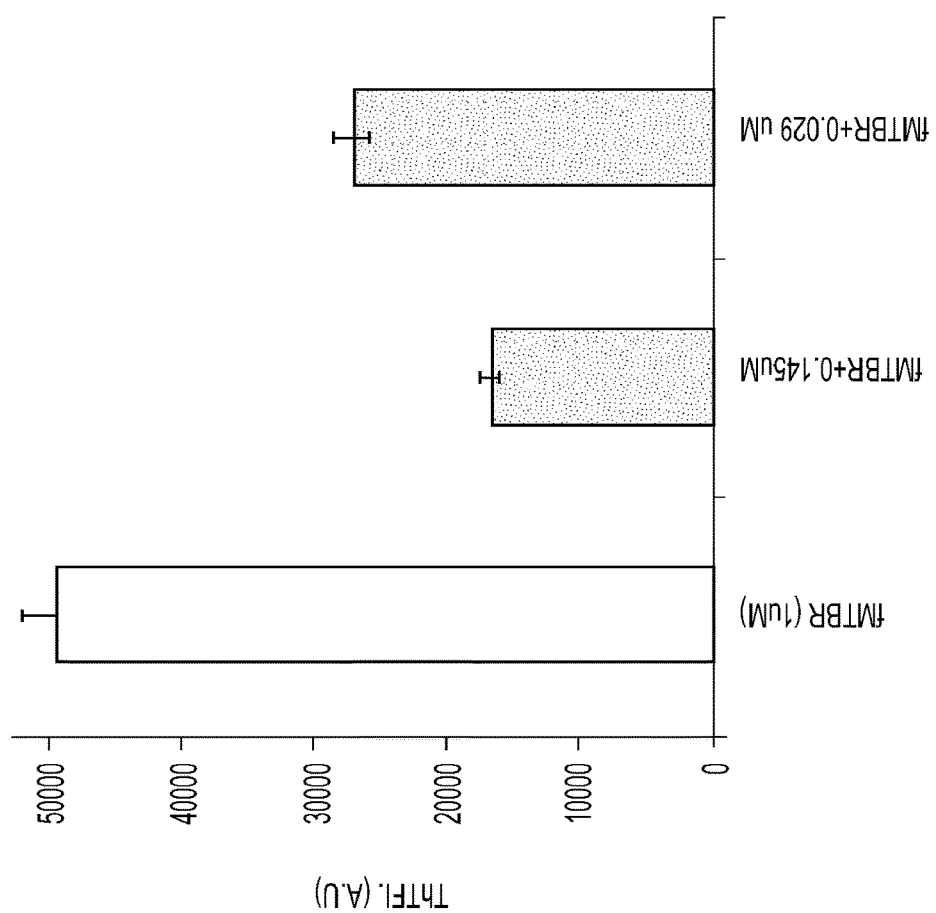
FIG. 36A and FIG. 36B show the ability of rs-g3p (N1N2)-hIgG1-Fc (Construct 6) to disaggregate ftau. Tau fibers were prepared by diluting 40 uM of the microtubule binding repeat region ("MTBR") of tau into 50 mM superoxide dismutase ("Sod"). Various concentrations of Construct 6 and the prepared ftau were incubated in acetate buffer at pH7.0, 37° C. for 72 hrs. ThT fluorescence was recorded in the presence of 5 fold excess ThT.
Figure 36B:
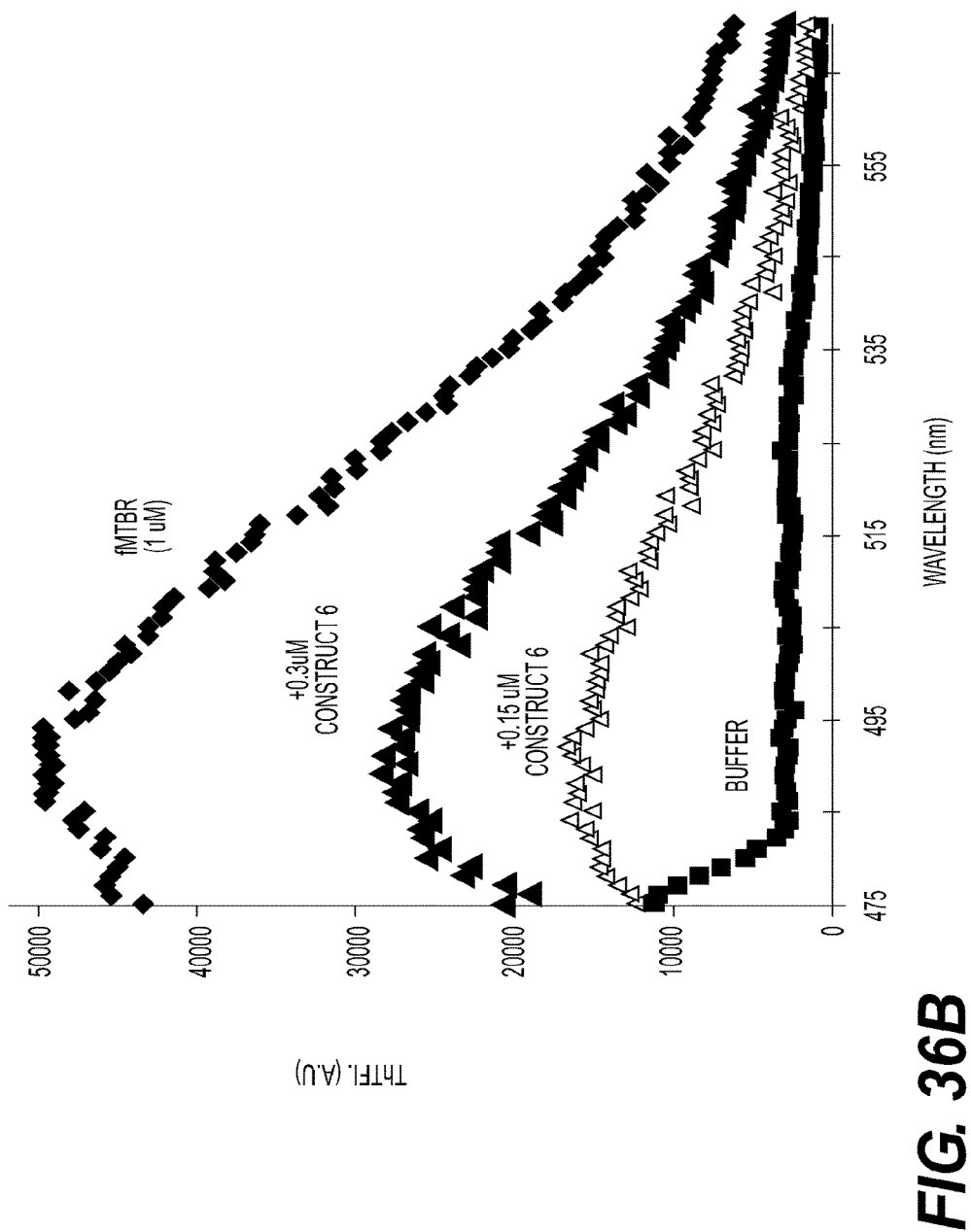
Figure 37A:
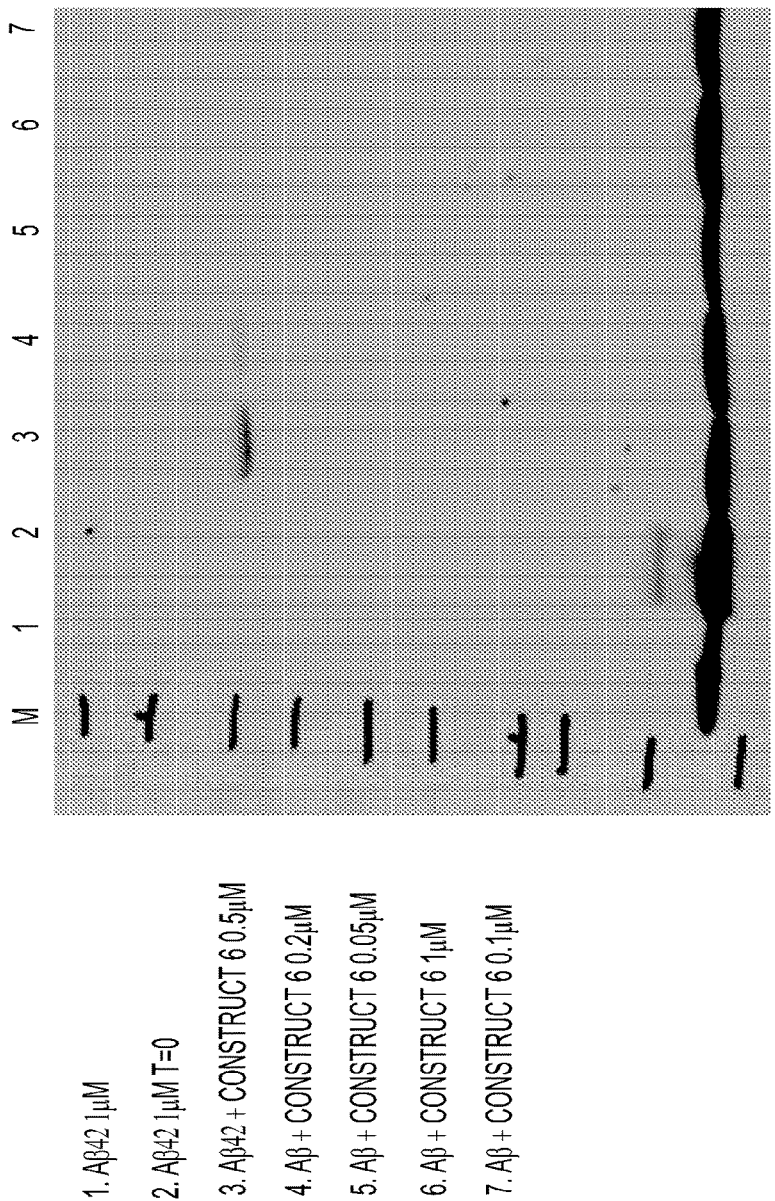
FIG. 37A, FIG. 37B, FIG. 37C, and FIG. 37D present representative experiments showing the inhibition of Aβ42 aggregation by rs-g3p(N1N2)-hIgG1-Fc (Construct 6) and rs-g3p(N1N2) (Construct 3) over time. Aβ42 was dissolved in DMSO and diluted into PBS containing NaN3. Aβ42 was aggregated at 37° C. plus or minus various concentrations of Construct 3 and Construct 6. Aggregation of Aβ42 was measured by ThT fluorescence.
Figure 37B:
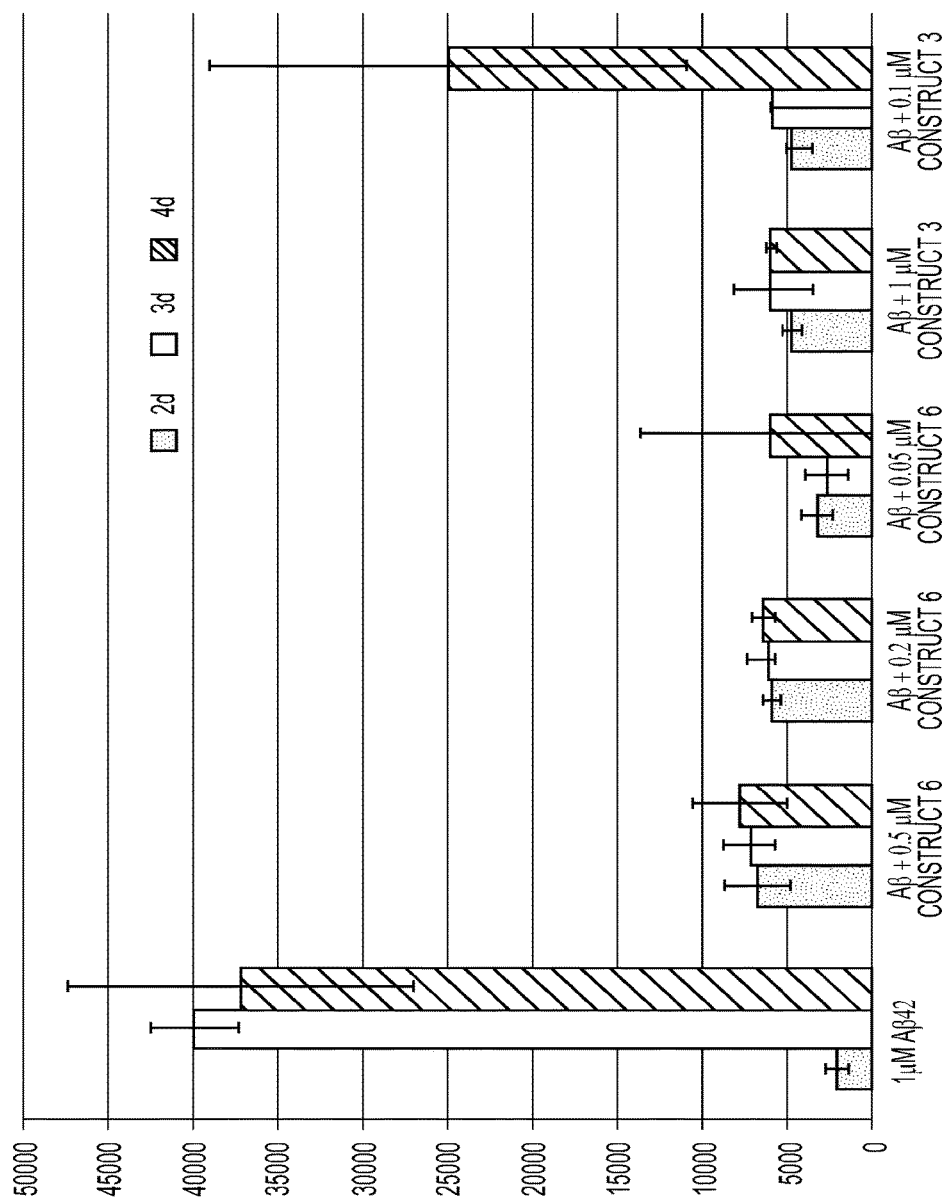
Figure 37C:
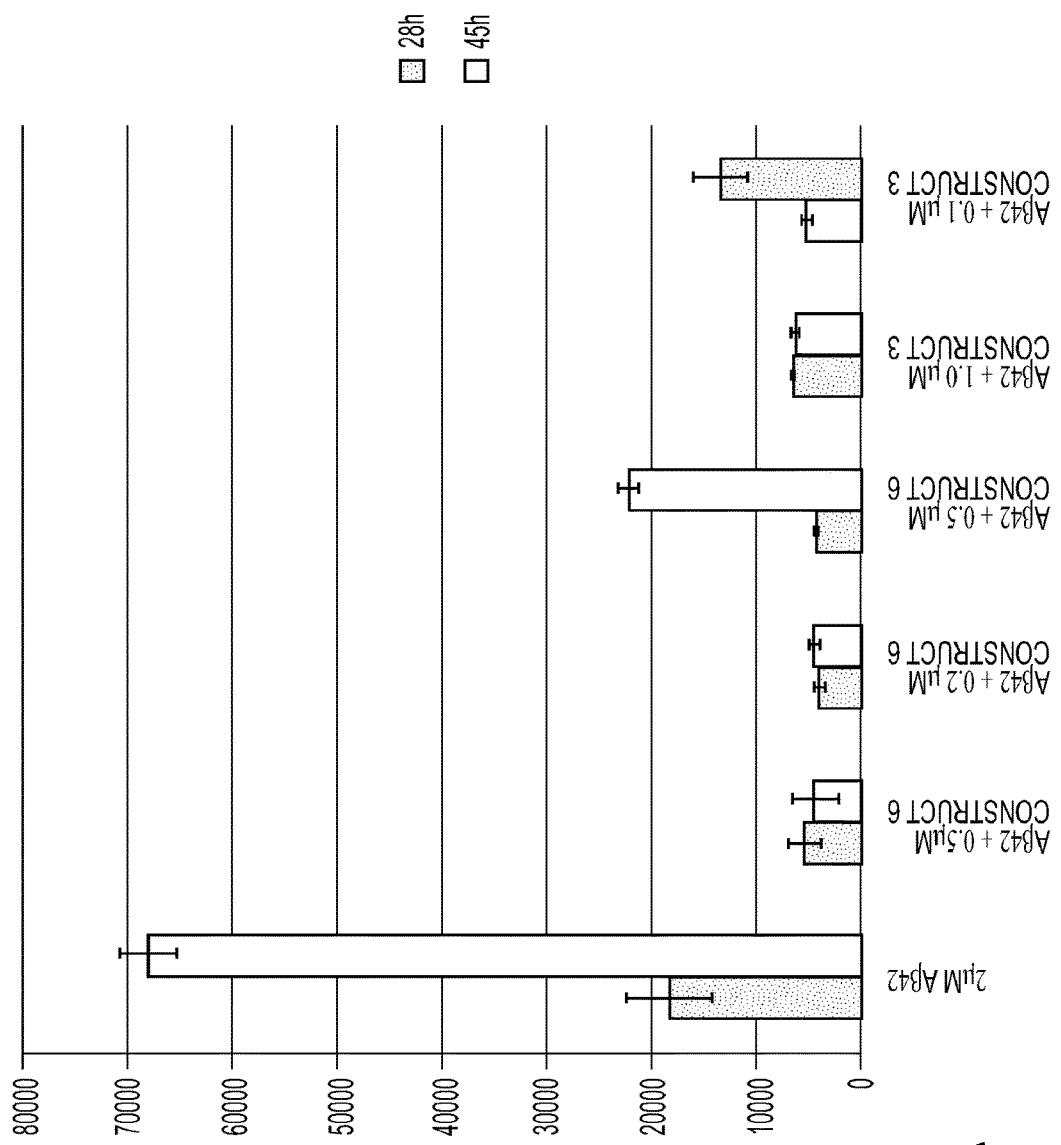
Figure 37D:
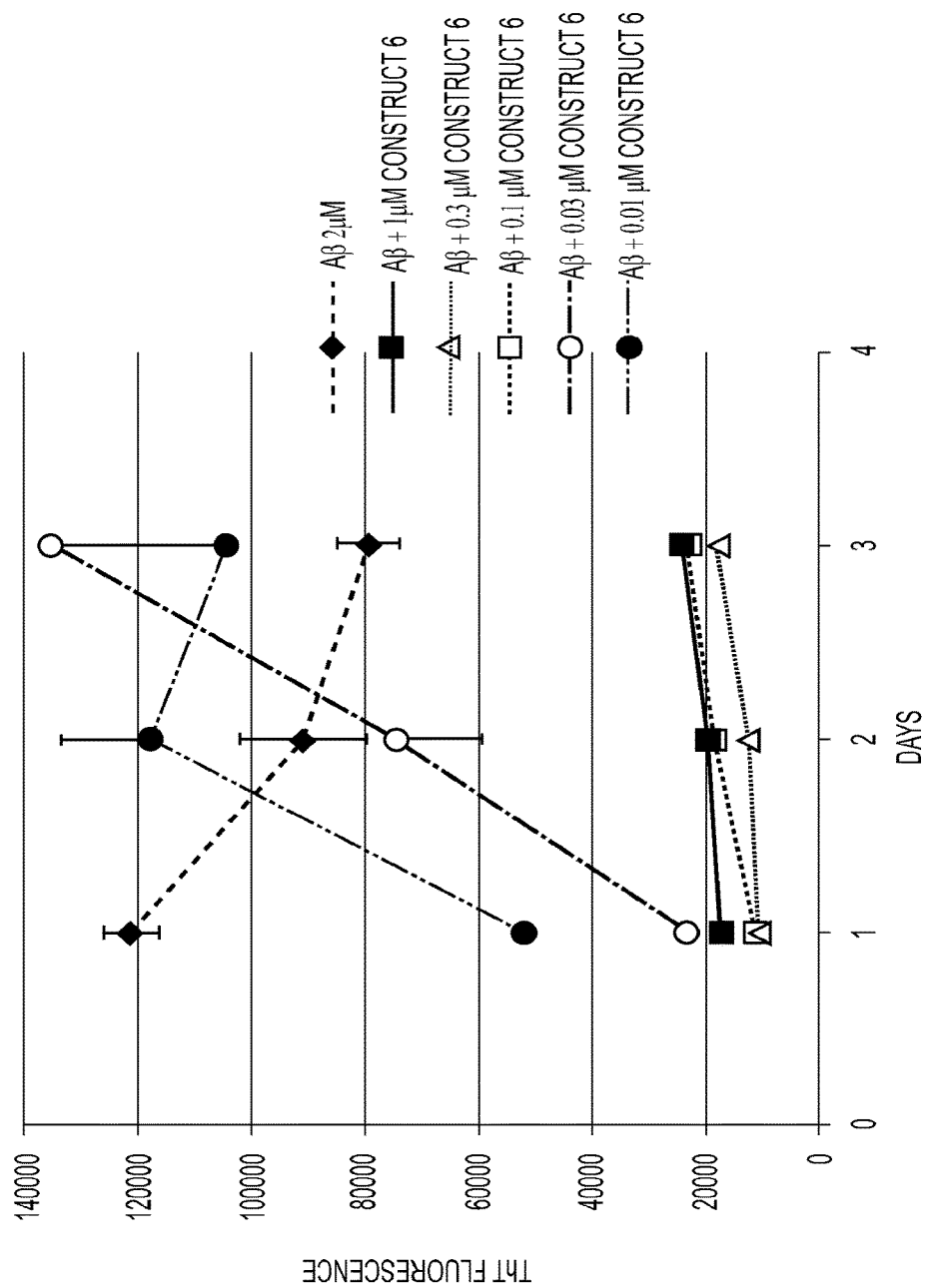

To test whether a g3p fragment can disaggregate tau, a g3p fragment-Ig fusion protein comprising N1 and N2 was tested in a ThT fluorescence assay for its ability to degrade preformed ftau. The results indicate that an N1N2-Ig fusion protein potently disaggregates ftau. See, FIG. 36A and FIG. 36B.

Example 15: N1N2-Ig Fusion Protein Inhibits $PrP^{Sc}$ Accumulation, Aggregation and $PrP^{Sc}$ Formation in a Cell Culture Model of Prion Disease ($N2a22L^{Sc}$)

Prion diseases are characterized by the conversion of normal cellular prion protein ($PrP^c$) to the protease-resistant pathological form $PrP^{Sc}$. $PrP^{Sc}$ is distinguished from $PrP^c$ on the basis of protease resistance: protease partly degrades $PrP^{Sc}$ to form a protease-resistant C-terminal core fragment (PrPres), which has an unglycosylated form with a molecular weight of 19-21 kDa. Inhibition, reversal, and reduction of $PrP^{Sc}$ constitutes a viable therapeutic approach to treatment of several degenerative diseases.

To determine whether a g3p fragment-Ig fusion protein comprising N1 and N2 (Construct 6) interferes with the formation of pathological prion conformers ($PrP^{Sc}$) in in vitro models of prion disease, and to verify disaggregation or change in solubility of PrP in $N2a22L^{Sc}$ cells in the presence or absence of Construct 6, cells were cultured for 24h in the absence or presence of 1 ug/ml Construct 6 or IgG and harvested in lysis buffer. 100 μg of total protein was ultracentrifuged at 4° C. for 90 min at 55,000 rpm in a TLA 100.1 rotor in a Beckman Optima TL ultracentrifuge. 25 μl samples of solubilized pellets and supernatants were subjected to SDS-PAGE and downstream analysis with anti-PrP antibody 6D11 mAb. Increased detergent insolubility precedes acquisition of proteinase K (PK) resistance by $PrP^{Sc}$ or PrP mutants, therefore the ability of Construct 6 to alter PrP solubility was assessed. Construct 6-treated cells exhibited significantly reduced amounts of aggregated/insoluble PrP compared to IgG treated $N2a22L^{Sc}$ cells. See FIG. 38A and FIG. 38B.

Figure 38A:
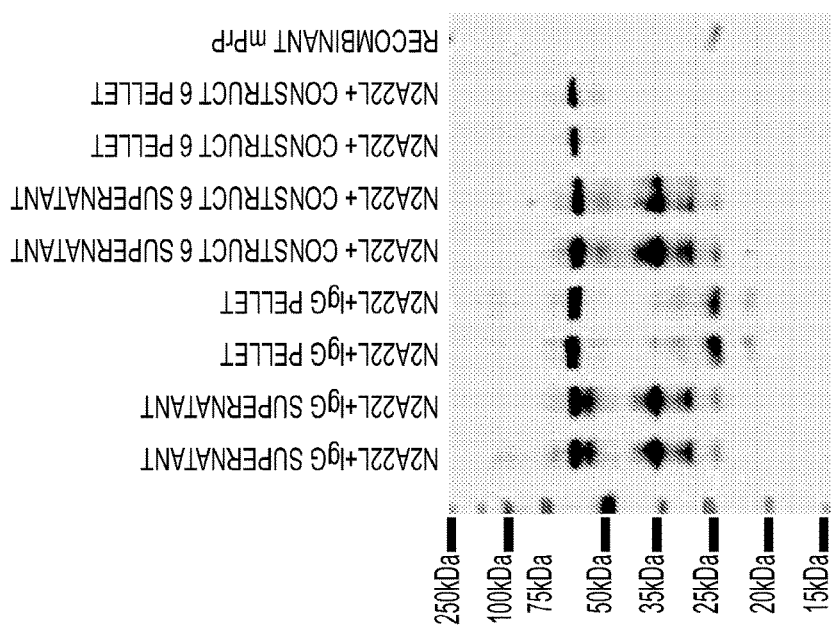
FIG. 38A and FIG. 38B present the results of experiments showing the ability of rs-g3p(N1N2)-hIgG1-Fc (Construct 6) to block the conversion of PrP to PrP-Sc. Construct 6 and IgG cell lysates were subjected to ultra-centrifugation to separate soluble (supernatant) and insoluble (pellet) PrP species. PrP species were visualized biochemically with an anti-PrP monoclonal antibody (6D11). In the presence of IgG, there is a partitioning of PrP in both soluble and insoluble fractions. In the presence of Construct 6, there is limited insoluble PrP. Data represents n=4.
Figure 38B:
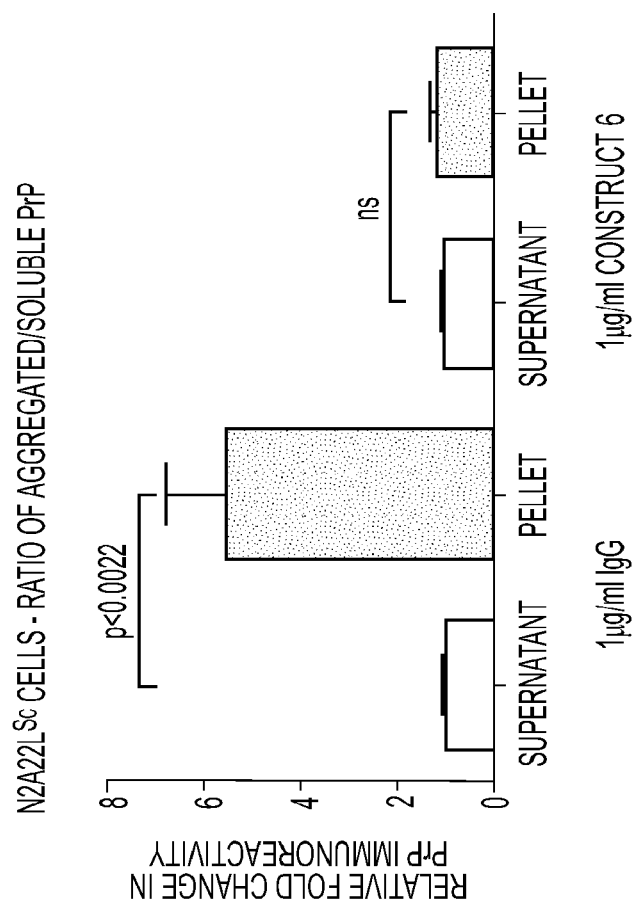
Figure 39A:
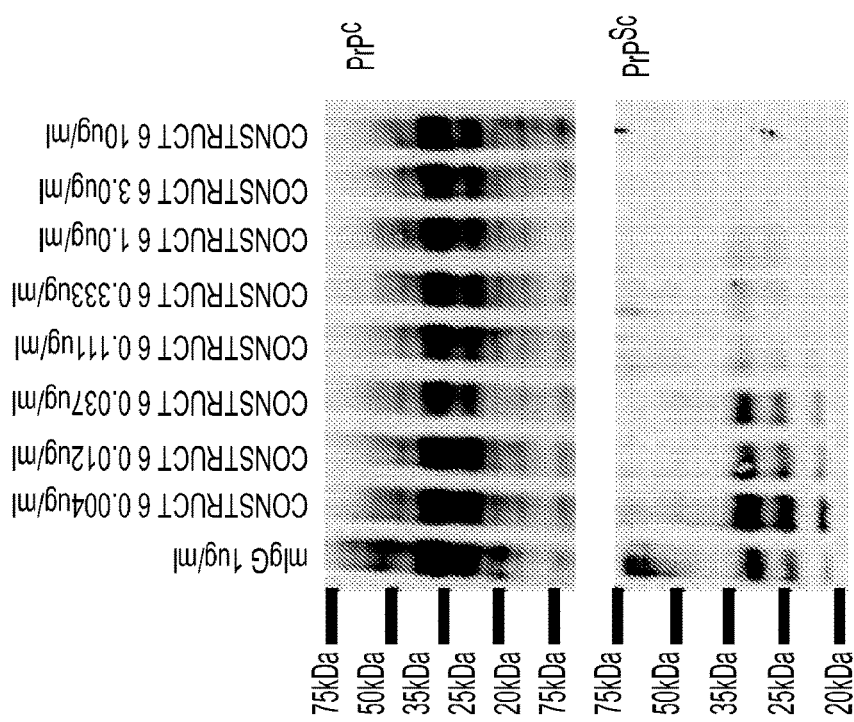
FIG. 39A and FIG. 39B present the results of experiments showing the ability of rs-g3p(N1N2)-hIgG1-Fc (Construct 6) to reduce the accumulation and aggregation of $PrP^{Sc}$ in a cell culture model of prion disease.
Figure 39B:
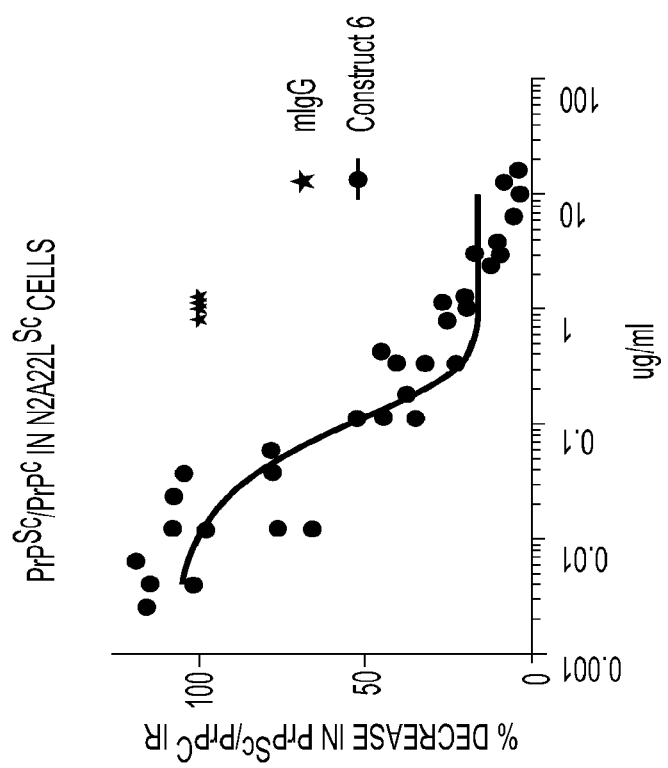

For FIGS. 38A and 38B, $N2a22L^{Sc}$ cells were be generated as described previously (Pankiewicz et al., Eur. J. Neurosci. (2006) 23:2635-2647. Briefly, brains of terminally sick CD-1 mice infected with mouse-adapted 22L prion strain were homogenized by sonication (10% weight/volume) in cold phosphate-buffered saline and 5% dextrose in sterile conditions. For infection, the brain homogenate was further diluted to 2% in Opti-MEM and added to subconfluent six-well plates (Corning, Acton, Mass., USA), 1 mL per 10-cm² well. After 5 h, 1 mL of regular MEM was added and the cells were incubated in the presence of infectious brain homogenate for an additional 12 h. The cells are washed and standard MEM growth media is added. Cells were grown until confluent and then split into 1:2 dilutions and transferred to 25-cm² flasks (Corning). Cells grown in one of the flasks were split 1:2 every 4 days to give rise to subsequent passages, whereas cells grown in the other flask were harvested and homogenized to monitor the level of $PrP^{Sc}$. Based on prior studies, the presence of inoculum derived $PrP^{Sc}$ is only detected in the first and second passages, so passage 4 (P4) cells were utilized for all subsequent studies. Cells were lysed in a homogenizing buffer composed of (50 mM Tris-HCl, pH 7.4, 150 mM NaCl, 1 mM ethylene glycol tetraacetic acid (EGTA), 1 mM Na$_3$VO$_4$, 1 mM NaF, 2.5 mM Na$_4$P$_2$O$_7$, 1 mM β-glycerophosphate, 1% NP-40, 0.25% sodium deoxycholate, 0.5 mM phenylmethylsulfonylfluoride (PMSF), 1 mM leupeptin, 1 mM pepstatin A, 1 mM) or without PMSF for PK digestion) for 5 min at 4° C. and insoluble materials were removed by centrifugation at 10,000 g for 10 min at 4° C. For cellular fractionation, 100 μg of protein was spun at 55,000 rpm for 90 min, after which the pellet was reconstituted in the starting volume. 20% of both pellet and supernatant were resolved and characterized biochemically.

To address whether Construct 6 dose-dependently alters the propagation of P

```
Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Val Asn Ala Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
        290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
        355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 2
<211> LENGTH: 424
<212> TYPE: PRT
<213> ORGANISM: Enterobacteria phage

<400> SEQUENCE: 2

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Gly Ser Glu
                85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125
```

Pro Pro Gly Thr Glu Gln Asn Pro Ala Asn Pro Asn Pro Ser Leu Glu
            130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
            195                 200                 205

His Ser Gly Phe Asn Glu Asp Pro Phe Val Cys Glu Tyr Gln Gly Gln
            210                 215                 220

Ser Ser Asp Leu Pro Gln Pro Val Asn Ala Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Ser Gly
                260                 265                 270

Ser Gly Asp Phe Asp Tyr Glu Lys Met Ala Asn Ala Asn Lys Gly Ala
            275                 280                 285

Met Thr Glu Asn Ala Asp Glu Asn Ala Leu Gln Ser Asp Ala Lys Gly
290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
            325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
            355                 360                 365

Ser Val Glu Cys Arg Pro Tyr Val Phe Gly Ala Gly Lys Pro Tyr Glu
370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
            405                 410                 415

Asn Ile Leu Arg Asn Lys Glu Ser
            420

<210> SEQ ID NO 3
<211> LENGTH: 424
<212> TYPE: PRT
<213> ORGANISM: Enterobacteria phage

<400> SEQUENCE: 3

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Val Cys
        50                  55                  60

Thr Gly Asp Glu Thr Gln Cys Tyr Gly Thr Trp Val Pro Ile Gly Leu

```
                65                  70                  75                  80
Ala Ile Pro Glu Asn Glu Gly Gly Ser Glu Gly Gly Ser Glu
                    85                  90                  95

Gly Gly Gly Ser Glu Gly Gly Thr Lys Pro Pro Glu Tyr Gly Asp
                    100                 105                 110

Thr Pro Ile Pro Gly Tyr Thr Tyr Ile Asn Pro Leu Asp Gly Thr Tyr
                    115                 120                 125

Pro Pro Gly Thr Glu Gln Asn Pro Ala Asn Pro Asn Pro Ser Leu Glu
        130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                    165                 170                 175

Thr Asp Pro Val Lys Thr Tyr Tyr Gln Tyr Thr Pro Val Ser Ser Lys
                180                 185                 190

Ala Met Tyr Asp Ala Tyr Trp Asn Gly Lys Phe Arg Asp Cys Ala Phe
                195                 200                 205

His Ser Gly Phe Asn Glu Asp Pro Phe Val Cys Glu Tyr Gln Gly Gln
            210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Ser Glu Gly Gly Gly
                    245                 250                 255

Ser Glu Gly Gly Gly Ser Glu Gly Gly Ser Gly Gly Gly Ser Gly
                260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
                340                 345                 350

Ser Pro Leu Met Asn Asn Phe Arg Gln Tyr Leu Pro Ser Leu Pro Gln
            355                 360                 365

Ser Val Glu Cys Arg Pro Phe Val Phe Gly Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 4
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
```

<222> LOCATION: (375)..(375)
<223> OTHER INFORMATION: /replace="Tyr"
<220> FEATURE:
<221> NAME/KEY: MOD_RES
<222> LOCATION: (376)..(376)
<223> OTHER INFORMATION: /replace="Gly"
<220> FEATURE:
<221> NAME/KEY: MISC_FEATURE
<222> LOCATION: (375)..(376)
<223> OTHER INFORMATION: note="Residues given in the sequence have no preference with respect to those in the annotations for said positions"

<400> SEQUENCE: 4

```
Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Ser Glu
                85                  90                  95

Gly Gly Gly Ser Glu Gly Gly Thr Lys Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Ser Gly
                260                 265                 270

Ser Gly Asp Phe Asp Tyr Glu Lys Met Ala Asn Ala Asn Lys Gly Ala
            275                 280                 285

Met Thr Glu Asn Ala Asp Glu Asn Ala Leu Gln Ser Asp Ala Lys Gly
290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
            325                 330                 335

Phe Ala Gly Ser Asn Ser Gln Met Ala Gln Val Gly Asp Gly Asp Asn
```

```
                340                 345                 350
Ser Pro Leu Met Asn Asn Phe Arg Gln Tyr Leu Pro Ser Leu Pro Gln
            355                 360                 365

Ser Val Glu Cys Arg Pro Phe Ser Ala Gly Lys Pro Tyr Glu Phe Ser
    370                 375                 380

Ile Asp Cys Asp Lys Ile Asn Leu Phe Arg Gly Val Phe Ala Phe Leu
385                 390                 395                 400

Leu Tyr Val Ala Thr Phe Met Tyr Val Phe Ser Thr Phe Ala Asn Ile
                405                 410                 415

Leu Arg Asn Lys Glu Ser
                420

<210> SEQ ID NO 5
<211> LENGTH: 434
<212> TYPE: PRT
<213> ORGANISM: Enterobacteria phage

<400> SEQUENCE: 5

Met Lys Arg Lys Ile Ala Ile Ser Leu Phe Leu Tyr Ile Pro Leu
1               5                   10                  15

Ser Asn Ala Asp Asn Trp Glu Ser Ile Thr Lys Ser Tyr Tyr Thr Gly
            20                  25                  30

Phe Ala Met Ser Lys Thr Val Glu Ser Lys Asp Gln Asp Gly Lys Thr
        35                  40                  45

Val Arg Lys Glu Val Ile Thr Gln Ala Asp Leu Thr Thr Ala Cys Asn
    50                  55                  60

Asp Ala Lys Ala Ser Ala Gln Asp Val Phe Asn Gln Met Lys Leu Thr
65                  70                  75                  80

Phe Ser Gly Ile Trp Pro Asp Ser Gln Phe Arg Leu Val Thr Gly Asp
                85                  90                  95

Thr Cys Val Tyr Asn Gly Ser Pro Ser Glu Lys Thr Glu Ser Trp Ser
            100                 105                 110

Ile Arg Ala Gln Val Glu Gly Asp Met Gln Arg Ser Val Pro Asp Glu
        115                 120                 125

Glu Pro Ser Glu Gln Thr Pro Glu Glu Ile Cys Glu Ala Lys Pro Pro
    130                 135                 140

Ile Asp Gly Val Phe Asn Asn Val Ser Lys Gly Asp Glu Gly Gly Phe
145                 150                 155                 160

Tyr Ile Asn Tyr Asn Gly Cys Glu Tyr Glu Ala Thr Gly Val Thr Val
                165                 170                 175

Cys Gln Asn Asp Gly Thr Val Cys Ala Ser Ser Ala Trp Lys Pro Thr
            180                 185                 190

Gly Tyr Val Pro Glu Ser Gly Glu Ser Ser Ser Pro Val Lys Asp
        195                 200                 205

Gly Asp Thr Gly Gly Thr Gly Glu Gly Gly Ser Asp Thr Gly Gly Asp
    210                 215                 220

Thr Gly Gly Gly Asp Thr Gly Gly Gly Ser Thr Gly Gly Asp Thr Gly
225                 230                 235                 240

Gly Ser Thr Gly Gly Ser Thr Gly Gly Ser Thr Gly Gly Ser
                245                 250                 255

Thr Gly Lys Ser Leu Thr Lys Glu Asp Val Thr Ala Ala Ile His Asp
            260                 265                 270

Ala Ser Pro Ser Ile Gly Asp Ala Val Lys Asp Ser Leu Thr Glu Asp
        275                 280                 285
```

```
Asn Asp Gln Asn Asp Asn Gln Lys Lys Ala Asp Glu Gln Ser Ala Lys
    290                 295                 300

Ala Ser Ala Ser Val Ser Asp Ala Ile Ser Asp Gly Met Arg Gly Val
305                 310                 315                 320

Gly Asn Phe Val Asp Asp Leu Gly Gly Glu Ser Ser Gln Tyr Gly Ile
                325                 330                 335

Gly Asn Ser Glu Met Asp Leu Ser Val Ser Leu Ala Lys Gly Gln Leu
            340                 345                 350

Gly Ile Asp Leu Glu Gly His Gly Ser Ala Trp Glu Ser Phe Leu Asn
        355                 360                 365

Asp Gly Ala Leu Arg Pro Ser Ile Pro Ser Gly His Gly Cys Thr Asp
370                 375                 380

Phe Val Met Phe Gln Gly Ser Val Tyr Gln Leu Asp Ile Gly Cys Asp
385                 390                 395                 400

Lys Leu Gly Asp Ile Lys Ser Val Leu Ser Trp Val Met Tyr Cys Leu
                405                 410                 415

Thr Phe Trp Tyr Val Phe Gln Ser Ala Thr Ser Leu Leu Arg Lys Gly
                420                 425                 430

Glu Gln

<210> SEQ ID NO 6
<211> LENGTH: 434
<212> TYPE: PRT
<213> ORGANISM: Enterobacteria phage

<400> SEQUENCE: 6

Met Lys Arg Lys Ile Ile Ala Ile Ser Leu Phe Leu Tyr Ile Pro Leu
1               5                   10                  15

Ser Asn Ala Asp Asn Trp Glu Ser Ile Thr Lys Ser Tyr Tyr Thr Gly
            20                  25                  30

Phe Ala Ile Ser Lys Thr Val Glu Ser Lys Asp Lys Asp Gly Lys Pro
        35                  40                  45

Val Arg Lys Glu Val Ile Thr Gln Ala Asp Leu Thr Thr Ala Cys Asn
50                  55                  60

Asp Ala Lys Ala Ser Ala Gln Asn Val Phe Asn Gln Ile Lys Leu Thr
65                  70                  75                  80

Leu Ser Gly Thr Trp Asn Asp Ser Gln Phe Arg Leu Val Thr Gly Asp
                85                  90                  95

Thr Cys Val Tyr Asn Gly Ser Pro Gly Glu Lys Thr Glu Ser Trp Ser
                100                 105                 110

Ile Arg Ala Gln Val Glu Gly Asp Ile Gln Arg Ser Val Pro Asp Glu
            115                 120                 125

Glu Pro Ser Glu Gln Thr Pro Glu Glu Ile Cys Glu Ala Lys Pro Pro
        130                 135                 140

Ile Asp Gly Val Phe Asn Asn Val Phe Lys Gly Asp Glu Gly Gly Phe
145                 150                 155                 160

Tyr Ile Asn Tyr Asn Gly Cys Glu Tyr Glu Ala Thr Gly Val Thr Val
                165                 170                 175

Cys Gln Asn Asp Gly Thr Val Cys Ser Ser Ser Ala Trp Lys Pro Thr
            180                 185                 190

Gly Tyr Val Pro Glu Ser Gly Glu Pro Ser Ser Pro Leu Lys Asp
        195                 200                 205

Gly Asp Thr Gly Gly Thr Gly Glu Gly Gly Ser Asp Thr Gly Gly Asp
210                 215                 220
```

```
Thr Gly Gly Gly Asp Thr Gly Gly Gly Ser Thr Gly Gly Asp Thr Gly
225                 230                 235                 240

Gly Ser Ser Gly Gly Ser Ser Gly Gly Ser Thr Gly Gly Ser
            245                 250                 255

Thr Gly Lys Ser Leu Thr Lys Glu Asp Val Thr Ala Ala Ile His Val
            260                 265                 270

Ala Ser Pro Ser Ile Gly Asp Ala Val Lys Asp Ser Leu Thr Glu Asp
        275                 280                 285

Asn Asp Gln Tyr Asp Asn Gln Lys Lys Ala Asp Glu Gln Ser Ala Lys
    290                 295                 300

Ala Ser Ala Ser Val Ser Asp Ala Ile Ser Asp Gly Met Arg Gly Val
305                 310                 315                 320

Gly Asn Phe Val Asp Asp Phe Gly Gly Glu Ser Ser Gln Tyr Gly Thr
            325                 330                 335

Gly Asn Ser Glu Met Asp Leu Ser Val Ser Leu Ala Lys Gly Gln Leu
            340                 345                 350

Gly Ile Asp Arg Glu Gly His Gly Ser Ala Trp Glu Ser Phe Leu Asn
        355                 360                 365

Asp Gly Ala Leu Arg Pro Ser Ile Pro Thr Gly His Gly Cys Thr Asn
    370                 375                 380

Phe Val Met Tyr Gln Gly Ser Val Tyr Gln Ile Glu Ile Gly Cys Asp
385                 390                 395                 400

Lys Leu Asn Asp Ile Lys Ser Val Leu Ser Trp Val Met Tyr Cys Leu
            405                 410                 415

Thr Phe Trp Tyr Val Phe Gln Ser Val Thr Ser Leu Leu Arg Lys Gly
            420                 425                 430

Glu Gln

<210> SEQ ID NO 7
<211> LENGTH: 434
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: MOD_RES
<222> LOCATION: (35)..(35)
<223> OTHER INFORMATION: /replace="Ile"
<220> FEATURE:
<221> NAME/KEY: MISC_FEATURE
<222> LOCATION: (35)..(35)
<223> OTHER INFORMATION: note="Residue given in the sequence has no
      preference with respect to that in the annotations for said
      position"
<220> FEATURE:
<221> NAME/KEY: MOD_RES
<222> LOCATION: (44)..(44)
<223> OTHER INFORMATION: /replace="Lys"
<220> FEATURE:
<221> NAME/KEY: MISC_FEATURE
<222> LOCATION: (44)..(44)
<223> OTHER INFORMATION: note="Residue given in the sequence has no
      preference with respect to that in the annotations for said
      position"
<220> FEATURE:
<221> NAME/KEY: MOD_RES
<222> LOCATION: (48)..(48)
<223> OTHER INFORMATION: /replace="Pro"
<220> FEATURE:
<221> NAME/KEY: MISC_FEATURE
<222> LOCATION: (48)..(48)
<223> OTHER INFORMATION: note="Residue given in the sequence has no
      preference with respect to that in the annotations for said
```

```
                  position"
<220> FEATURE:
<221> NAME/KEY: MOD_RES
<222> LOCATION: (72)..(72)
<223> OTHER INFORMATION: /replace="Asn"
<220> FEATURE:
<221> NAME/KEY: MISC_FEATURE
<222> LOCATION: (72)..(72)
<223> OTHER INFORMATION: note="Residue given in the sequence has no
      preference with respect to that in the annotations for said
      position"
<220> FEATURE:
<221> NAME/KEY: MOD_RES
<222> LOCATION: (77)..(77)
<223> OTHER INFORMATION: /replace="Ile"
<220> FEATURE:
<221> NAME/KEY: MISC_FEATURE
<222> LOCATION: (77)..(77)
<223> OTHER INFORMATION: note="Residue given in the sequence has no
      preference with respect to that in the annotations for said
      position"
<220> FEATURE:
<221> NAME/KEY: MOD_RES
<222> LOCATION: (81)..(81)
<223> OTHER INFORMATION: /replace="Leu"
<220> FEATURE:
<221> NAME/KEY: MISC_FEATURE
<222> LOCATION: (81)..(81)
<223> OTHER INFORMATION: note="Residue given in the sequence has no
      preference with respect to that in the annotations for said
      position"
<220> FEATURE:
<221> NAME/KEY: MOD_RES
<222> LOCATION: (84)..(84)
<223> OTHER INFORMATION: /replace="Thr"
<220> FEATURE:
<221> NAME/KEY: MISC_FEATURE
<222> LOCATION: (84)..(84)
<223> OTHER INFORMATION: note="Residue given in the sequence has no
      preference with respect to that in the annotations for said
      position"
<220> FEATURE:
<221> NAME/KEY: MOD_RES
<222> LOCATION: (86)..(86)
<223> OTHER INFORMATION: /replace="Asn"
<220> FEATURE:
<221> NAME/KEY: MISC_FEATURE
<222> LOCATION: (86)..(86)
<223> OTHER INFORMATION: note="Residue given in the sequence has no
      preference with respect to that in the annotations for said
      position"
<220> FEATURE:
<221> NAME/KEY: MOD_RES
<222> LOCATION: (105)..(105)
<223> OTHER INFORMATION: /replace="Gly"
<220> FEATURE:
<221> NAME/KEY: MISC_FEATURE
<222> LOCATION: (105)..(105)
<223> OTHER INFORMATION: note="Residue given in the sequence has no
      preference with respect to that in the annotations for said
      position"
<220> FEATURE:
<221> NAME/KEY: MOD_RES
<222> LOCATION: (121)..(121)
<223> OTHER INFORMATION: /replace="Ile"
<220> FEATURE:
<221> NAME/KEY: MISC_FEATURE
<222> LOCATION: (121)..(121)
<223> OTHER INFORMATION: note="Residue given in the sequence has no
      preference with respect to that in the annotations for said
      position"
<220> FEATURE:
<221> NAME/KEY: MOD_RES
<222> LOCATION: (153)..(153)
<223> OTHER INFORMATION: /replace="Phe"
<220> FEATURE:
<221> NAME/KEY: MISC_FEATURE
<222> LOCATION: (153)..(153)
<223> OTHER INFORMATION: note="Residue given in the sequence has no
```

```
      preference with respect to that in the annotations for said
      position"
<220> FEATURE:
<221> NAME/KEY: MOD_RES
<222> LOCATION: (185)..(185)
<223> OTHER INFORMATION: /replace="Ser"
<220> FEATURE:
<221> NAME/KEY: MISC_FEATURE
<222> LOCATION: (185)..(185)
<223> OTHER INFORMATION: note="Residue given in the sequence has no
      preference with respect to that in the annotations for said
      position"
<220> FEATURE:
<221> NAME/KEY: MOD_RES
<222> LOCATION: (201)..(201)
<223> OTHER INFORMATION: /replace="Pro"
<220> FEATURE:
<221> NAME/KEY: MISC_FEATURE
<222> LOCATION: (201)..(201)
<223> OTHER INFORMATION: note="Residue given in the sequence has no
      preference with respect to that in the annotations for said
      position"
<220> FEATURE:
<221> NAME/KEY: MOD_RES
<222> LOCATION: (206)..(206)
<223> OTHER INFORMATION: /replace="Leu"
<220> FEATURE:
<221> NAME/KEY: MISC_FEATURE
<222> LOCATION: (206)..(206)
<223> OTHER INFORMATION: note="Residue given in the sequence has no
      preference with respect to that in the annotations for said
      position"
<220> FEATURE:
<221> NAME/KEY: MOD_RES
<222> LOCATION: (243)..(243)
<223> OTHER INFORMATION: /replace="Ser"
<220> FEATURE:
<221> NAME/KEY: MISC_FEATURE
<222> LOCATION: (243)..(243)
<223> OTHER INFORMATION: note="Residue given in the sequence has no
      preference with respect to that in the annotations for said
      position"
<220> FEATURE:
<221> NAME/KEY: MOD_RES
<222> LOCATION: (248)..(248)
<223> OTHER INFORMATION: /replace="Ser"
<220> FEATURE:
<221> NAME/KEY: MISC_FEATURE
<222> LOCATION: (248)..(248)
<223> OTHER INFORMATION: note="Residue given in the sequence has no
      preference with respect to that in the annotations for said
      position"
<220> FEATURE:
<221> NAME/KEY: MOD_RES
<222> LOCATION: (272)..(272)
<223> OTHER INFORMATION: /replace="Val"
<220> FEATURE:
<221> NAME/KEY: MISC_FEATURE
<222> LOCATION: (272)..(272)
<223> OTHER INFORMATION: note="Residue given in the sequence has no
      preference with respect to that in the annotations for said
      position"
<220> FEATURE:
<221> NAME/KEY: MOD_RES
<222> LOCATION: (292)..(292)
<223> OTHER INFORMATION: /replace="Tyr"
<220> FEATURE:
<221> NAME/KEY: MISC_FEATURE
<222> LOCATION: (292)..(292)
<223> OTHER INFORMATION: note="Residue given in the sequence has no
      preference with respect to that in the annotations for said
      position"
<220> FEATURE:
<221> NAME/KEY: MOD_RES
<222> LOCATION: (327)..(327)
<223> OTHER INFORMATION: /replace="Phe"
<220> FEATURE:
<221> NAME/KEY: MISC_FEATURE
<222> LOCATION: (327)..(327)
```

```
<223> OTHER INFORMATION: note="Residue given in the sequence has no
      preference with respect to that in the annotations for said
      position"
<220> FEATURE:
<221> NAME/KEY: MOD_RES
<222> LOCATION: (336)..(336)
<223> OTHER INFORMATION: /replace="Thr"
<220> FEATURE:
<221> NAME/KEY: MISC_FEATURE
<222> LOCATION: (336)..(336)
<223> OTHER INFORMATION: note="Residue given in the sequence has no
      preference with respect to that in the annotations for said
      position"
<220> FEATURE:
<221> NAME/KEY: MOD_RES
<222> LOCATION: (356)..(356)
<223> OTHER INFORMATION: /replace="Arg"
<220> FEATURE:
<221> NAME/KEY: MISC_FEATURE
<222> LOCATION: (356)..(356)
<223> OTHER INFORMATION: note="Residue given in the sequence has no
      preference with respect to that in the annotations for said
      position"
<220> FEATURE:
<221> NAME/KEY: MOD_RES
<222> LOCATION: (378)..(378)
<223> OTHER INFORMATION: /replace="Thr"
<220> FEATURE:
<221> NAME/KEY: MISC_FEATURE
<222> LOCATION: (378)..(378)
<223> OTHER INFORMATION: note="Residue given in the sequence has no
      preference with respect to that in the annotations for said
      position"
<220> FEATURE:
<221> NAME/KEY: MOD_RES
<222> LOCATION: (384)..(384)
<223> OTHER INFORMATION: /replace="Asn"
<220> FEATURE:
<221> NAME/KEY: MISC_FEATURE
<222> LOCATION: (384)..(384)
<223> OTHER INFORMATION: note="Residue given in the sequence has no
      preference with respect to that in the annotations for said
      position"
<220> FEATURE:
<221> NAME/KEY: MOD_RES
<222> LOCATION: (388)..(388)
<223> OTHER INFORMATION: /replace="Tyr"
<220> FEATURE:
<221> NAME/KEY: MISC_FEATURE
<222> LOCATION: (388)..(388)
<223> OTHER INFORMATION: note="Residue given in the sequence has no
      preference with respect to that in the annotations for said
      position"
<220> FEATURE:
<221> NAME/KEY: MOD_RES
<222> LOCATION: (395)..(395)
<223> OTHER INFORMATION: /replace="Ile"
<220> FEATURE:
<221> NAME/KEY: MOD_RES
<222> LOCATION: (396)..(396)
<223> OTHER INFORMATION: /replace="Glu"
<220> FEATURE:
<221> NAME/KEY: MISC_FEATURE
<222> LOCATION: (395)..(396)
<223> OTHER INFORMATION: note="Residues given in the sequence have no
      preference with respect to those in the annotations for said
      positions"
<220> FEATURE:
<221> NAME/KEY: MOD_RES
<222> LOCATION: (403)..(403)
<223> OTHER INFORMATION: /replace="Asn"
<220> FEATURE:
<221> NAME/KEY: MISC_FEATURE
<222> LOCATION: (403)..(403)
<223> OTHER INFORMATION: note="Residue given in the sequence has no
      preference with respect to that in the annotations for said
      position"
<220> FEATURE:
<221> NAME/KEY: MOD_RES
```

```
<222> LOCATION: (425)..(425)
<223> OTHER INFORMATION: /replace="Val"
<220> FEATURE:
<221> NAME/KEY: MISC_FEATURE
<222> LOCATION: (425)..(425)
<223> OTHER INFORMATION: note="Residue given in the sequence has no
      preference with respect to that in the annotations for said
      position"

<400> SEQUENCE: 7
```

| | | | | | | | | | | | | | | |
|---|---|---|---|---|---|---|---|---|---|---|---|---|---|---|
| Met | Lys | Arg | Lys | Ile | Ile | Ala | Ile | Ser | Leu | Phe | Leu | Tyr | Ile | Pro | Leu |
| 1 | | | | 5 | | | | | 10 | | | | | 15 | |
| Ser | Asn | Ala | Asp | Asn | Trp | Glu | Ser | Ile | Thr | Lys | Ser | Tyr | Tyr | Thr | Gly |
| | | | 20 | | | | | 25 | | | | | 30 | | |
| Phe | Ala | Met | Ser | Lys | Thr | Val | Glu | Ser | Lys | Asp | Gln | Asp | Gly | Lys | Thr |
| | | 35 | | | | | 40 | | | | | 45 | | | |
| Val | Arg | Lys | Glu | Val | Ile | Thr | Gln | Ala | Asp | Leu | Thr | Thr | Ala | Cys | Asn |
| 50 | | | | | 55 | | | | | 60 | | | | | |
| Asp | Ala | Lys | Ala | Ser | Ala | Gln | Asp | Val | Phe | Asn | Gln | Met | Lys | Leu | Thr |
| 65 | | | | 70 | | | | | 75 | | | | | 80 | |
| Phe | Ser | Gly | Ile | Trp | Pro | Asp | Ser | Gln | Phe | Arg | Leu | Val | Thr | Gly | Asp |
| | | | | 85 | | | | | 90 | | | | | 95 | |
| Thr | Cys | Val | Tyr | Asn | Gly | Ser | Pro | Ser | Glu | Lys | Thr | Glu | Ser | Trp | Ser |
| | | | 100 | | | | | 105 | | | | | 110 | | |
| Ile | Arg | Ala | Gln | Val | Glu | Gly | Asp | Met | Gln | Arg | Ser | Val | Pro | Asp | Glu |
| | | 115 | | | | | 120 | | | | | 125 | | | |
| Glu | Pro | Ser | Glu | Gln | Thr | Pro | Glu | Glu | Ile | Cys | Glu | Ala | Lys | Pro | Pro |
| | | | | 130 | | | | | 135 | | | | | 140 | |
| Ile | Asp | Gly | Val | Phe | Asn | Asn | Val | Ser | Lys | Gly | Asp | Glu | Gly | Gly | Phe |
| 145 | | | | | 150 | | | | | 155 | | | | | 160 |
| Tyr | Ile | Asn | Tyr | Asn | Gly | Cys | Glu | Tyr | Glu | Ala | Thr | Gly | Val | Thr | Val |
| | | | | 165 | | | | | 170 | | | | | 175 | |
| Cys | Gln | Asn | Asp | Gly | Thr | Val | Cys | Ala | Ser | Ser | Ala | Trp | Lys | Pro | Thr |
| | | | 180 | | | | | 185 | | | | | 190 | | |
| Gly | Tyr | Val | Pro | Glu | Ser | Gly | Glu | Ser | Ser | Ser | Pro | Val | Lys | Asp |
| | | 195 | | | | | 200 | | | | | 205 | | | |
| Gly | Asp | Thr | Gly | Gly | Thr | Gly | Glu | Gly | Gly | Ser | Asp | Thr | Gly | Gly | Asp |
| | 210 | | | | | 215 | | | | | 220 | | | | |
| Thr | Gly | Gly | Gly | Asp | Thr | Gly | Gly | Ser | Thr | Gly | Gly | Asp | Thr | Gly |
| 225 | | | | | 230 | | | | | 235 | | | | | 240 |
| Gly | Ser | Thr | Gly | Gly | Ser | Thr | Gly | Gly | Ser | Thr | Gly | Gly | Ser |
| | | | | 245 | | | | | 250 | | | | | 255 | |
| Thr | Gly | Lys | Ser | Leu | Thr | Lys | Glu | Asp | Val | Thr | Ala | Ala | Ile | His | Asp |
| | | | 260 | | | | | 265 | | | | | 270 | | |
| Ala | Ser | Pro | Ser | Ile | Gly | Asp | Ala | Val | Lys | Asp | Ser | Leu | Thr | Glu | Asp |
| | | 275 | | | | | 280 | | | | | 285 | | | |
| Asn | Asp | Gln | Asn | Asp | Asn | Gln | Lys | Lys | Ala | Asp | Glu | Gln | Ser | Ala | Lys |
| | | | | 290 | | | | | 295 | | | | | 300 | |
| Ala | Ser | Ala | Ser | Val | Ser | Asp | Ala | Ile | Ser | Asp | Gly | Met | Arg | Gly | Val |
| 305 | | | | | 310 | | | | | 315 | | | | | 320 |
| Gly | Asn | Phe | Val | Asp | Asp | Leu | Gly | Gly | Glu | Ser | Ser | Gln | Tyr | Gly | Ile |
| | | | | 325 | | | | | 330 | | | | | 335 | |
| Gly | Asn | Ser | Glu | Met | Asp | Leu | Ser | Val | Ser | Leu | Ala | Lys | Gly | Gln | Leu |
| | | | 340 | | | | | 345 | | | | | 350 | | |
| Gly | Ile | Asp | Leu | Glu | Gly | His | Gly | Ser | Ala | Trp | Glu | Ser | Phe | Leu | Asn |
| | | | | 355 | | | | | 360 | | | | | 365 | |

```
Asp Gly Ala Leu Arg Pro Ser Ile Pro Ser Gly His Gly Cys Thr Asp
        370                 375                 380

Phe Val Met Phe Gln Gly Ser Val Tyr Gln Leu Asp Ile Gly Cys Asp
385                 390                 395                 400

Lys Leu Gly Asp Ile Lys Ser Val Leu Ser Trp Val Met Tyr Cys Leu
                405                 410                 415

Thr Phe Trp Tyr Val Phe Gln Ser Ala Thr Ser Leu Leu Arg Lys Gly
                420                 425                 430

Glu Gln

<210> SEQ ID NO 8
<211> LENGTH: 460
<212> TYPE: PRT
<213> ORGANISM: Enterobacteria phage

<400> SEQUENCE: 8

Met Lys Lys Ile Ile Ile Ala Leu Phe Phe Ala Pro Phe Phe Thr His
1               5                   10                  15

Ala Thr Thr Asp Ala Glu Cys Leu Ser Lys Pro Ala Phe Asp Gly Thr
                20                  25                  30

Leu Ser Asn Val Trp Lys Glu Gly Asp Ser Arg Tyr Ala Asn Phe Glu
            35                  40                  45

Asn Cys Ile Tyr Glu Leu Ser Gly Ile Gly Ile Gly Tyr Asp Asn Asp
    50                  55                  60

Thr Ser Cys Asn Gly His Trp Thr Pro Val Arg Ala Ala Asp Gly Ser
65                  70                  75                  80

Gly Asn Gly Gly Asp Asp Asn Ser Ser Gly Gly Ser Asn Gly Asp
                85                  90                  95

Ser Gly Asn Asn Ser Thr Pro Asp Thr Val Thr Pro Gly Gln Thr Val
                100                 105                 110

Asn Leu Pro Ser Asp Leu Ser Thr Leu Ser Ile Pro Ala Asn Val Val
            115                 120                 125

Lys Ser Asp Ser Ile Gly Ser Gln Phe Ser Leu Tyr Thr Asn Ala Ser
    130                 135                 140

Cys Thr Met Cys Ser Gly Tyr Tyr Leu Ser Asn Asn Ala Asp Ser Ile
145                 150                 155                 160

Ala Ile Ala Asn Ile Thr Glu Thr Val Lys Ala Asp Tyr Asn Gln Pro
                165                 170                 175

Asp Met Trp Phe Glu Gln Thr Asp Ser Asp Gly Asn His Val Lys Ile
            180                 185                 190

Leu Gln Asn Ser Tyr Lys Ala Val Ser Tyr Asn Val Glu Ser Lys Gln
    195                 200                 205

Ser Asp Val Asn Asn Pro Thr Tyr Ile Asn Tyr Ser Tyr Ser Val Asn
    210                 215                 220

Val Lys Gln Val Ser Tyr Asp Thr Ser Asn Val Cys Ile Met Asn Trp
225                 230                 235                 240

Glu Thr Phe Gln Asn Lys Cys Asp Ala Ser Arg Ala Val Leu Ile Thr
                245                 250                 255

Asp Thr Val Thr Pro Ser Tyr Ser Arg Asn Ile Thr Ile Gln Ser Asn
            260                 265                 270

Ile Asn Tyr Gln Gly Ser Asn Gly Ser Gly Gly Ser Gly
    275                 280                 285

Gly Ser Gly Asn Asp Gly Gly Thr Gly Asn Asn Gly Asn Gly Thr
                290                 295                 300
```

```
Gly Asp Phe Asp Tyr Val Lys Met Ala Asn Ala Asn Lys Asp Ala Leu
305                 310                 315                 320

Thr Glu Ser Phe Asp Leu Ser Ala Leu Gln Ala Asp Thr Gly Ala Ser
                325                 330                 335

Leu Asp Gly Ser Val Gln Gly Thr Leu Asp Ser Leu Ser Gly Phe Ser
            340                 345                 350

Asp Ser Ile Gly Gly Leu Val Gly Asn Gly Ser Ala Ile Ser Gly Glu
        355                 360                 365

Phe Ala Gly Ser Ser Ala Ala Met Asn Ala Ile Gly Glu Gly Asp Lys
    370                 375                 380

Ser Pro Leu Leu Asp Ser Leu Ser Phe Leu Lys Asp Gly Leu Phe Pro
385                 390                 395                 400

Ala Leu Pro Glu Phe Lys Gln Cys Thr Pro Phe Val Phe Ala Pro Gly
                405                 410                 415

Lys Glu Tyr Glu Phe Ile Ile Glu Cys Lys Tyr Ile Asp Met Phe Lys
            420                 425                 430

Gly Ile Phe Ala Phe Ile Leu Tyr Phe Trp Thr Phe Val Thr Val Tyr
        435                 440                 445

Asp Ser Phe Ser Gly Ile Leu Arg Lys Gly Arg Gly
    450                 455                 460

<210> SEQ ID NO 9
<211> LENGTH: 506
<212> TYPE: PRT
<213> ORGANISM: Enterobacteria phage

<400> SEQUENCE: 9

Met Tyr Arg Met Gln Leu Leu Ser Cys Ile Ala Leu Ser Leu Ala Leu
1               5                   10                  15

Val Thr Asn Ser Met Ala Glu Thr Val Glu Ser Cys Leu Ala Lys Pro
                20                  25                  30

His Thr Glu Asn Ser Phe Thr Asn Val Trp Lys Asp Asp Lys Thr Leu
            35                  40                  45

Asp Arg Tyr Ala Asn Tyr Glu Gly Cys Leu Trp Asn Ala Thr Gly Val
        50                  55                  60

Val Val Cys Thr Gly Asp Glu Thr Gln Cys Tyr Gly Thr Trp Val Pro
65                  70                  75                  80

Ile Gly Leu Ala Ile Pro Glu Asn Glu Gly Gly Ser Glu Gly Gly
                85                  90                  95

Gly Ser Glu Gly Gly Gly Ser Glu Gly Gly Gly Thr Lys Pro Pro Glu
            100                 105                 110

Tyr Gly Asp Thr Pro Ile Pro Gly Tyr Thr Tyr Ile Asn Pro Leu Asp
        115                 120                 125

Gly Thr Tyr Pro Pro Gly Thr Glu Gln Asn Pro Ala Asn Pro Asn Pro
    130                 135                 140

Ser Leu Glu Glu Ser Gln Pro Leu Asn Thr Phe Met Phe Gln Asn Asn
145                 150                 155                 160

Arg Phe Arg Asn Arg Gln Gly Ala Leu Thr Val Tyr Thr Gly Thr Val
                165                 170                 175

Thr Gln Gly Thr Asp Pro Val Lys Thr Tyr Tyr Gln Tyr Thr Pro Val
            180                 185                 190

Ser Ser Lys Ala Met Tyr Asp Ala Tyr Trp Asn Gly Lys Phe Arg Asp
        195                 200                 205

Cys Ala Phe His Ser Gly Phe Asn Glu Asp Pro Phe Val Cys Glu Tyr
```

Gln Gly Gln Ser Ser Asp Leu Pro Gln Pro Pro Val Asn Ala Gly Gly
225                 230                 235                 240

Gly Ser Gly Gly Gly Ser Gly Gly Ser Glu Gly Gly Ser Glu
            245                 250                 255

Gly Gly Gly Ser Glu Gly Gly Ser Glu Gly Gly Ser Gly Gly
            260                 265                 270

Gly Ser Gly Ser Gly Ala Met Val Arg Ser Pro Cys Pro Ser Cys
        275                 280                 285

Pro Ala Pro Glu Phe Leu Gly Gly Pro Ser Val Phe Leu Phe Pro Pro
290                 295                 300

Lys Pro Lys Asp Thr Leu Met Ile Ser Arg Thr Pro Glu Val Thr Cys
305                 310                 315                 320

Val Val Val Asp Val Ser Gln Glu Asp Pro Glu Val Gln Phe Asn Trp
                325                 330                 335

Tyr Val Asp Gly Val Glu Val His Asn Ala Lys Thr Lys Pro Arg Glu
            340                 345                 350

Glu Gln Phe Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
        370                 375                 380

Lys Gly Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Gln Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
450                 455                 460

Leu Tyr Ser Arg Leu Thr Val Asp Lys Ser Arg Trp Gln Glu Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 10
<211> LENGTH: 6407
<212> TYPE: DNA
<213> ORGANISM: Enterobacteria phage

<400> SEQUENCE: 10
aacgctacta ctattagtag aattgatgcc acctttcag ctcgcgcccc aaatgaaaat    60
atagctaaac aggttattga ccatttgcga aatgtatcta atggtcaaac taaatctact   120
cgttcgcaga attgggaatc aactgttaca tggaatgaaa cttccagaca ccgtacttta   180
gttgcatatt taaaacatgt tgagctacag caccagattc agcaattaag ctctaagcca   240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tctttttgat gcaatccgct ttgcttctga ctataatagt   420
cagggtaaag acctgatttt tgatttatgg tcattctcgt tttctgaact gtttaaagca   480

```
tttgagggggg attcaatgaa tatttatgac gattccgcag tattggacgc tatccagtct    540
aaacatttta ctattacccc ctctggcaaa acttcttttg caaaagcctc tcgctatttt    600 ggttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagccttt    1560 tttttggaga ttttcaacgt gaaaaaatta ttattcgcaa ttcctttagt tgttcctttc   1620
tattctcact ccgctgaaac tgttgaaagt tgtttagcaa acccccatac agaaaattca   1680
tttactaacg tctggaaaga cgacaaaact ttagatcgtt acgctaacta tgagggctgt   1740
ctgtggaatg ctacaggcgt tgtagtttgt actggtgacg aaactcagtg ttacggtaca   1800
tgggttccta ttgggcttgc tatccctgaa atgagggggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cacttttact   2100
caaggcactg acccogttaa aacttattac cagtacactc ctgtatcatc aaaagccatg   2160
tatgacgctt actggaacgg taaattcaga gactgcgctt ccattctgg ctttaatgag   2220 gatccattcg tttgtgaata tcaaggccaa tcgtctgacc tgcctcaacc tcctgtcaat   2280 gctgcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg tgacggtga taattcacct   2640 ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
```

```
tttgctaaca tactgcgtaa taaggagtct taatcatgcc agttcttttg ggtattccgt    2880
tattattgcg tttcctcggt ttccttctgg taactttgtt cggctatctg cttacttttc    2940
ttaaaaaggg cttcggtaag atagctattg ctatttcatt gtttcttgct cttattattg    3000
ggcttaactc aattcttgtg ggttatctct ctgatattag cgctcaatta ccctctgact    3060
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg    3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg ctttttctag taattatgat    3840
tccggtgttt attcttattt aacgccttat ttatcacacg gtcggtattt caaaccatta    3900
aatttaggtc agaagatgaa attaactaaa atatatttga aaagttttc tcgcgttctt    3960
tgtcttgcga ttggatttgc atcagcattt acatatagtt ataacccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttctttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gcaaataatt ttgatatggt aggttctatt ccttccatta ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat gtttgtaaa    4680
gtctaatact tctaaatcct caaatgtatt atctattgac ggctctaatc tattagttgt    4740
tagtgctcct aaagatattt tagataacct tcctcaattc ctttcaactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt atttttaatg gcgatgtttt    4980
agggctatca gttcgcgcat taaagactaa tagccattca aaaatattgt ctgtgccacg    5040
tattcttacg ctttcaggtc agaagggttc tatctctgtt ggccagaatg tcccttttat    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
```

-continued

```
tctggatatt accagcaagg ccgatagttt gagttcttct actcaggcaa gtgatgttat      5280
tactaatcaa agaagtattg ctacaacggt taatttgcgt gatggacaga ctctttttact    5340 cggtggcctc actgattata aaaacacttc tcaggattct ggcgtaccgt tcctgtctaa      5400 aatccctttta atcggcctcc tgtttagctc ccgctctgat tctaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
gggggctccc tttaggggttc cgatttagtg ctttacggca cctcgacccc aaaaaacttg   5700
atttgggtga tggttcacgt agtgggccat cgccctgata acggttttt cgccctttga     5760 cgttggagtc cacgttcttt aatagtggac tcttgttcca aactggaaca acactcaacc    5820
ctatctcggg ctattctttt gatttataag ggattttgcc gatttcggcc tattggttaa     5880
aaaatgagct gatttaacaa aaatttaacg cgaattttaa caaaatatta acgtttacaa    5940
tttaaatatt tgcttataca atcttcctgt ttttggggct tttctgatta tcaaccgggg    6000
tacatatgat tgacatgcta gttttacgat taccgttcat cgattctctt gtttgctcca     6060
gactctcagg caatgacctg atagcctttg tagacctctc aaaaatagct accctctccg     6120
gcattaattt atcagctaga acggttgaat atcatattga tggtgatttg actgtctccg     6180
gcctttctca ccctttttgaa tctttaccta cacattactc aggcattgca tttaaaatat   6240
atgagggttc taaaaatttt tatccttgcg ttgaaataaa ggcttctccc gcaaaagtat    6300
tacagggtca taatgttttt ggtacaaccg atttagcttt atgctctgag gctttattgc    6360
ttaattttgc taattctttg ccttgcctgt atgatttatt ggatgtt                  6407
```

<210> SEQ ID NO 11
<211> LENGTH: 506
<212> TYPE: PRT
<213> ORGANISM: Enterobacteria phage

<400> SEQUENCE: 11

```
Met Tyr Arg Met Gln Leu Leu Ser Cys Ile Ala Leu Ser Leu Ala Leu
1               5                   10                  15

Val Thr Asn Ser Met Ala Glu Thr Val Glu Ser Cys Leu Ala Lys Pro
            20                  25                  30

His Thr Glu Asn Ser Phe Thr Asn Val Trp Lys Asp Asp Lys Thr Leu
        35                  40                  45

Asp Arg Tyr Ala Asn Tyr Glu Gly Cys Leu Trp Asn Ala Thr Gly Val
    50                  55                  60

Val Val Cys Thr Gly Asp Glu Thr Gln Cys Tyr Gly Thr Trp Val Pro
65                  70                  75                  80

Ile Gly Leu Ala Ile Pro Glu Asn Glu Gly Gly Ser Glu Gly Gly
                85                  90                  95

Gly Ser Glu Gly Gly Gly Ser Glu Gly Gly Gly Thr Lys Pro Pro Glu
            100                 105                 110

Tyr Gly Asp Thr Pro Ile Pro Gly Tyr Thr Tyr Ile Asn Pro Leu Asp
        115                 120                 125

Gly Thr Tyr Pro Pro Gly Thr Glu Gln Asn Pro Ala Asn Pro Asn Pro
    130                 135                 140

Ser Leu Glu Glu Ser Gln Pro Leu Asn Thr Phe Met Phe Gln Asn Asn
145                 150                 155                 160
```

Arg Phe Arg Asn Arg Gln Gly Ala Leu Thr Val Tyr Thr Gly Thr Phe
                165                 170                 175

Thr Gln Gly Thr Asp Pro Val Lys Thr Tyr Gln Tyr Thr Pro Val
            180                 185                 190

Ser Ser Lys Ala Met Tyr Asp Ala Tyr Trp Asn Gly Lys Phe Arg Asp
        195                 200                 205

Cys Ala Phe His Ser Gly Phe Asn Glu Asp Pro Phe Val Cys Glu Tyr
        210                 215                 220

Gln Gly Gln Ser Ser Asp Leu Pro Gln Pro Val Asn Ala Gly Gly
225                 230                 235                 240

Gly Ser Gly Gly Gly Ser Gly Gly Ser Glu Gly Gly Ser Glu
                245                 250                 255

Gly Gly Gly Ser Glu Gly Gly Ser Glu Gly Gly Ser Gly Gly
            260                 265                 270

Gly Ser Gly Ser Gly Ala Met Val Arg Ser Pro Pro Cys Pro Ser Cys
        275                 280                 285

Pro Ala Pro Glu Phe Leu Gly Gly Pro Ser Val Phe Leu Phe Pro Pro
        290                 295                 300

Lys Pro Lys Asp Thr Leu Met Ile Ser Arg Thr Pro Glu Val Thr Cys
305                 310                 315                 320

Val Val Val Asp Val Ser Gln Glu Asp Pro Glu Val Gln Phe Asn Trp
                325                 330                 335

Tyr Val Asp Gly Val Glu Val His Asn Ala Lys Thr Lys Pro Arg Glu
            340                 345                 350

Glu Gln Phe Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
        370                 375                 380

Lys Gly Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Gln Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
        450                 455                 460

Leu Tyr Ser Arg Leu Thr Val Asp Lys Ser Arg Trp Gln Glu Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 12
<211> LENGTH: 6407
<212> TYPE: DNA
<213> ORGANISM: Enterobacteria phage

<400> SEQUENCE: 12
aacgctacta ctattagtag aattgatgcc acctttcag ctcgcgcccc aaatgaaaat      60
atagctaaac aggttattga ccatttgcga aatgtatcta atggtcaaac taaatctact    120
cgttcgcaga attgggaatc aactgttaca tggaatgaaa cttccagaca ccgtacttta    180

```
gttgcatatt taaaacatgt tgagctacag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tcttttgat gcaatccgct ttgcttctga ctataatagt    420
cagggtaaag acctgatttt tgatttatgg tcattctcgt ttctgaact gtttaaagca    480 tttgaggggg attcaatgaa tatttatgac gattccgcag tattggacgc tatccagtct    540
aaacatttta ctattacccc ctctggcaaa acttcttttg caaaagcctc tcgctatttt    600 ggttttatc gtcgtctggt aaacgagggt tatgatagtg ttgctcttac tatgcctcgt    660 aattccttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctggggt   1200 caaagatgag tgttttagtg tattctttcg cctctttcgt tttaggttgg tgccttcgta   1260
gtggcattac gtatttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagccttt   1560 ttttggaga ttttcaacgt gaaaaaatta ttattcgcaa ttcctttagt tgttcctttc   1620
tattctcact ccgctgaaac tgttgaaagt tgtttagcaa acccccatac agaaaattca   1680
tttactaacg tctggaaaga cgacaaaact ttagatcgtt acgctaacta tgagggctgt   1740
ctgtggaatg ctacaggcgt tgtagtttgt actggtgacg aaactcagtg ttacggtaca   1800
tgggttccta ttgggcttgc tatccctgaa atgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactttact   2100 caaggcactg accccgttaa aacttattac cagtacactc ctgtatcatc aaaagccatg   2160
tatgacgctt actggaacgg taaattcaga gactgcgctt ccattctgg ctttaatgag   2220 gatccattcg tttgtgaata tcaaggccaa tcgtctgacc tgcctcaacc tcctgtcaat   2280
gctggcggcg gctctggtgg tggttctggt ggcggctctg agggtggtgg ctctgaggg   2340 ggcggttctg agggtggcgg ctctgaggga ggcggttccg gtggtggctc tggttccggt   2400
gattttgatt atgaaaagat ggcaaacgct aataagggg ctatgaccga aaatgccgat   2460
gaaaacgcgc tacagtctga cgctaaaggc aaacttgatt ctgtcgctac tgattacggt   2520
```

-continued

```
gctgctatcg atggtttcat tggtgacgtt tccggccttg ctaatggtaa tggtgctact    2580
ggtgattttg ctggctctaa ttcccaaatg gctcaagtcg gtgacggtga taattcacct    2640
ttaatgaata atttccgtca atatttacct tccctccctc aatcggttga atgtcgccct    2700
tttgtctttg cgctggtaa accatatgaa ttttctattg attgtgacaa aataaactta    2760
ttccgtggtg tcttttgcgtt tcttttatat gttgccacct ttatgtatgt attttctacg    2820
tttgctaaca tactgcgtaa taaggagtct taatcatgcc agttcttttg ggtattccgt    2880
tattattgcg tttcctcggt ttccttctgg taactttgtt cggctatctg cttacttttc    2940
ttaaaagggg cttcggtaag atagctattg ctatttcatt gtttcttgct cttattattg    3000
ggcttaactc aattcttgtg ggttatctct ctgatattag cgctcaatta ccctctgact    3060
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg    3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg taaatatgg cgattctcaa ttaagcccta ctgttgagcg ttggctttat    3780
actggtaaga atttgtataa cgcatatgat actaaacagg cttttttctag taattatgat    3840
tccggtgttt attcttattt aacgccttat ttatcacacg gtcggtattt caaaccatta    3900
aatttaggtc agaagatgaa attaactaaa atatatttga aaaagttttc tcgcgttctt    3960
tgtcttgcga ttggatttgc atcagcattt acatatagtt atataaccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gcaaataatt ttgatatggt aggttctaac ccttccatta ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgctcct aaagatattt tagataacct tcctcaattc ctttcaactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
```

```
cctcacctct gttttatctt ctgctggtgg ttcgttcggt attttaatg gcgatgtttt    4980 agggctatca gttcgcgcat taaagactaa tagccattca aaatattgt ctgtgccacg    5040 tattcttacg ctttcaggtc agaagggttc tatctctgtt ggccagaatg tccctttat    5100 tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctctttttact    5340 cggtggcctc actgattata aaacacttc tcaggattct ggcgtaccgt tcctgtctaa    5400
aatcccttta atcggcctcc tgtttagctc ccgctctgat tctaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640 ggggctccc tttagggttc cgatttagtg ctttacggca cctcgacccc aaaaaacttg    5700
atttgggtga tggttcacgt agtgggccat cgccctgata acggttttt cgcctttga    5760 cgttggagtc cacgttcttt aatagtggac tcttgttcca aactggaaca acactcaacc    5820
ctatctcggg ctattctttt gatttataag ggattttgcc gatttcggcc tattggttaa    5880
aaaatgagct gatttaacaa aatttaacg cgaattttaa caaaatatta cgtttacaa    5940 tttaaatatt tgcttataca atcttcctgt ttttggggct tttctgatta tcaaccgggg    6000
tacatatgat tgacatgcta gttttacgat taccgttcat cgattctctt gtttgctcca    6060
gactctcagg caatgacctg atagcctttg tagacctctc aaaaatagct accctctccg    6120
gcattaattt atcagctaga acggttgaat atcatattga tggtgatttg actgtctccg    6180
gcctttctca cccttttgaa tctttaccta cacattactc aggcattgca tttaaaatat    6240
atgagggttc taaaattttt tatccttgcg ttgaaataaa ggcttctccc gcaaaagtat    6300
tacagggtca taatgttttt ggtacaaccg atttagcttt atgctctgag gctttattgc    6360
ttaattttgc taattctttg ccttgcctgt atgatttatt ggatgtt                6407
```

<210> SEQ ID NO 13  
<211> LENGTH: 509  
<212> TYPE: PRT  
<213> ORGANISM: Enterobacteria phage

<400> SEQUENCE: 13

```
Met Tyr Arg Met Gln Leu Leu Ser Cys Ile Ala Leu Ser Leu Ala Leu
1               5                   10                  15

Val Thr Asn Ser Met Ala Glu Thr Val Glu Ser Cys Leu Ala Lys Pro
            20                  25                  30

His Thr Glu Asn Ser Phe Thr Asn Val Trp Lys Asp Asp Lys Thr Leu
        35                  40                  45

Asp Arg Tyr Ala Asn Tyr Glu Gly Cys Leu Trp Asn Ala Thr Gly Val
    50                  55                  60

Val Val Cys Thr Gly Asp Glu Thr Gln Cys Tyr Gly Thr Trp Val Pro
65                  70                  75                  80

Ile Gly Leu Ala Ile Pro Glu Asn Glu Gly Gly Ser Glu Gly Gly
                85                  90                  95

Gly Ser Glu Gly Gly Gly Ser Glu Gly Gly Gly Thr Lys Pro Pro Glu
            100                 105                 110
```

```
Tyr Gly Asp Thr Pro Ile Pro Gly Tyr Thr Tyr Ile Asn Pro Leu Asp
        115                 120                 125

Gly Thr Tyr Pro Pro Gly Thr Glu Gln Asn Pro Ala Asn Pro Asn Pro
        130                 135                 140

Ser Leu Glu Glu Ser Gln Pro Leu Asn Thr Phe Met Phe Gln Asn Asn
145                 150                 155                 160

Arg Phe Arg Asn Arg Gln Gly Ala Leu Thr Val Tyr Thr Gly Thr Phe
                165                 170                 175

Thr Gln Gly Thr Asp Pro Val Lys Thr Tyr Gln Tyr Thr Pro Val
        180                 185                 190

Ser Ser Lys Ala Met Tyr Asp Ala Tyr Trp Asn Gly Lys Phe Arg Asp
        195                 200                 205

Cys Ala Phe His Ser Gly Phe Asn Glu Asp Pro Phe Val Cys Glu Tyr
        210                 215                 220

Gln Gly Gln Ser Ser Asp Leu Pro Gln Pro Val Asn Ala Gly Gly
225                 230                 235                 240

Gly Ser Gly Gly Gly Ser Gly Gly Ser Glu Gly Gly Ser Glu
                245                 250                 255

Gly Gly Gly Ser Glu Gly Gly Ser Glu Gly Gly Ser Gly Gly
        260                 265                 270

Gly Ser Gly Ser Gly Ala Met Val Arg Ser Asp Lys Thr His Thr Cys
        275                 280                 285

Pro Pro Cys Pro Ala Pro Glu Leu Leu Gly Gly Pro Ser Val Phe Leu
        290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
                340                 345                 350

Pro Arg Glu Glu Gln Tyr Asn Ser Thr Tyr Arg Val Val Ser Val Leu
                355                 360                 365

Thr Val Leu His Gln Asp Trp Leu Asn Gly Lys Glu Tyr Lys Cys Lys
        370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Glu Glu Met Thr Lys Asn Gln Val Ser Leu Thr Cys Leu Val Lys
                420                 425                 430

Gly Phe Tyr Pro Ser Asp Ile Ala Val Glu Trp Glu Ser Asn Gly Gln
                435                 440                 445

Pro Glu Asn Asn Tyr Lys Thr Thr Pro Pro Val Leu Asp Ser Asp Gly
        450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495

His Tyr Thr Gln Lys Ser Leu Ser Leu Ser Pro Gly Lys
                500                 505

<210> SEQ ID NO 14
<211> LENGTH: 131
```

```
<212> TYPE: PRT
<213> ORGANISM: Enterobacteria phage

<400> SEQUENCE: 14

Thr Lys Pro Pro Glu Tyr Gly Asp Thr Pro Ile Pro Gly Tyr Thr Tyr
1               5                   10                  15

Ile Asn Pro Leu Asp Gly Thr Tyr Pro Pro Gly Thr Glu Gln Asn Pro
            20                  25                  30

Ala Asn Pro Asn Pro Ser Leu Glu Glu Ser Gln Pro Leu Asn Thr Phe
        35                  40                  45

Met Phe Gln Asn Asn Arg Phe Arg Asn Arg Gln Gly Ala Leu Thr Val
    50                  55                  60

Tyr Thr Gly Thr Val Thr Gln Gly Thr Asp Pro Val Lys Thr Tyr Tyr
65                  70                  75                  80

Gln Tyr Thr Pro Val Ser Ser Lys Ala Met Tyr Asp Ala Tyr Trp Asn
                85                  90                  95

Gly Lys Phe Arg Asp Cys Ala Phe His Ser Gly Phe Asn Glu Asp Pro
            100                 105                 110

Phe Val Cys Glu Tyr Gln Gly Gln Ser Ser Asp Leu Pro Gln Pro Pro
        115                 120                 125

Val Asn Ala
    130

<210> SEQ ID NO 15
<211> LENGTH: 131
<212> TYPE: PRT
<213> ORGANISM: Enterobacteria phage

<400> SEQUENCE: 15

Thr Lys Pro Pro Glu Tyr Gly Asp Thr Pro Ile Pro Gly Tyr Thr Tyr
1               5                   10                  15

Ile Asn Pro Leu Asp Gly Thr Tyr Pro Pro Gly Thr Glu Gln Asn Pro
            20                  25                  30

Ala Asn Pro Asn Pro Ser Leu Glu Glu Ser Gln Pro Leu Asn Thr Phe
        35                  40                  45

Met Phe Gln Asn Asn Arg Phe Arg Asn Arg Gln Gly Ala Leu Thr Val
    50                  55                  60

Tyr Thr Gly Thr Val Thr Gln Gly Thr Asp Pro Val Lys Thr Tyr Tyr
65                  70                  75                  80

Gln Tyr Thr Pro Val Ser Ser Lys Ala Met Tyr Asp Ala Tyr Trp Asn
                85                  90                  95

Gly Lys Phe Arg Asp Cys Ala Phe His Ser Gly Phe Asn Glu Asp Pro
            100                 105                 110

Phe Val Cys Glu Tyr Gln Gly Gln Ser Ser Asp Leu Pro Gln Pro Pro
        115                 120                 125

Val Asn Ala
    130

<210> SEQ ID NO 16
<211> LENGTH: 131
<212> TYPE: PRT
<213> ORGANISM: Enterobacteria phage

<400> SEQUENCE: 16

Thr Lys Pro Pro Glu Tyr Gly Asp Thr Pro Ile Pro Gly Tyr Thr Tyr
1               5                   10                  15

Ile Asn Pro Leu Asp Gly Thr Tyr Pro Pro Gly Thr Glu Gln Asn Pro
```

```
                    20                  25                  30
Ala Asn Pro Asn Pro Ser Leu Glu Glu Ser Gln Pro Leu Asn Thr Phe
            35                  40                  45

Met Phe Gln Asn Asn Arg Phe Arg Asn Arg Gln Gly Ala Leu Thr Val
    50                  55                  60

Tyr Thr Gly Thr Val Thr Gln Gly Thr Asp Pro Val Lys Thr Tyr Tyr
65                  70                  75                  80

Gln Tyr Thr Pro Val Ser Ser Lys Ala Met Tyr Asp Ala Tyr Trp Asn
            85                  90                  95

Gly Lys Phe Arg Asp Cys Ala Phe His Ser Gly Phe Asn Glu Asp Pro
                100                 105                 110

Phe Val Cys Glu Tyr Gln Gly Gln Ser Ser Asp Leu Pro Gln Pro Pro
            115                 120                 125

Val Asn Ala
    130

<210> SEQ ID NO 17
<211> LENGTH: 128
<212> TYPE: PRT
<213> ORGANISM: Enterobacteria phage

<400> SEQUENCE: 17

Ser Pro Gly Glu Lys Thr Glu Ser Trp Ser Ile Arg Ala Gln Val Glu
1               5                   10                  15

Gly Asp Ile Gln Arg Ser Val Pro Asp Glu Pro Ser Glu Gln Thr
            20                  25                  30

Pro Glu Glu Ile Cys Glu Ala Lys Pro Pro Ile Asp Gly Val Phe Asn
            35                  40                  45

Asn Val Phe Lys Gly Asp Glu Gly Gly Phe Tyr Ile Asn Tyr Asn Gly
        50                  55                  60

Cys Glu Tyr Glu Ala Thr Gly Val Thr Val Cys Gln Asn Asp Gly Thr
65                  70                  75                  80

Val Cys Ser Ser Ser Ala Trp Lys Pro Thr Gly Tyr Val Pro Glu Ser
            85                  90                  95

Gly Glu Pro Ser Ser Pro Leu Lys Asp Gly Asp Thr Gly Gly Thr
            100                 105                 110

Gly Glu Gly Gly Ser Asp Thr Gly Gly Asp Thr Gly Gly Asp Thr
        115                 120                 125

<210> SEQ ID NO 18
<211> LENGTH: 128
<212> TYPE: PRT
<213> ORGANISM: Enterobacteria phage

<400> SEQUENCE: 18

Ser Pro Ser Glu Lys Thr Glu Ser Trp Ser Ile Arg Ala Gln Val Glu
1               5                   10                  15

Gly Asp Met Gln Arg Ser Val Pro Asp Glu Pro Ser Glu Gln Thr
            20                  25                  30

Pro Glu Glu Ile Cys Glu Ala Lys Pro Pro Ile Asp Gly Val Phe Asn
            35                  40                  45

Asn Val Ser Lys Gly Asp Glu Gly Gly Phe Tyr Ile Asn Tyr Asn Gly
        50                  55                  60

Cys Glu Tyr Glu Ala Thr Gly Val Thr Val Cys Gln Asn Asp Gly Thr
65                  70                  75                  80

Val Cys Ala Ser Ser Ala Trp Lys Pro Thr Gly Tyr Val Pro Glu Ser
```

```
            85                  90                  95
Gly Glu Ser Ser Ser Pro Val Lys Asp Gly Asp Thr Gly Gly Thr
                100                 105                 110

Gly Glu Gly Gly Ser Asp Thr Gly Asp Thr Gly Gly Gly Asp Thr
            115                 120                 125

<210> SEQ ID NO 19
<211> LENGTH: 161
<212> TYPE: PRT
<213> ORGANISM: Enterobacteria phage

<400> SEQUENCE: 19

Ser Thr Pro Asp Thr Val Thr Pro Gly Gln Thr Val Asn Leu Pro Ser
1               5                   10                  15

Asp Leu Ser Thr Leu Ser Ile Pro Ala Asn Val Val Lys Ser Asp Ser
            20                  25                  30

Ile Gly Ser Gln Phe Ser Leu Tyr Thr Asn Ala Ser Cys Thr Met Cys
        35                  40                  45

Ser Gly Tyr Tyr Leu Ser Asn Asn Ala Asp Ser Ile Ala Ile Ala Asn
    50                  55                  60

Ile Thr Glu Thr Val Lys Ala Asp Tyr Asn Gln Pro Asp Met Trp Phe
65                  70                  75                  80

Glu Gln Thr Asp Ser Asp Gly Asn His Val Lys Ile Leu Gln Asn Ser
                85                  90                  95

Tyr Lys Ala Val Ser Tyr Asn Val Glu Ser Lys Gln Ser Asp Val Asn
            100                 105                 110

Asn Pro Thr Tyr Ile Asn Tyr Ser Tyr Val Asn Val Lys Gln Val
        115                 120                 125

Ser Tyr Asp Thr Ser Asn Val Cys Ile Met Asn Trp Glu Thr Phe Gln
    130                 135                 140

Asn Lys Cys Asp Ala Ser Arg Ala Val Leu Ile Thr Asp Thr Val Thr
145                 150                 155                 160

Pro

<210> SEQ ID NO 20
<211> LENGTH: 227
<212> TYPE: PRT
<213> ORGANISM: Enterobacteria phage

<400> SEQUENCE: 20

Met Ala Glu Thr Val Glu Ser Cys Leu Ala Lys Ser His Thr Glu Asn
1               5                   10                  15

Ser Phe Thr Asn Val Trp Lys Asp Asp Lys Thr Leu Asp Arg Tyr Ala
            20                  25                  30

Asn Tyr Glu Gly Cys Leu Trp Asn Ala Thr Gly Val Val Val Cys Thr
        35                  40                  45

Gly Asp Glu Thr Gln Cys Tyr Gly Thr Trp Val Pro Ile Gly Leu Ala
    50                  55                  60

Ile Pro Glu Asn Glu Gly Gly Ser Glu Gly Gly Ser Glu Gly
65                  70                  75                  80

Gly Gly Ser Glu Gly Gly Thr Lys Pro Pro Glu Tyr Gly Asp Thr
            85                  90                  95

Pro Ile Pro Gly Tyr Thr Tyr Ile Asn Pro Leu Asp Gly Thr Tyr Pro
        100                 105                 110

Pro Gly Thr Glu Gln Asn Pro Ala Asn Pro Asn Pro Ser Leu Glu Glu
            115                 120                 125
```

```
Ser Gln Pro Leu Asn Thr Phe Met Phe Gln Asn Asn Arg Phe Arg Asn
        130                 135                 140

Arg Gln Gly Ala Leu Thr Val Tyr Thr Gly Thr Val Thr Gln Gly Thr
145                 150                 155                 160

Asp Pro Val Lys Thr Tyr Tyr Gln Tyr Thr Pro Val Ser Ser Lys Ala
                165                 170                 175

Met Tyr Asp Ala Tyr Trp Asn Gly Lys Phe Arg Asp Cys Ala Phe His
            180                 185                 190

Ser Gly Phe Asn Glu Asp Leu Phe Val Cys Glu Tyr Gln Gly Gln Ser
        195                 200                 205

Ser Asp Leu Pro Gln Pro Pro Val Asn Ala Pro Ser Gly His His His
    210                 215                 220

His His His
225

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 21

Gly Xaa Phe Xaa Gly Xaa Phe
1               5

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Lys Leu Val Phe Phe
1               5

<210> SEQ ID NO 23
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
atggctgaaa ctgttgaaag ttgtttagca aaatcccata cagaaaattc atttactaac     60
gtctggaaag acgacaaaac tttagatcgt tacgctaact atgagggctg tctgtggaat    120
```

```
gctacaggcg ttgtagtttg tactggtgac gaaactcagt gttacggtac atgggttcct    180
attgggcttg ctatccctga aaatgagggt ggtggctctg agggtggcgg ttctgagggt    240
ggcggttctg agggtggcgg tactaaacct cctgagtacg gtgataccc tattccgggc     300 tatacttata tcaaccctct cgacggcact tatccgcctg gtactgagca aaacccggct    360
aatcctaatc cttctcttga ggagtctcag cctcttaata ctttcatgtt tcagaataat    420
aggttccgaa ataggcaggg ggcattaact gtttatacgg gcactgttac tcaaggcact    480
gaccccgtta aaacttatta ccagtacact cctgtatcat caaaagccat gtatgacgct    540
tactggaacg gtaaattcag agactgcgct ttccattctg gctttaatga ggatttattt    600
gtttgtgaat atcaaggcca atcgtctgac ctgcctcaac ctcctgtcaa tgctccgtcc    660
gggcatcatc atcatcatca ttaa                                           684
```

<210> SEQ ID NO 24
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Met Ala Glu Thr Val Glu Ser Cys Leu Ala Lys Ser His Thr Glu Asn
1               5                   10                  15

Ser Phe Thr Asn Val Trp Lys Asp Asp Lys Thr Leu Asp Arg Tyr Ala
            20                  25                  30

Asn Tyr Glu Gly Cys Leu Trp Asn Ala Thr Gly Val Val Cys Thr
        35                  40                  45

Gly Asp Glu Thr Gln Cys Tyr Gly Thr Trp Val Pro Ile Gly Leu Ala
    50                  55                  60

Ile Pro Glu Asn Glu Gly Gly Gly Ser Glu Gly Gly Ser Glu Gly
65                  70                  75                  80

Gly Gly Ser Glu Gly Gly Thr Lys Pro Pro Glu Tyr Gly Asp Thr
            85                  90                  95

Pro Ile Pro Gly Tyr Thr Tyr Ile Asn Pro Leu Asp Gly Thr Tyr Pro
            100                 105                 110

Pro Gly Thr Glu Gln Asn Pro Ala Asn Pro Asn Pro Ser Leu Glu Glu
        115                 120                 125

Ser Gln Pro Leu Asn Thr Phe Met Phe Gln Asn Asn Arg Phe Arg Asn
130                 135                 140

Arg Gln Gly Ala Leu Thr Val Tyr Thr Gly Thr Val Thr Gln Gly Thr
145                 150                 155                 160

Asp Pro Val Lys Thr Tyr Tyr Gln Tyr Thr Pro Val Ser Ser Lys Ala
                165                 170                 175

Met Tyr Asp Ala Tyr Trp Asn Gly Lys Phe Arg Asp Cys Ala Phe His
            180                 185                 190

Ser Gly Phe Asn Glu Asp Leu Phe Val Cys Glu Tyr Gln Gly Gln Ser
        195                 200                 205

Ser Asp Leu Pro Gln Pro Val Asn Ala Pro Ser Gly His His His
    210                 215                 220

His His His
225
```

```
<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 25

His His His His His His
1               5
```

What is claimed is:

1. A nucleic acid encoding a fusion protein that consists essentially of an amyloid-binding polypeptide linked directly or through a short peptide linker to an immunoglobulin IgG constant region, wherein the amyloid-binding polypeptide comprises at least one of:
   (a) a wild type gene 3 protein (g3p) or a mutant thereof that retains the ability to bind to amyloid, or
   (b) an amyloid-binding fragment of wild type g3p, or a mutant thereof that retains the ability to bind to amyloid.

2. The nucleic acid according to claim 1, wherein the encoded amyloid-binding polypeptide is at least 95% identical to SEQ ID NO:1 or an amyloid-binding fragment of SEQ ID NO:1.

3. The nucleic acid according to claim 1, wherein the encoded amyloid-binding polypeptide is at least 95% identical to the N1-N2 fragment of SEQ ID NO:1.

4. A vector comprising the nucleic acid of claim 1.

5. A host cell comprising the vector of claim 4.

6. A method of making a fusion protein that consists essentially of an amyloid-binding polypeptide linked directly or through a short peptide linker to an immunoglobulin constant region, wherein the amyloid-binding polypeptide comprises at least one of:
   (a) a wild type g3p or a mutant thereof that retains the ability to bind to amyloid, or
   (b) an amyloid-binding fragment of wild type g3p or a mutant thereof that retains the ability to bind to amyloid comprising providing a host cell transformed with the vector of claim 4, expressing the fusion protein encoded by the nucleic acid in the vector, and isolating the expressed fusion protein.

7. The host cell of claim 5, wherein the host cell is selected from an insect cell, a plant cell, a fungal cell, a bacterial cell, an animal cell line, and a transgenic animal cell.

8. The host cell of claim 5, wherein the host cell is selected from the group consisting of a *Spodoptera frugiperda* cell, an *E. coli* cell, a CHO cell, a CHO-derived cell, a COS cell, and a HeLa cell.

9. The host cell of claim 8, wherein the host cell is a CHO cell or a CHO-derived cell.

10. The method of claim 6, wherein the host cell is selected from an insect cell, a plant cell, a fungal cell, a bacterial cell, an animal cell line, and a transgenic animal cell.

11. The method of claim 6, wherein the host cell is selected from the group consisting of a *Spodoptera frugiperda* cell, an *E. coli* cell, a CHO cell, a CHO-derived cell, a COS cell, and a HeLa cell.

12. The method of claim 6, wherein the host cell is a CHO cell or a CHO-derived cell.

* * * * *